US007105316B2

(12) United States Patent
Pettersson-Fernholm et al.

(10) Patent No.: US 7,105,316 B2
(45) Date of Patent: Sep. 12, 2006

(54) *NEISSERIA* LACTOFERRIN BINDING PROTEIN

(75) Inventors: Annika Margareta Pettersson-Fernholm, Utrecht (NL); Johannes Petrus Maria Tommassen, Utrecht (NL)

(73) Assignees: University of Utrecht, Utrecht (NL); Technology Foundation, Ha Nieuwegein (NL)

( * ) Notice: Subject to any disclaimer, the term of this patent is extended or adjusted under 35 U.S.C. 154(b) by 72 days.

(21) Appl. No.: 10/735,098

(22) Filed: Dec. 12, 2003

(65) Prior Publication Data

US 2004/0131634 A1   Jul. 8, 2004

Related U.S. Application Data

(63) Continuation of application No. 09/485,760, filed as application No. PCT/EP98/05117 on Aug. 10, 1998, now abandoned.

(30) Foreign Application Priority Data

Aug. 15, 1997 (GB) ................................. 9717423.9
Feb. 5, 1998 (GB) ................................. 9802544.8

(51) Int. Cl.
 *C12N 15/09* (2006.01)
(52) U.S. Cl. ................. 435/69.3; 435/69.1; 435/320.1; 435/71.1; 435/252.3; 536/23.7; 536/24.1; 536/24.2; 536/24.32; 424/250.1
(58) Field of Classification Search ............... 536/23.7, 536/24.1, 24.2, 24.32; 435/320.1, 69.1, 69.3, 435/71.1, 252.3; 424/250.1
See application file for complete search history.

(56) References Cited

U.S. PATENT DOCUMENTS 6,028,049 A  *  2/2000  Jacobs et al. ................... 514/2
6,048,539 A     4/2000  Schryvers et al.

FOREIGN PATENT DOCUMENTS

| CA | 2162193 | | 5/1997 |
| FR | 92 07493 | * | 6/1992 |
| WO | WO 95/33049 | * | 12/1995 |

OTHER PUBLICATIONS

Mikayama et al. (Nov. 1993. Proc.Natl.Acad.Sci. USA, vol. 90 : 10056-10060).*
Rudlinger et al. (Jun. 1976. Peptide Hormones. Biol.Council. pp. 5-7).*
Pettersson (Infect. Immun. 61(11): 4724-4733. 1993) Abstract only right now.*
Biswas et al (Infect. Immun. 1995. 63(8): 2958-2967).*
Pettersson et al (Microb. Pathog. 17(6): 395-408. 1994).*

Schryvers, et al., "Identification and Characterization of the Human Lactoferrin-Binding Protein from *Neisseria meningitidis*". *Infection & Immunity*, 56(5): 1144-1149 (1998).
Biswas, et al., "Characterization of *lbpA*, the Structure Gene for a Lactoferrin Receptor in *Neisseria gonorrhoeae*". *Infection & Immunity*, 63(8): 2958-2967 (1995).
Pettersson, et al., "Identification of the *iroA* Gene Product of *Neisseria meningitidis* as a Lactoferrin Receptor". *Journal of Bacteriology*, 176(6): 1764-1766 (1994).
Pettersson, et al., "Molecular Characterization of the Structural Gene for the Lactoferrin Receptor of the Meningococcal Strain H44/76". *Microbial Pathogenesis*, 17: 395-408 (1994).
Pettersson, et al., "Molecular Characterization of the 98-Kilodalton Iron-Regulated Outer Membrane Protein of *Neisseria meningitidis*". *Infection & Immunity*, 61(11): 4724-4733 (1993).
Pettersson, et al., "Monoclonal Antibodies Against the 70-Kilodalton Iron-Regulated Protein of *Neisseria meningitidis* are Bactericidal and Strain Specific". *Infection and Immunity*, 58(9): 3036-3041 (1990).
Gschwentner, et al., "Lactoferrin and Its Receptor(s): Modulators of Inflammation?" *Abstracts of the Third International Conference on Lactoferrin*, pp. 68 (1997).
Bonnah, et al., "Biochemical Analysis of Lactoferrin Receptors in the Neisseriaceae: Identification of a Second Bacterial Lactoferrin Receptor Protein", *Microbial Pathogenesis*, 19:285-297 (1995).
Pettersson, et al., "Molecular Characterization of the Structural Gene for the Lactoferrin Receptor of the Meningococcal Strain H44/76", *Microbial Pathogenesis*, 17:395-408 (1994).
Biswas, et al., "Characterization of *lpp*A, the Structural Gene for a Lactoferrin Receptor in *Neisseria gonorrhoeae*", *Infection and Immunity*, 63(8):2958-2967 (1995).
Petersson, et al., "Molecular Characterization of LbpB, the Second Lactoferrin-Binding Protein of *Neisseria meningitidis*", *Molecular Microbiology*, 27(3):599-610 (1998).
Lewis, et al., "Identification and Molecular Analysis of lbpBA, Which Encodes the Two-Component Meningococcal Lactoferrin Receptor", *Infection and Immunity*, 66(6):3017-3023 (1998).
Bonnah, et al., "Preparation and Characterization of *Neisseria meningitidis* Mutants Deficient in Production of the Human Lactoferrin-Binding Proteins LbpA and LbpB", *Journal of Bacteriology*, 180(12):3080-3090 (1998).
Bonnah, et al., "Bacterial Lactoferrin Receptors in the Neisseriaceae", In: *Lactoferrin: Interactions and Biological Functions*, pp. 277-301 (1997). Editors: T.W. Hutchens and B. Lonnerdal, Humana Press Inc., Totowa, New Jersey.
Feavers I and Maiden M, "A gonococcal porA pseudogene: Implication for understanding the evolution and pathogenicity of Neisseria gonorrhoeae," *Molecular Microbiology*, 30: No. 3, pp. 647-656 (1998).

(Continued)

*Primary Examiner*—Jennifer E. Graser
(74) *Attorney, Agent, or Firm*—William T. Han; Edward R. Gimmi; Charles M. Kinzig

(57) ABSTRACT

LbpB polypeptides and polynucleotides and methods for producing such polypeptides by recombinant techniques are disclosed. Also disclosed are methods for utilizing LbpB polypeptides and polynucleotides in the design of protocols for the treatment of neisserial disease, among others, and diagnostic assays for such conditions.

8 Claims, 15 Drawing Sheets

OTHER PUBLICATIONS

Shyamala V and Ferro-Luzzi Ames G, "Genome walking by Single specific primer Polymerase chain reaction: SSP-PCR," *Gene 84*: pp. 1-8 (1989).

Ogunnariwo J and Schryvers A. "Rapid identification and cloning of bacterial transferring and lactoferrin receptor protein genes." *Journal of Bacteriology 178*: No. 24, pp. 7326-7328 (1996).

Perkins-Balding D, Ratliff-Griffin M. and Stojiljkovice I. "Iron transport systems in Neisseria Meningitidis." *Microbiology and Molecular Biology Reviews 68*: pp. 154-171 (2004).

Prinz et al., "Structural characterization of the lactoferrin receptor from Neisseria meningitidis." *181*: pp. 4417-4419 (1999).

* cited by examiner

Fig.3

```
                               ↓
LbpB  - MCKP--NYGGIVLLPLLLASCIGGNFGVQPVVESTPTAYPVIFKSKDVPT  -48
        | |  |  ||  || ||| ||| |
TbpB  - MNNPLVNQAAMVLPVFLLSACLGG--GGSFDLDSVETVQDMHSKPKYEDE  -48

LbpB  - PPPAKPSIEITPVNRPAVGAAMRLPRRNTAFHREDGIEIPNSKQAEEKLS  -98
         | |       |||||   |        |
TbpB  - KSQPESQQDVSENSGAAYGFAVKLPRRNAHFNPKY-KEKHKPLGSMDWKK -97

LbpB  - FQEGDVLFLYGSKGNKLQQLKSEIHKRDSDVEIRTSEKENKKYDYKFVDA -148
        ||            |      |   |     |           |
TbpB  - LQRGEPNSF--SERDELEKKRGSSELIESKWEDGQSRVVGYT-NFTYVRS -144

LbpB  - GYVYVKGKDEIKWTSDYKQFSNRLGYDGFVYYSGERPSQSLPSAGTVEYS -198
        ||||   |  |         |    |   ||  ||  |  ||  |
TbpB  - GYVYLN-KNNIDIKNNIVLF----GPDGYLYYKGKEPSKELPSE-KITYK -188

LbpB  - GNWQYMTDA-KRHRA---GKAVGIDNLGYYTFYGNDVGATSYAAKDVDER -244
        |  | |||    |     |    ||||  |       |    |
TbpB  - GTWDYVTDAMEKQRFEGLGSAAGGDKSGALSALEEGVLRNQAEASSGHTD -238

LbpB  - EKHPAKYTVDFGNKTLIGELIKNQYVKPSE----KQKPLTTYNITADLNGN -291
         |||   ||  | | |           ||    | ||||||||
TbpB  - FGMTSEFEVDFSDKTIKGTLYRNNRITQNNSENKQIKITRYTIQATLHGN -288

LbpB  - RFTGSAKVNPDLAKSHANKEHLFFHADADQRLEGGFFGDKGEELAGRFIS -341
        || |       |   |   |   ||   |||| | ||||||| |
TbpB  - RFKGKALAA---DKGATNGSHPFI-SDSDS-LEGGFYGPKGEELAGKFLS -333

LbpB  - NDNSVFGVFAGKQNSPVPSGKHTKILDSLKISVDEASGENPRPFAISPMP -391
        ||| |  ||  ||                      | |    |
TbpB  - NDNKVAAVPGAKQRDKKDGENAA---GPATETVIDAYRITGEEFKKEQID -380

LbpB  - DFGHPDKLLVEGHEIPLVSQE----KTIELADGRKMTVSACCDFLTYVKL -437
         | | |||| |   |   |         |     |        || ||
TbpB  - SFGDVKKLLVDGVELSLLPSEGNKAAFQHEIEQNGVKATVCCSNLDYMSF -430

LbpB  - GRIKTERPAAKPKAQDEEDSDIDNGEESEDEIGDEEEGTEDAAAGDBGSE -487
        ||  |
TbpB  - GKLSKEN---------------------------------------- -437

LbpB  - EDEATENEDGEEDEAFEPEEESSAEGNGSSNAILPVPEASKGRDIDLFLK -537
                                                        | |||
TbpB  - -------------------------------------------KDDMFLQ -444

LbpB  - GIRTAETNIPQTGEA--RYTGTWEARIGKPIQWDNHADKEAA--KAVFTV -583
        | ||    ||  ||   || |    |||  |    |  |      |||
TbpB  - GVRTPVSDVAARTSANAKYRGTWYGYIANGTSWSGEASNQEGGNRAEFDV -494

LbpB  - DFGKKSISGTLTEKNGVEPAFRIENGVIEGNGFHATARTRDDGIDLSGQG -633
        ||  ||||||| ||   |||||   |||  |   ||  |  |    |
TbpB  - DFSTKKISGTLTAKDRTSPAFTI-TAMIKDNGFSGVAKTGENGFALDPQN -543

B1
LbpB  - STKPQIFKANDLRVEGGFYGPKAEELGGIIFNNDGKSLGITEGTENKVEA -683
        | |||| |||| |||| ||||   | | ||
TbpB  - TGNSH-YTHIEATVSGGFYGKNAIEMGG--------SFSFPGNA------ -578

A1       C1   D1         E1
LbpB  - DVDVDVDVDVDADADVEQLKPEVKPQFGVVFGAKKDNKEVEK -725
                                      |  ||||||
TbpB  - -------------PEGKQEKA------SVVFGAKRQ--QLVQ -599
```

FIGURE 4

```
     -35                          -10
CGGGTTGATATTATCTGTACATATTAA TATAATGATAATTATTATTA
        ---                      -----

ATCAAATAGGAGGAAAAGTAGGGATGTGTAAACCGAATTATGGCGGC
         ---------
```

Figure 9

```
BNCV      MCKPNYGGIVLLPLLLASCIGGNFGVQPVVESTPTAYPVTFKSK-----DVPTPP     50
H44/76    MCKPNYGGIVLLPLLLASCIGGNFGVQPVVESTPTAYPVTFKSK-----DVPTPP     50
M990      MCKPNYGGIVLLPLLLASCIGGNFGVQPVVESTPTA-PTLSDSKSSNPADKPAPA     54
M981      MCKPNYGGIVLLPLLLASCIGGNFGVQPVVESTPTAYPVTFKSK-----DVPTSP     50
881607    MCKPNYGGIVLLPLLLASCIGGNFGVQPVVESTPTAYPVTFKSK-----DVPTSP     50
          *******************************************     **    * *

BNCV      PAKPSIEITPVNR--PAVGAAMRLPRRNTAFHREDGTEIPNSKQAEEKLSFQEGD    103
H44/76    PAKPSIETTPVPSTGPAVGAAMRLLRRIFATSDKVGNDFPNSKQAEEKLSFKEGD    105
M990      PAEPSVEITPVKR--PAVGAAMRLPRRNIATFDKNGNEIPNSKQAEEYLPLKEKD    107
M981      PAGSSVETTPVNQ--PAVGAAMRLLRRNTAFHREDGTAIPDSKQAEEKLSFKEGD    103
881607    PAGSSVETTPVNR--PAVGAAMRLLRRNIATSDKDGNDFPNSKQAEEKLSFKEED    103
          **  *  * ***    ********  **   *     *  ******  *    *  *

BNCV      VLFLYGSKGNKLQQLKSEIHKRDSDVEIRTSEKENKKYDYKFVDAGYVYVK-GKD    157
H44/76    VLFLYGSKKDKLQWLKDKIHQRNPNVEIRTSENENKKYGYEFVDAGYVYTKNGTD    160
M990      ILFLDGTPKEQADKLKKEINGRHPNAPIYTSDLKDDAYQYKYVRAGYVYTRYGTD    162
M981      VLFLYGSKENKLQQLKSEIHKRNPEASITTSENENKKYNYRFVSAGYVFTKNGKD    158
881607    ILFLYGSKKDQRQQLKDKIRQPNPTASITTSEKKNKKYDYKFVDAGYVYTKDGKD    158
          ***  *        **  *            *  **    *  *  *  ****     *  *

BNCV      EIKWTSDYKQFSNRLGYDGFVYYSGERPSQSLPSAGTVEYSGNWQYMTDAKRHRA    212
H44/76    EIEWTSNRKQFSNRFGYDGFVYYSGEHPSQSLPSAGTVQYSGNWQYMTDAIRHRT    215
M990      EIEQNSGGKRVTHRLGYDGFVYYSGERPSQSLPSAGTVEYSGNWQYMTDAKRHRA    217
M981      EIEKTSDEKQFSNRLGYDGFVYYLGEHPSQSLPSAGTVKYSGNWQYMTDAIRHRR    213
881607    EIEWTSNYKQSTNRFGYDGFVYYSGEHPSQSLPSAGTVKYSGNWQYMTDAIRHRT    213
          **   *   *    * ********  ** ************ *********** ***

BNCV      GKAVG-IDNLGYYTFYGNDVGATSYAAKDVDEREKHPAKYTVDFGNKTLTGELIK    266
H44/76    GKAGDPSEDLGYLVYYGQNVGATSYAATADDREGKHPAEYTVDFDKKTLTGQLIK    270
M990      GQAVG-IDNLGYITFYGNDVGATSYAAKDVDEREKHPAKYTVDFDNKTMNGKLIK    271
M981      GKGVS-SVDLGYTTYYGNEIGAASYEARDADGREKHPAEYTVNFDKKNLEGKLIK    267
881607    GKAGDPSEDLGYIVYYGQNVGATSYAATADDREGKHPAEYTVNFDQKTLNGKLIK    268
          *         ***    **   ** **   *        ****  *** * *     * ***

BNCV      NQYV--KPSEKQKPLTIYNITADLNGNRFTGSAKVNPDLAKSHANKEHLFFHADA    319
H44/76    NQYV-QKKTDEKKPLTIYDITATLDGNRFTGSAKVNTELKTSHADKEHLFFHTDA    324
M990      NQYVRNKKDEPKKPLTIYDITAKLDGNRFTGSAKVNPDLAKNLAGNERLFFHADA    326
M981      NQYV-QKRDDPKNPLTIYNITATLDGNRFTGSAKVSTEVKTQHADKEYLFFHTDA    321
881607    NQYV-QKRDDPKKPLTIYDITAKLDGNRFTGSAKVNTEVKTNHADKEYLFFHTDA    322
          ****   *     ***** ***  * **********        *  * **** **

BNCV      DQRLEGGFFGDKGEELAGRFISNDNSVFGVFAGKQ---------NSPVPSGKHT    364
H44/76    DQRLEGGFFGDKGEELAGRFISNDNSVFGVFAGK-KTNASNAADTNPAMPSEKHT    378
M990      DQRLEGGFFGDNGEELAGRFISNDNSVFGVFAGK-KTETANAADTKPALPSGKHT    380
M981      DQRLEGGFFGDNGEELAGRFISNDNSVFGVFAGKQKTETANASDTNPALPSGKHT    376
881607    DQRLEGGFFGDKGEELAGRFISNDNSVFGVFAGKQKTETANASDTNPALPSGKHT    377
          ***********  *********************                        ** ***

BNCV      KILDSLKISVDEASGENPRPFAISPMPDFGHPDKLLVEGHEIPLVSQEKTIELAD    419
H44/76    KILDSLKISVDEATDKNARPFAISPLPDFGHPDKLLVEGREIPLVSQEKTIELAD    433
M990      KILDSLKISVDEATDGHARKFAISSMPDFGHPDKLLVEGREIPLVNEEQIIKLAD    435
M981      KILDSLKISVDEATDDHARKFAISTMPDFGHPDKLLVEGREIPLVSQEKTIELAD    431
881607    KILDSLKISVDEASGENPRPFEVSTMPDFGHPDKLLVEGREIPLVNKEQTIDLAD    432
          *************    *  *    ************* ****    *  ***
```

Figure 9 (continued)

```
BNCV     GRKMTVSACCDFLTYVKLGRIKTERPAAKPKAQD----EEDSDIDNGEES-EDEI     469
H44/76   GRKMTVRACCDFLTYVKLGRIKTDRPASKPKAEDKGKDEEDTGVGNDEEGTEDEA     488
M990     GRKMTVRACCDFLTYVKLGRIKTDRPASKPKAEDKGEDEEGAGVDNDEES-EDEA     489
M981     GRKMTIRACCDFLTYVKLGRIKTDRPAVKPKAQD----EEDSDIDNGEES-EDEI     481
881607   GRKMTVRACCDFLTYVKLGRIKTERPAVQPKAQDEEGDEEGVGVDNGKES-EDEI     486
         *****  ***************  ***  *** *     **    *  *  ***

BNCV     GDEEEGTEDAAAGDEGSEEDEAT---ENEDGEEDEA---------EEPEEESSA      511
H44/76   AEGSEGGEDEIGDEGGGAEDEAA---ENEGGEEDEA-------EEPEEPEEESPA     533
M990     VEDEGGEEDETSEEDNGEDEEATAEEETEEVDEAEE-------EEVEEPEEKSPA     537
M981     SEDDNGEDEVTEEEEAEETEEETDEDEEEEPEETEETEETEETEETEETEEKSPT     536
881607   GDEESTGDEVVEDEDEDEDEEEI---EEPEEEAEE---------EEPEEELPA      528
                  *       *  *  *  *              ** **

BNCV     E-GNGSSNAILPVPEASKGRDIDLFLKGIRTAETNIPQTGEARYTGTWEARIGKP     565
H44/76   EGGGGGSDGILPAPEAPKGRDIDLFLKGIRTAEADIPQTGKARYTGTWEARISKP     588
M990     E-GNGGSGSILPALEASKGRDIDLFLKGIRTAETDIPQSGTAHYTGTWEARIGKP     591
M981     EEGNGGSGSILPTPEASKGRDIDLFLKGIRTAEADIPQIGKARYTGTWEARIGVP     591
881607   EEGNGGSGSILPTPEASKGRDIDLFLKGIRTAEADIPKNGTAHYTGTWEARIGVS     583
          *  *  *   ***   **  ****************   **   *  *********

BNCV     -----------IQWDNHADKEAAKAVFTVDFGKKSISGTLTEKNGVEPAFRIEN      608
H44/76   -----------IQWDNHADKKAAKAEFDVDFGEKSISGTLTEKNGVQPAFHIEN      631
M990     -----------IQWDNQADEKAAKAEFTVDFDKKSISGKLTEQNGVEPAFHIED      634
M981     DKKGEQLDGTTSIQKDSYA-NQAAKAEFDVDFGAKSLSGKLTEKNDTHPAFYIEK     645
881607   D-------SGTSIQKDSYA-NQGAKAEFTVDFEAKTVSGMLTEKNDTTPAFYIEK     630
                          **  *  *     ***  *  ***    *    **  ***  **

BNCV     GVIEGNGFHATARTRDDGIDLSGQGSTKPQIFKANDLRVEGGFYGPKAEELGGII     663
H44/76   GVIEGNGFHATARTRDNGINLSGNDSTNPPSFKANNLLVTGGFYGPQAEELGGTI     686
M990     GKIDGNGFHATARTRESGINLSGNGSTDPKTFQASNLRVEGGFYGPQAAELGGTI     689
M981     GVIDGNGFHALARTRENGVDLSGQGSTNPQSFKASNLLVEGGFYGPQAAELGGNI     700
881607   GVIDGNGFHALAHTRENGIDLSGQGSTNPKNFKADNLLVTGGFYGPQAAELGGNI     685
         *  * ****** *  **   *   ***  **   *  *     *  *  ****** *  **** *

BNCV     FNNDGKSLGITEGTENKVEADVDVDVDVDADADVE-QLKP-EVKPQFGVVFGA      716
H44/76   FNNDGKSLGITEDTENEAEAEVENEAGVG-------E-QLKP-EAKPQFGVVFGA     732
M990     FNNDGKSLSITENIENEAEAEVEVEAEAEVEVEADVGKQLEPDEVKHKFGVVFGA     744
M981     IDSDRK---------------------------------------IGVVFGA      713
881607   IDSDRK---------------------------------------FGAVFGA      698
         * *                                              *  ****

BNCV     KKDNKEVEK    725
H44/76   KKDNKEVEK    741
M990     KKDMQEVEK    753
M981     KKDMQEVEK    722
881607   KKDDKEATR    707
         ***  *
```

Fig. 13
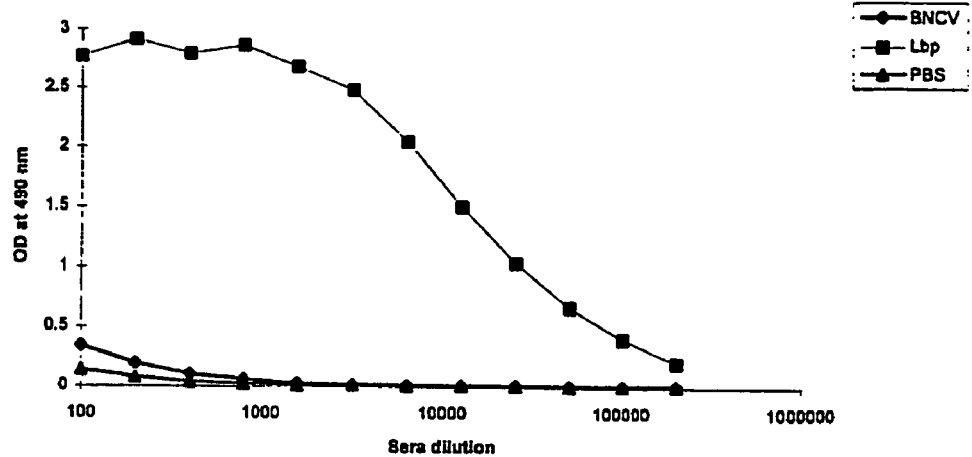
A  a-Lbp response in mice immunized with Lbp or BNCV whole cells
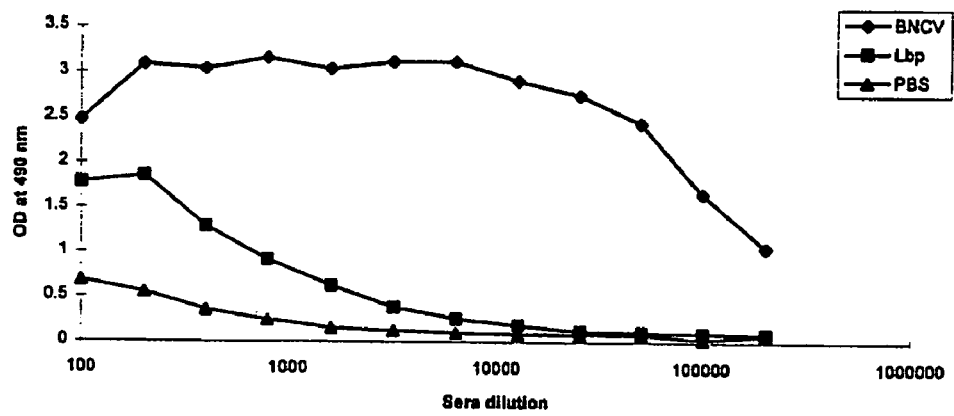
B  BNCV(fe-) whole cell response in mice immunized with Lbp or BNCV whole cells
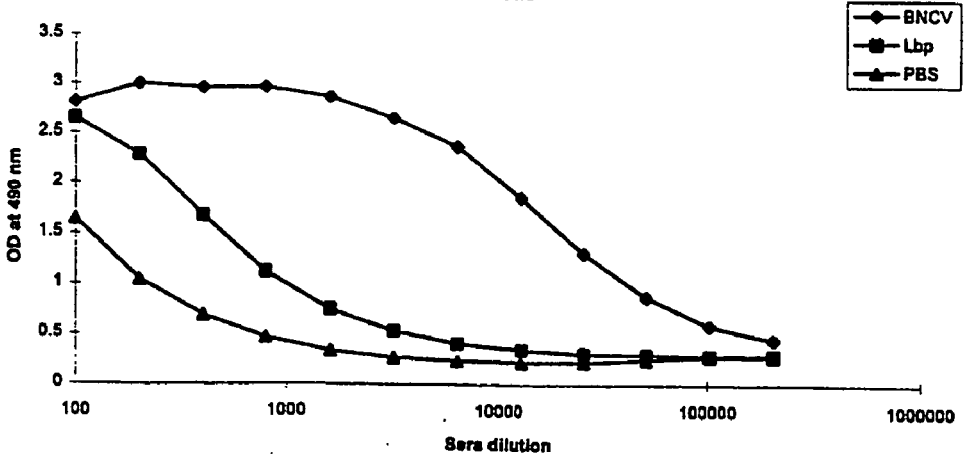
C  H44/76(fe-) whole cell response in mice immunized with Lbp or BNCV whole cells

SEQUENCE LISTING

```
<160> NUMBER OF SEQ ID NOS: 12

<210> SEQ ID NO 1
<211> LENGTH: 2277
<212> TYPE: DNA
<213> ORGANISM: Neisseria meningitidis strain BNCV
<220> FEATURE:
<221> NAME/KEY: CDS
<222> LOCATION: (100)...(2274)

<400> SEQUENCE: 1
tcctgatttt tgttaattca ctataaaaac gggttgatat tatctgtaca tattaatata      60
atgataatta ttattaatca aataggagga aaagtaggg atg tgt aaa ccg aat        114
                                           Met Cys Lys Pro Asn
                                            1               5
tat ggc ggc att gtc ttg ttg ccc tta ctt ttg gca tct tgt atc ggc       162
Tyr Gly Gly Ile Val Leu Leu Pro Leu Leu Leu Ala Ser Cys Ile Gly
                10                  15                  20
ggc aat ttc ggc gtg cag cct gtt gtc gaa tca acg ccg acc gcg tac       210
Gly Asn Phe Gly Val Gln Pro Val Val Glu Ser Thr Pro Thr Ala Tyr
            25                  30                  35
ccc gtc act ttc aag tct aag gac gtt ccc act ccg ccc cct gcc aaa       258
Pro Val Thr Phe Lys Ser Lys Asp Val Pro Thr Pro Pro Pro Ala Lys
        40                  45                  50
cct tct ata gaa atc acg ccg gtc aac cgg ccc gcc gtc ggt gcg gca       306
Pro Ser Ile Glu Ile Thr Pro Val Asn Arg Pro Ala Val Gly Ala Ala
    55                  60                  65
atg cgg ctg cca agg cgg aat act gct ttt cat cgt gaa gat ggc acg       354
Met Arg Leu Pro Arg Arg Asn Thr Ala Phe His Arg Glu Asp Gly Thr
 70                  75                  80                  85
gaa att cca aat agc aaa caa gca gaa gaa aag ctg tcg ttt caa gaa       402
Glu Ile Pro Asn Ser Lys Gln Ala Glu Glu Lys Leu Ser Phe Gln Glu
                90                  95                 100
ggt gat gtt ctg ttt tta tac ggt tca aaa gga aat aaa ctt caa caa       450
Gly Asp Val Leu Phe Leu Tyr Gly Ser Lys Gly Asn Lys Leu Gln Gln
            105                 110                 115

```
ctt aaa agc gaa att cat aaa cgt gat tcc gat gta gaa att agg aca      498
Leu Lys Ser Glu Ile His Lys Arg Asp Ser Asp Val Glu Ile Arg Thr
        120                 125                 130 tca gaa aag gaa aat aaa aaa tat gat tat aaa ttt gta gat gca ggt      546
Ser Glu Lys Glu Asn Lys Lys Tyr Asp Tyr Lys Phe Val Asp Ala Gly
135                 140                 145 tat gta tat gta aag gga aaa gat gaa att aag tgg act tca gat tac      594
Tyr Val Tyr Val Lys Gly Lys Asp Glu Ile Lys Trp Thr Ser Asp Tyr
150                 155                 160                 165 aag cag ttt tcc aac cgc tta ggt tat gac ggt ttt gta tat tat tcc      642
Lys Gln Phe Ser Asn Arg Leu Gly Tyr Asp Gly Phe Val Tyr Tyr Ser
                170                 175                 180 gga gaa cgt cct tcc caa tct tta ccg agt gcg gga acg gtg gaa tat      690
Gly Glu Arg Pro Ser Gln Ser Leu Pro Ser Ala Gly Thr Val Glu Tyr
            185                 190                 195 tct ggt aac tgg caa tat atg acc gat gcc aaa cgt cat cga gca ggt      738
Ser Gly Asn Trp Gln Tyr Met Thr Asp Ala Lys Arg His Arg Ala Gly
        200                 205                 210 aag gcg gtt ggc att gac aat ttg ggt tat tac aca ttt tat ggt aac      786
Lys Ala Val Gly Ile Asp Asn Leu Gly Tyr Tyr Thr Phe Tyr Gly Asn
215                 220                 225 gat gtt ggt gca act tct tat gcg gct aag gat gtc gac gaa agg gaa      834
Asp Val Gly Ala Thr Ser Tyr Ala Ala Lys Asp Val Asp Glu Arg Glu
230                 235                 240                 245 aaa cat cct gct aaa tat acg gta gat ttc ggt aac aaa acc ctg acg      882
Lys His Pro Ala Lys Tyr Thr Val Asp Phe Gly Asn Lys Thr Leu Thr
                250                 255                 260 ggc gag ctg att aaa aac caa tat gtc aaa ccc agt gag aag caa aaa      930
Gly Glu Leu Ile Lys Asn Gln Tyr Val Lys Pro Ser Glu Lys Gln Lys
            265                 270                 275 ccg ctg acc att tac aac atc act gcc gat tta aac ggc aac cgc ttt      978
Pro Leu Thr Ile Tyr Asn Ile Thr Ala Asp Leu Asn Gly Asn Arg Phe
        280                 285                 290 acc ggc agt gcc aag gtc aat cct gat tta gcg aaa agc cat gcc aat     1026
Thr Gly Ser Ala Lys Val Asn Pro Asp Leu Ala Lys Ser His Ala Asn
295                 300                 305 aag gag cat ttg ttt ttc cat gcc gat gcc gat cag cgg ctt gag ggc     1074
Lys Glu His Leu Phe Phe His Ala Asp Ala Asp Gln Arg Leu Glu Gly
310                 315                 320                 325 ggt ttt ttc ggc gat aag ggg gaa gag ctt gcc gga cgg ttt atc agc     1122
Gly Phe Phe Gly Asp Lys Gly Glu Glu Leu Ala Gly Arg Phe Ile Ser
                330                 335                 340 aac gac aac agc gta ttc ggt gta ttc gca ggc aaa caa aat agc ccc     1170
Asn Asp Asn Ser Val Phe Gly Val Phe Ala Gly Lys Gln Asn Ser Pro
            345                 350                 355 gtg ccg tct gga aaa cac acc aaa atc ttg gat tct ctg aaa att tcc     1218
Val Pro Ser Gly Lys His Thr Lys Ile Leu Asp Ser Leu Lys Ile Ser
        360                 365                 370 gtt gat gag gca agt ggt gaa aat ccc cga ccg ttt gcc att tct cct     1266
Val Asp Glu Ala Ser Gly Glu Asn Pro Arg Pro Phe Ala Ile Ser Pro
375                 380                 385 atg ccc gat ttt ggt cat ccc gac aaa ctt ctt gtc gaa ggg cat gaa     1314
Met Pro Asp Phe Gly His Pro Asp Lys Leu Leu Val Glu Gly His Glu
390                 395                 400                 405 att cct ttg gtt agc caa gag aaa acc atc gag ctt gcc gac ggc agg     1362
Ile Pro Leu Val Ser Gln Glu Lys Thr Ile Glu Leu Ala Asp Gly Arg
                410                 415                 420 aaa atg acc gtc agt gct tgt tgc gac ttt ttg acc tat gtg aaa ctc     1410
Lys Met Thr Val Ser Ala Cys Cys Asp Phe Leu Thr Tyr Val Lys Leu
            425                 430                 435
```

```
gga cgg ata aaa acc gaa cgc ccc gcc gcc aaa ccg aag gcg cag gac      1458
Gly Arg Ile Lys Thr Glu Arg Pro Ala Ala Lys Pro Lys Ala Gln Asp
            440                 445                 450 gaa gag gat tcg gac att gat aat ggc gaa gaa agc gaa gac gaa atc      1506
Glu Glu Asp Ser Asp Ile Asp Asn Gly Glu Glu Ser Glu Asp Glu Ile
        455                 460                 465 ggc gat gaa gaa gaa ggc acc gaa gat gca gcc gca gga gat gaa ggc      1554
Gly Asp Glu Glu Glu Gly Thr Glu Asp Ala Ala Ala Gly Asp Glu Gly
470                 475                 480                 485 agc gaa gaa gac gaa gcc aca gaa aac gaa gac ggc gaa gaa gac gaa      1602
Ser Glu Glu Asp Glu Ala Thr Glu Asn Glu Asp Gly Glu Glu Asp Glu
                490                 495                 500 gct gaa gaa cct gaa gaa gaa tcg tcg gca gaa ggc aac ggc agt tca      1650
Ala Glu Glu Pro Glu Glu Glu Ser Ser Ala Glu Gly Asn Gly Ser Ser
            505                 510                 515 aac gcc atc ctg cct gtc ccg gaa gcc tct aaa ggc agg gat atc gac      1698
Asn Ala Ile Leu Pro Val Pro Glu Ala Ser Lys Gly Arg Asp Ile Asp
        520                 525                 530 ctt ttc ctg aaa ggt atc cgc acg gca gaa acg aat att ccg caa act      1746
Leu Phe Leu Lys Gly Ile Arg Thr Ala Glu Thr Asn Ile Pro Gln Thr
535                 540                 545 gga gaa gca cgc tat acc ggc act tgg gaa gcg cgt atc ggc aaa ccc      1794
Gly Glu Ala Arg Tyr Thr Gly Thr Trp Glu Ala Arg Ile Gly Lys Pro
550                 555                 560                 565 att caa tgg gac aat cat gcg gat aaa gaa gcg gca aaa gca gta ttt      1842
Ile Gln Trp Asp Asn His Ala Asp Lys Glu Ala Ala Lys Ala Val Phe
                570                 575                 580 acc gtt gat ttc ggc aag aaa tcg att tcc gga acg ctg acg gag aaa      1890
Thr Val Asp Phe Gly Lys Lys Ser Ile Ser Gly Thr Leu Thr Glu Lys
            585                 590                 595 aac ggt gta gaa cct gct ttc cgt att gaa aac ggc gtg att gag ggc      1938
Asn Gly Val Glu Pro Ala Phe Arg Ile Glu Asn Gly Val Ile Glu Gly
        600                 605                 610 aac ggt ttc cat gcg aca gcg cgc act cgg gat gac ggc atc gac ctt      1986
Asn Gly Phe His Ala Thr Ala Arg Thr Arg Asp Asp Gly Ile Asp Leu
    615                 620                 625 tcc ggg cag ggt tcg acc aaa ccg cag atc ttc aaa gct aat gat ctt      2034
Ser Gly Gln Gly Ser Thr Lys Pro Gln Ile Phe Lys Ala Asn Asp Leu
630                 635                 640                 645 cgt gta gaa gga gga ttt tac ggc ccg aag gcg gag gaa ttg ggc ggt      2082
Arg Val Glu Gly Gly Phe Tyr Gly Pro Lys Ala Glu Glu Leu Gly Gly
                650                 655                 660 att att ttc aat aat gat ggg aaa tct ctt ggt ata act gaa ggt act      2130
Ile Ile Phe Asn Asn Asp Gly Lys Ser Leu Gly Ile Thr Glu Gly Thr
            665                 670                 675 gaa aat aaa gtt gaa gct gat gtt gat gtt gat gtt gat gtt gat gtt      2178
Glu Asn Lys Val Glu Ala Asp Val Asp Val Asp Val Asp Val Asp Val
        680                 685                 690 gat gct gat gct gat gtt gaa cag tta aaa cct gaa gtt aaa ccc caa      2226
Asp Ala Asp Ala Asp Val Glu Gln Leu Lys Pro Glu Val Lys Pro Gln
    695                 700                 705 ttc ggc gtg gta ttc ggt gcg aag aaa gat aat aaa gag gtg gaa aaa      2274
Phe Gly Val Val Phe Gly Ala Lys Lys Asp Asn Lys Glu Val Glu Lys
710                 715                 720                 725 tga                                                                  2277

<210> SEQ ID NO 2
<211> LENGTH: 725
<212> TYPE: PRT
```

<213> ORGANISM: Neisseria meningitidis strain BNCV

<400> SEQUENCE: 2

```
Met Cys L

```
Val Glu Gly His Glu Ile Pro Leu Val Ser Gln Glu Lys Thr Ile Glu
                405                 410                 415
Leu Ala Asp Gly Arg Lys Met Thr Val Ser Ala Cys Cys Asp Phe Leu
            420                 425                 430
Thr Tyr Val Lys Leu Gly Arg Ile Lys Thr Glu Arg Pro Ala Ala Lys
        435                 440                 445
Pro Lys Ala Gln Asp Glu Glu Asp Ser Asp Ile Asp Asn Gly Glu Glu
    450                 455                 460
Ser Glu Asp Glu Ile Gly Asp Glu Glu Gly Thr Glu Asp Ala Ala
465                 470                 475                 480
Ala Gly Asp Glu Gly Ser Glu Glu Asp Glu Ala Thr Glu Asn Glu Asp
                485                 490                 495
Gly Glu Glu Asp Glu Ala Glu Glu Pro Glu Glu Glu Ser Ser Ala Glu
            500                 505                 510
Gly Asn Gly Ser Ser Asn Ala Ile Leu Pro Val Pro Glu Ala Ser Lys
        515                 520                 525
Gly Arg Asp Ile Asp Leu Phe Leu Lys Gly Ile Arg Thr Ala Glu Thr
    530                 535                 540
Asn Ile Pro Gln Thr Gly Glu Ala Arg Tyr Thr Gly Thr Trp Glu Ala
545                 550                 555                 560
Arg Ile Gly Lys Pro Ile Gln Trp Asp Asn His Ala Asp Lys Glu Ala
                565                 570                 575
Ala Lys Ala Val Phe Thr Val Asp Phe Gly Lys Lys Ser Ile Ser Gly
            580                 585                 590
Thr Leu Thr Glu Lys Asn Gly Val Glu Pro Ala Phe Arg Ile Glu Asn
        595                 600                 605
Gly Val Ile Glu Gly Asn Gly Phe His Ala Thr Ala Arg Thr Arg Asp
    610                 615                 620
Asp Gly Ile Asp Leu Ser Gly Gln Gly Ser Thr Lys Pro Gln Ile Phe
625                 630                 635                 640
Lys Ala Asn Asp Leu Arg Val Glu Gly Gly Phe Tyr Gly Pro Lys Ala
                645                 650                 655
Glu Glu Leu Gly Gly Ile Ile Phe Asn Asn Asp Gly Lys Ser Leu Gly
            660                 665                 670
Ile Thr Glu Gly Thr Glu Asn Lys Val Glu Ala Asp Val Asp Val Asp
        675                 680                 685
Val Asp Val Asp Val Asp Ala Asp Ala Asp Val Glu Gln Leu Lys Pro
    690                 695                 700
Glu Val Lys Pro Gln Phe Gly Val Val Phe Gly Ala Lys Lys Asp Asn
705                 710                 715                 720
Lys Glu Val Glu Lys
                725

<210> SEQ ID NO 3
<211> LENGTH: 2169
<212> TYPE: DNA
<213> ORGANISM: Neisseria meningitidis strain M981
<220> FEATURE:
<221> NAME/KEY: CDS
<222> LOCATION: (1)...(2166)

<400> SEQUENCE: 3 atg tgt aaa ccg aat tat ggc ggc att gtc ttg ttg ccc tta ctt ttg      48
Met Cys Lys Pro Asn Tyr Gly Gly Ile Val Leu Leu Pro Leu Leu Leu
1               5                   10                  15 gca tct tgc atc ggc ggc aat ttc ggc gtg cag cct gtt gtc gaa tca      96
```

```
Ala Ser Cys Ile Gly Gly Asn Phe Gly Val Gln Pro Val Val Glu Ser
         20                  25                  30 acg ccg acc gcg tac ccc gtc act ttc aag tct aag gac gtt ccc act     144
Thr Pro Thr Ala Tyr Pro Val Thr Phe Lys Ser Lys Asp Val Pro Thr
         35                  40                  45 tcg ccc cct gcc ggg tct tcg gta gaa acc acg ccg gtc aac cag ccc     192
Ser Pro Pro Ala Gly Ser Ser Val Glu Thr Thr Pro Val Asn Gln Pro
 50                  55                  60 gcc gtc ggt gcg gca atg cgg ctg ttg aga cgg aat act gct ttt cat     240
Ala Val Gly Ala Ala Met Arg Leu Leu Arg Arg Asn Thr Ala Phe His
 65                  70                  75                  80 cgt gaa gat ggc acg gca att ccc gat agc aaa caa gca gaa gaa aag     288
Arg Glu Asp Gly Thr Ala Ile Pro Asp Ser Lys Gln Ala Glu Glu Lys
                 85                  90                  95 ctg tcg ttt aaa gaa ggt gat gtt ctg ttt tta tac ggt tca aaa gaa     336
Leu Ser Phe Lys Glu Gly Asp Val Leu Phe Leu Tyr Gly Ser Lys Glu
             100                 105                 110 aat aaa ctt caa caa ctt aaa agc gaa att cat aaa cgt aat cct gag     384
Asn Lys Leu Gln Gln Leu Lys Ser Glu Ile His Lys Arg Asn Pro Glu
         115                 120                 125 gca agc att acc aca tcg gaa aat gaa aat aaa aaa tat aat tat cgg     432
Ala Ser Ile Thr Thr Ser Glu Asn Glu Asn Lys Lys Tyr Asn Tyr Arg
 130                 135                 140 ttt gtc agt gcc ggt tat gtg ttt act aaa aac gga aaa gat gaa att     480
Phe Val Ser Ala Gly Tyr Val Phe Thr Lys Asn Gly Lys Asp Glu Ile
145                 150                 155                 160 gag aaa aca tcg gat gaa aag cag ttt tct aat cgt tta ggc tat gac     528
Glu Lys Thr Ser Asp Glu Lys Gln Phe Ser Asn Arg Leu Gly Tyr Asp
                165                 170                 175 ggt ttt gta tat tat ctc gga gaa cat cct tcc caa tct tta ccg agc     576
Gly Phe Val Tyr Tyr Leu Gly Glu His Pro Ser Gln Ser Leu Pro Ser
            180                 185                 190 gcg gga acg gtg aaa tat tcc ggc aac tgg caa tat atg acc gat gcc     624
Ala Gly Thr Val Lys Tyr Ser Gly Asn Trp Gln Tyr Met Thr Asp Ala
        195                 200                 205 ata cgt cat cgg aga ggt aag ggg gtt tcc agt gtg gat ttg ggt tat     672
Ile Arg His Arg Arg Gly Lys Gly Val Ser Ser Val Asp Leu Gly Tyr
    210                 215                 220 acc aca tat tat ggt aat gaa att ggg gca gct tct tat gag gct agg     720
Thr Thr Tyr Tyr Gly Asn Glu Ile Gly Ala Ala Ser Tyr Glu Ala Arg
225                 230                 235                 240 gat gcc gat ggc cgg gaa aaa cat cct gcc gaa tat acg gtt aat ttc     768
Asp Ala Asp Gly Arg Glu Lys His Pro Ala Glu Tyr Thr Val Asn Phe
                245                 250                 255 gac aaa aaa aac ctg gaa ggt aag ttg att aaa aat cag tat gtg caa     816
Asp Lys Lys Asn Leu Glu Gly Lys Leu Ile Lys Asn Gln Tyr Val Gln
            260                 265                 270 aag aga gat gat cct aaa aat cca ctg acc att tac aac att acc gca     864
Lys Arg Asp Asp Pro Lys Asn Pro Leu Thr Ile Tyr Asn Ile Thr Ala
        275                 280                 285 aca ttg gac ggc aac cgc ttt acc ggc agt gcc aaa gtt agc acc gag     912
Thr Leu Asp Gly Asn Arg Phe Thr Gly Ser Ala Lys Val Ser Thr Glu
    290                 295                 300 gtg aag acg caa cac gct gat aaa gaa tat ttg ttt ttc cat acc gat     960
Val Lys Thr Gln His Ala Asp Lys Glu Tyr Leu Phe Phe His Thr Asp
305                 310                 315                 320 gcc gat cag cgg ctt gag ggc ggt ttt ttc ggc gat aac gga gaa gag    1008
Ala Asp Gln Arg Leu Glu Gly Gly Phe Phe Gly Asp Asn Gly Glu Glu
                325                 330                 335
```

-continued

```
ctt gcc ggg cgg ttt atc agt aac gac aac agc gta ttc ggc gtg ttc        1056
Leu Ala Gly Arg Phe Ile Ser Asn Asp Asn Ser Val Phe Gly Val Phe
        340                 345                 350 gca ggc aaa caa aaa aca gag aca gca aac gca tca gat aca aat cct        1104
Ala Gly Lys Gln Lys Thr Glu Thr Ala Asn Ala Ser Asp Thr Asn Pro
355                 360                 365 gcc ctg ccg tct gga aaa cac acc aaa atc ttg gat tct cta aaa att        1152
Ala Leu Pro Ser Gly Lys His Thr Lys Ile Leu Asp Ser Leu Lys Ile
    370                 375                 380 tcc gtt gac gag gcg act gat gac cat gcc cgt aag ttt gcc att tcc        1200
Ser Val Asp Glu Ala Thr Asp Asp His Ala Arg Lys Phe Ala Ile Ser
385                 390                 395                 400 act atg ccc gat ttt ggt cat ccc gac aaa ctt ctt gtc gaa ggg cgt        1248
Thr Met Pro Asp Phe Gly His Pro Asp Lys Leu Leu Val Glu Gly Arg
                405                 410                 415 gaa att cct ttg gtt agc caa gag aaa acc atc gag ctt gcc gac ggc        1296
Glu Ile Pro Leu Val Ser Gln Glu Lys Thr Ile Glu Leu Ala Asp Gly
            420                 425                 430 agg aaa atg acc atc cgt gct tgt tgc gat ttt ctg acc tat gtg aaa        1344
Arg Lys Met Thr Ile Arg Ala Cys Cys Asp Phe Leu Thr Tyr Val Lys
        435                 440                 445 ctc gga cgg ata aaa acc gac cgc ccc gcc gtc aaa ccg aag gcg cag        1392
Leu Gly Arg Ile Lys Thr Asp Arg Pro Ala Val Lys Pro Lys Ala Gln
450                 455                 460 gat gaa gag gat tcg gac att gat aat ggc gaa gaa agc gaa gac gaa        1440
Asp Glu Glu Asp Ser Asp Ile Asp Asn Gly Glu Glu Ser Glu Asp Glu
465                 470                 475                 480 att tcc gaa gat gat aac ggc gaa gat gaa gtc acc gaa gaa gag gaa        1488
Ile Ser Glu Asp Asp Asn Gly Glu Asp Glu Val Thr Glu Glu Glu Glu
                485                 490                 495 gct gaa gaa acc gaa gaa gaa act gat gaa gac gaa gag gaa gaa ccc        1536
Ala Glu Glu Thr Glu Glu Glu Thr Asp Glu Asp Glu Glu Glu Glu Pro
            500                 505                 510 gaa gaa act gaa gaa act gaa gaa act gaa gaa act gaa gaa act gaa        1584
Glu Glu Thr Glu Glu Thr Glu Glu Thr Glu Glu Thr Glu Glu Thr Glu
        515                 520                 525 gaa act gaa gaa aaa tcg ccg aca gaa gaa ggc aac ggc ggt tca ggc        1632
Glu Thr Glu Glu Lys Ser Pro Thr Glu Glu Gly Asn Gly Gly Ser Gly
530                 535                 540 agc atc ctg ccc act ccg gaa gcc tct aaa ggc agg gac atc gac ctt        1680
Ser Ile Leu Pro Thr Pro Glu Ala Ser Lys Gly Arg Asp Ile Asp Leu
545                 550                 555                 560 ttc ctg aaa ggt atc cgc acg gcg gaa gcc gac att ccg caa att gga        1728
Phe Leu Lys Gly Ile Arg Thr Ala Glu Ala Asp Ile Pro Gln Ile Gly
                565                 570                 575 aaa gca cgc tat acc ggc act tgg gaa gcg cgt atc ggc gtg ccg gat        1776
Lys Ala Arg Tyr Thr Gly Thr Trp Glu Ala Arg Ile Gly Val Pro Asp
            580                 585                 590 aag aaa ggc gaa cag cta gat ggc act acg tcc att caa aag gat agc        1824
Lys Lys Gly Glu Gln Leu Asp Gly Thr Thr Ser Ile Gln Lys Asp Ser
        595                 600                 605 tat gcg aat caa gcg gca aaa gca gaa ttt gac gtt gat ttt ggt gcg        1872
Tyr Ala Asn Gln Ala Ala Lys Ala Glu Phe Asp Val Asp Phe Gly Ala
610                 615                 620 aag tcg ctt tca ggt aag ttg aca gaa aaa aat gat aca cac ccc gct        1920
Lys Ser Leu Ser Gly Lys Leu Thr Glu Lys Asn Asp Thr His Pro Ala
625                 630                 635                 640 ttt tat att gaa aaa ggt gtg att gat ggc aac ggt ttc cac gct ttg        1968
Phe Tyr Ile Glu Lys Gly Val Ile Asp Gly Asn Gly Phe His Ala Leu
                645                 650                 655
```

```
gcg cgt act cgt gaa aat ggt gtt gat ttg tct ggg caa ggt tcg act        2016
Ala Arg Thr Arg Glu Asn Gly Val Asp Leu Ser Gly Gln Gly Ser Thr
            660                 665                 670 aat ccc caa agt ttt aaa gcc agt aat ctt ctc gta gaa gga gga ttt        2064
Asn Pro Gln Ser Phe Lys Ala Ser Asn Leu Leu Val Glu Gly Gly Phe
        675                 680                 685 tat ggt ccg cag gcg gca gag ttg ggt ggt aat att atc gac agt gac        2112
Tyr Gly Pro Gln Ala Ala Glu Leu Gly Gly Asn Ile Ile Asp Ser Asp
    690                 695                 700 cgg aaa atc ggc gtg gta ttc ggt gcg aag aaa gat atg cag gag gtg        2160
Arg Lys Ile Gly Val Val Phe Gly Ala Lys Lys Asp Met Gln Glu Val
705                 710                 715                 720 gaa aaa tga                                                             2169
Glu Lys <210> SEQ ID NO 4
<211> LENGTH: 722
<212> TYPE: PRT
<213> ORGANISM: Neisseria meningitidis strain M981

<400> SEQUENCE: 4

Met Cys Lys Pro Asn Tyr Gly Gly Ile Val Leu Leu Pro Leu Leu Leu
 1               5                  10                  15

Ala Ser Cys Ile Gly Gly Asn Phe Gly Val Gln Pro Val Val Glu Ser
            20                  25                  30

Thr Pro Thr Ala Tyr Pro Val Thr Phe Lys Ser Lys Asp Val Pro Thr
        35                  40                  45

Ser Pro Pro Ala Gly Ser Ser Val Glu Thr Thr Pro Val Asn Gln Pro
    50                  55                  60

Ala Val Gly Ala Ala Met Arg Leu Leu Arg Arg Asn Thr Ala Phe His
65                  70                  75                  80

Arg Glu Asp Gly Thr Ala Ile Pro Asp Ser Lys Gln Ala Glu Glu Lys
                85                  90                  95

Leu Ser Phe Lys Glu Gly Asp Val Leu Phe Leu Tyr Gly Ser Lys Glu
            100                 105                 110

Asn Lys Leu Gln Gln Leu Lys Ser Glu Ile His Lys Arg Asn Pro Glu
        115                 120                 125

Ala Ser Ile Thr Thr Ser Glu Asn Glu Lys Lys Tyr Asn Tyr Arg
    130                 135                 140

Phe Val Ser Ala Gly Tyr Val Phe Thr Lys Asn Gly Lys Asp Glu Ile
145                 150                 155                 160

Glu Lys Thr Ser Asp Glu Lys Gln Phe Ser Asn Arg Leu Gly Tyr Asp
                165                 170                 175

Gly Phe Val Tyr Tyr Leu Gly Glu His Pro Ser Gln Ser Leu Pro Ser
            180                 185                 190

Ala Gly Thr Val Lys Tyr Ser Gly Asn Trp Gln Tyr Met Thr Asp Ala
        195                 200                 205

Ile Arg His Arg Arg Gly Lys Gly Val Ser Ser Val Asp Leu Gly Tyr
    210                 215                 220

Thr Thr Tyr Tyr Gly Asn Glu Ile Gly Ala Ala Ser Tyr Glu Ala Arg
225                 230                 235                 240

Asp Ala Asp Gly Arg Glu Lys His Pro Ala Glu Tyr Thr Val Asn Phe
                245                 250                 255

Asp Lys Lys Asn Leu Glu Gly Lys Leu Ile Lys Asn Gln Tyr Val Gln
            260                 265                 270
```

```
Lys Arg Asp Asp Pro Lys Asn Pro Leu Thr Ile Tyr Asn Ile Thr Ala
        275                 280                 285

Thr Leu Asp Gly Asn Arg Phe Thr Gly Ser Ala Lys Val Ser Thr Glu
        290                 295                 300

Val Lys Thr Gln His Ala Asp Lys Glu Tyr Leu Phe Phe His Thr Asp
305                 310                 315                 320

Ala Asp Gln Arg Leu Glu Gly Gly Phe Phe Gly Asp Asn Gly Glu Glu
                325                 330                 335

Leu Ala Gly Arg Phe Ile Ser Asn Asp Asn Ser Val Phe Gly Val Phe
                340                 345                 350

Ala Gly Lys Gln Lys Thr Glu Thr Ala Asn Ala Ser Asp Thr Asn Pro
                355                 360                 365

Ala Leu Pro Ser Gly Lys His Thr Lys Ile Leu Asp Ser Leu Lys Ile
        370                 375                 380

Ser Val Asp Glu Ala Thr Asp His Ala Arg Lys Phe Ala Ile Ser
385                 390                 395                 400

Thr Met Pro Asp Phe Gly His Pro Asp Lys Leu Leu Val Glu Gly Arg
                405                 410                 415

Glu Ile Pro Leu Val Ser Gln Glu Lys Thr Ile Glu Leu Ala Asp Gly
                420                 425                 430

Arg Lys Met Thr Ile Arg Ala Cys Cys Asp Phe Leu Thr Tyr Val Lys
        435                 440                 445

Leu Gly Arg Ile Lys Thr Asp Arg Pro Ala Val Lys Pro Lys Ala Gln
        450                 455                 460

Asp Glu Glu Asp Ser Asp Ile Asp Asn Gly Glu Glu Ser Glu Asp Glu
465                 470                 475                 480

Ile Ser Glu Asp Asp Asn Gly Glu Asp Glu Val Thr Glu Glu Glu Glu
                485                 490                 495

Ala Glu Glu Thr Glu Glu Thr Asp Glu Asp Glu Glu Glu Pro
                500                 505                 510

Glu Glu Thr Glu Glu Thr Glu Glu Thr Glu Glu Thr Glu Glu Thr Glu
        515                 520                 525

Glu Thr Glu Glu Lys Ser Pro Thr Glu Glu Gly Asn Gly Gly Ser Gly
        530                 535                 540

Ser Ile Leu Pro Thr Pro Glu Ala Ser Lys Gly Arg Asp Ile Asp Leu
545                 550                 555                 560

Phe Leu Lys Gly Ile Arg Thr Ala Glu Ala Asp Ile Pro Gln Ile Gly
                565                 570                 575

Lys Ala Arg Tyr Thr Gly Thr Trp Glu Ala Arg Ile Gly Val Pro Asp
                580                 585                 590

Lys Lys Gly Glu Gln Leu Asp Gly Thr Thr Ser Ile Gln Lys Asp Ser
                595                 600                 605

Tyr Ala Asn Gln Ala Ala Lys Ala Glu Phe Asp Val Asp Phe Gly Ala
        610                 615                 620

Lys Ser Leu Ser Gly Lys Leu Thr Glu Lys Asn Asp Thr His Pro Ala
625                 630                 635                 640

Phe Tyr Ile Glu Lys Gly Val Ile Asp Gly Asn Gly Phe His Ala Leu
                645                 650                 655

Ala Arg Thr Arg Glu Asn Gly Val Asp Leu Ser Gly Gln Gly Ser Thr
                660                 665                 670

Asn Pro Gln Ser Phe Lys Ala Ser Asn Leu Leu Val Glu Gly Gly Phe
        675                 680                 685

Tyr Gly Pro Gln Ala Ala Glu Leu Gly Gly Asn Ile Ile Asp Ser Asp
```

```
                690              695             700
     Arg Lys Ile Gly Val Val Phe Gly Ala Lys Lys Asp Met Gln Glu Val
     705                 710                 715                 720

Glu Lys

<210> SEQ ID NO 5
<211> LENGTH: 2226
<212> TYPE: DNA
<213> ORGANISM: Neisseria meningitidis strain H44/76
<220> FEATURE:
<221> NAME/KEY: CDS
<222> LOCATION: (1)...(2223)

<400> SEQUENCE: 5 atg tgt aaa ccg aat tat ggc ggc att gtc ttg ttg ccc tta ctt ttg      48
Met Cys Lys Pro Asn Tyr Gly Gly Ile Val Leu Leu Pro Leu Leu Leu
 1               5                  10                  15 gca tct tgt att ggc ggc aat ttc ggc gtg cag cct gtt gtc gaa tca      96
Ala Ser Cys Ile Gly Gly Asn Phe Gly Val Gln Pro Val Val Glu Ser
             20                  25                  30 acg ccg acc gcg tac ccc gtc act ttc aag tct aag gac gtt ccc act     144
Thr Pro Thr Ala Tyr Pro Val Thr Phe Lys Ser Lys Asp Val Pro Thr
         35                  40                  45 ccg ccc cct gcc aaa cct tct ata gaa acc acg ccg gtg ccg tca acc     192
Pro Pro Pro Ala Lys Pro Ser Ile Glu Thr Thr Pro Val Pro Ser Thr
     50                  55                  60 ggg cct gcc gtc ggt gcg gca atg cgg ctg ttg agg cgg att ttc gca     240
Gly Pro Ala Val Gly Ala Ala Met Arg Leu Leu Arg Arg Ile Phe Ala
 65                  70                  75                  80 act tct gat aag gtt ggc aat gat ttt cca aat agc aaa caa gca gaa     288
Thr Ser Asp Lys Val Gly Asn Asp Phe Pro Asn Ser Lys Gln Ala Glu
                 85                  90                  95 gaa aag ctg tcg ttt aaa gaa ggt gat gtt ctg ttt tta tac ggt tca     336
Glu Lys Leu Ser Phe Lys Glu Gly Asp Val Leu Phe Leu Tyr Gly Ser
            100                 105                 110 aaa aaa gat aaa ctt cag tgg ctt aag gat aaa att cat caa cgc aat     384
Lys Lys Asp Lys Leu Gln Trp Leu Lys Asp Lys Ile His Gln Arg Asn
        115                 120                 125 cct aat gta gaa att agg aca tca gaa aat gaa aat aaa aaa tat ggt     432
Pro Asn Val Glu Ile Arg Thr Ser Glu Asn Glu Asn Lys Lys Tyr Gly
    130                 135                 140 tat gaa ttt gtg gat gcc ggt tat gta tat act aaa aac gga aca gat     480
Tyr Glu Phe Val Asp Ala Gly Tyr Val Tyr Thr Lys Asn Gly Thr Asp
145                 150                 155                 160 gaa att gag tgg act tca aat cgc aag cag ttt tct aat cgt ttt ggc     528
Glu Ile Glu Trp Thr Ser Asn Arg Lys Gln Phe Ser Asn Arg Phe Gly
                165                 170                 175 tac gac ggt ttt gta tat tat tcc gga gaa cat cct tcc caa tct tta     576
Tyr Asp Gly Phe Val Tyr Tyr Ser Gly Glu His Pro Ser Gln Ser Leu
            180                 185                 190 ccg agc gcg gga acg gtg caa tat tcc ggt aac tgg caa tat atg acc     624
Pro Ser Ala Gly Thr Val Gln Tyr Ser Gly Asn Trp Gln Tyr Met Thr
        195                 200                 205 gat gcc ata cgt cat cga aca gga aaa gca gga gat cct agc gaa gat     672
Asp Ala Ile Arg His Arg Thr Gly Lys Ala Gly Asp Pro Ser Glu Asp
    210                 215                 220 ttg ggt tat ctc gtt tat tac ggt caa aat gtc gga gca act tct tat     720
Leu Gly Tyr Leu Val Tyr Tyr Gly Gln Asn Val Gly Ala Thr Ser Tyr
225                 230                 235                 240 gct gcg act gcc gac gac cgg gag gga aaa cat cct gcc gaa tat acg     768
```

```
                                        -continued

Ala Ala Thr Ala Asp Asp Arg Glu Gly Lys His Pro Ala Glu Tyr Thr
            245                 250                 255 gtt gat ttc gat aag aaa act ttg acg ggt caa tta att aaa aat cag          816
Val Asp Phe Asp Lys Lys Thr Leu Thr Gly Gln Leu Ile Lys Asn Gln
            260                 265                 270 tat gtg caa aag aaa acc gat gaa aag aaa cca ctg acc att tac gac          864
Tyr Val Gln Lys Lys Thr Asp Glu Lys Lys Pro Leu Thr Ile Tyr Asp
            275                 280                 285 att acc gca aca ttg gac ggc aac cgc ttt acc ggc agt gcc aaa gtt          912
Ile Thr Ala Thr Leu Asp Gly Asn Arg Phe Thr Gly Ser Ala Lys Val
            290                 295                 300 aac acc gag ttg aag acg agc cac gct gat aaa gag cat ttg ttt ttc          960
Asn Thr Glu Leu Lys Thr Ser His Ala Asp Lys Glu His Leu Phe Phe
305                 310                 315                 320 cat acc gat gcc gat cag cgg ctt gag ggc ggt ttt ttc ggc gat aag         1008
His Thr Asp Ala Asp Gln Arg Leu Glu Gly Gly Phe Phe Gly Asp Lys
                325                 330                 335 ggg gaa gag ctt gcc gga cgg ttt atc agc aac gac aac agc gta ttc         1056
Gly Glu Glu Leu Ala Gly Arg Phe Ile Ser Asn Asp Asn Ser Val Phe
                340                 345                 350 ggc gta ttc gca ggc aaa aaa aca aac gca tca aac gca gca gat aca         1104
Gly Val Phe Ala Gly Lys Lys Thr Asn Ala Ser Asn Ala Ala Asp Thr
                355                 360                 365 aat cct gct atg ccg tct gaa aaa cac acc aaa atc ttg gat tct ctg         1152
Asn Pro Ala Met Pro Ser Glu Lys His Thr Lys Ile Leu Asp Ser Leu
370                 375                 380 aaa att tcc gtt gac gag gcg acg gat aaa aat gcc cgc ccg ttt gcc         1200
Lys Ile Ser Val Asp Glu Ala Thr Asp Lys Asn Ala Arg Pro Phe Ala
385                 390                 395                 400 att tcc cct ctg ccc gat ttt ggc cat ccc gac aaa ctc ctt gtc gaa         1248
Ile Ser Pro Leu Pro Asp Phe Gly His Pro Asp Lys Leu Leu Val Glu
                405                 410                 415 ggg cgt gaa att cct ttg gtt agc caa gag aaa acc atc gag ctt gcc         1296
Gly Arg Glu Ile Pro Leu Val Ser Gln Glu Lys Thr Ile Glu Leu Ala
                420                 425                 430 gac ggc agg aaa atg acc gtc cgt gct tgt tgc gat ttt ctg acc tat         1344
Asp Gly Arg Lys Met Thr Val Arg Ala Cys Cys Asp Phe Leu Thr Tyr
                435                 440                 445 gtg aaa ctc gga cgg ata aaa act gac cgc cca gca agt aaa cca aag         1392
Val Lys Leu Gly Arg Ile Lys Thr Asp Arg Pro Ala Ser Lys Pro Lys
450                 455                 460 gcg gaa gat aaa ggg aag gat gaa gag gat aca ggc gtt ggt aac gac         1440
Ala Glu Asp Lys Gly Lys Asp Glu Glu Asp Thr Gly Val Gly Asn Asp
465                 470                 475                 480 gaa gaa ggc acg gaa gat gaa gcc gca gaa ggc agc gaa gga ggc gaa         1488
Glu Glu Gly Thr Glu Asp Glu Ala Ala Glu Gly Ser Glu Gly Gly Glu
                485                 490                 495 gac gaa atc ggc gat gaa gga gga ggt gcg gaa gac gaa gcc gca gaa         1536
Asp Glu Ile Gly Asp Glu Gly Gly Gly Ala Glu Asp Glu Ala Ala Glu
                500                 505                 510 aac gaa ggc ggc gaa gaa gac gaa gct gaa gaa cct gaa gaa ccc gaa         1584
Asn Glu Gly Gly Glu Glu Asp Glu Ala Glu Glu Pro Glu Glu Pro Glu
                515                 520                 525 gaa gaa tcg ccg gca gaa ggc ggc ggt ggt ggt tca gac ggc atc ctg         1632
Glu Glu Ser Pro Ala Glu Gly Gly Gly Gly Gly Ser Asp Gly Ile Leu
                530                 535                 540 ccc gct ccg gaa gct cct aaa ggc agg gat atc gac ctt ttc ctg aaa         1680
Pro Ala Pro Glu Ala Pro Lys Gly Arg Asp Ile Asp Leu Phe Leu Lys
545                 550                 555                 560
```

```
ggt atc cgc acg gcg gaa gcc gac att ccg caa act gga aaa gca cgc       1728
Gly Ile Arg Thr Ala Glu Ala Asp Ile Pro Gln Thr Gly Lys Ala Arg
            565                 570                 575 tat acc ggc act tgg gaa gcg cgt atc agc aaa ccc att caa tgg gac       1776
Tyr Thr Gly Thr Trp Glu Ala Arg Ile Ser Lys Pro Ile Gln Trp Asp
        580                 585                 590 aat cat gcg gat aaa aaa gcg gca aaa gca gaa ttt gac gtt gat ttc       1824
Asn His Ala Asp Lys Lys Ala Ala Lys Ala Glu Phe Asp Val Asp Phe
    595                 600                 605 ggc gag aaa tcg att tcc gga acg ctg acg gag aaa aac ggt gta caa       1872
Gly Glu Lys Ser Ile Ser Gly Thr Leu Thr Glu Lys Asn Gly Val Gln
610                 615                 620 cct gct ttc cat att gaa aac ggc gtg att gag ggc aat ggt ttc cac       1920
Pro Ala Phe His Ile Glu Asn Gly Val Ile Glu Gly Asn Gly Phe His
625                 630                 635                 640 gcg aca gcg cgc act cgg gat aac ggc atc aat ctt tcg gga aat gat       1968
Ala Thr Ala Arg Thr Arg Asp Asn Gly Ile Asn Leu Ser Gly Asn Asp
            645                 650                 655 tcg act aat cct cca agt ttc aaa gcc aat aat ctt ctt gta aca ggc       2016
Ser Thr Asn Pro Pro Ser Phe Lys Ala Asn Asn Leu Leu Val Thr Gly
        660                 665                 670 ggc ttt tac ggc ccg cag gcg gag gaa ttg ggc ggt act att ttc aat       2064
Gly Phe Tyr Gly Pro Gln Ala Glu Glu Leu Gly Gly Thr Ile Phe Asn
    675                 680                 685 aat gat ggg aaa tct ctt ggt ata act gaa gat act gaa aat gaa gct       2112
Asn Asp Gly Lys Ser Leu Gly Ile Thr Glu Asp Thr Glu Asn Glu Ala
690                 695                 700 gaa gct gaa gtt gaa aat gaa gct ggt gtt ggc gaa cag tta aaa cct       2160
Glu Ala Glu Val Glu Asn Glu Ala Gly Val Gly Glu Gln Leu Lys Pro
705                 710                 715                 720 gaa gct aaa ccc caa ttc ggc gtg gta ttc ggt gcg aag aaa gat aat       2208
Glu Ala Lys Pro Gln Phe Gly Val Val Phe Gly Ala Lys Lys Asp Asn
            725                 730                 735 aaa gag gtg gaa aaa tga                                                2226
Lys Glu Val Glu Lys
            740

<210> SEQ ID NO 6
<211> LENGTH: 741
<212> TYPE: PRT
<213> ORGANISM: Neisseria meningitidis strain H44/76

<400> SEQUENCE: 6

Met Cys Lys Pro Asn Tyr Gly Gly Ile Val Leu Leu Pro Leu Leu Leu
 1               5                  10                  15

Ala Ser Cys Ile Gly Gly Asn Phe Gly Val Gln Pro Val Val Glu Ser
            20                  25                  30

Thr Pro Thr Ala Tyr Pro Val Thr Phe Lys Ser Lys Asp Val Pro Thr
        35                  40                  45

Pro Pro Pro Ala Lys Pro Ser Ile Glu Thr Thr Pro Val Pro Ser Thr
    50                  55                  60

Gly Pro Ala Val Gly Ala Ala Met Arg Leu Leu Arg Arg Ile Phe Ala
65                  70                  75                  80

Thr Ser Asp Lys Val Gly Asn Asp Phe Pro Asn Ser Lys Gln Ala Glu
                85                  90                  95

Glu Lys Leu Ser Phe Lys Glu Gly Asp Val Leu Phe Leu Tyr Gly Ser
            100                 105                 110

Lys Lys Asp Lys Leu Gln Trp Leu Lys Asp Lys Ile His Gln Arg Asn
        115                 120                 125
```

```
Pro Asn Val Glu Ile Arg Thr Ser Glu Asn Glu Asn Lys Lys Tyr Gly
    130                 135                 140

Tyr Glu Phe Val Asp Ala Gly Tyr Val Tyr Thr Lys Asn Gly Thr Asp
145                 150                 155                 160

Glu Ile Glu Trp Thr Ser Asn Arg Lys Gln Phe Ser Asn Arg Phe Gly
                165                 170                 175

Tyr Asp Gly Phe Val Tyr Ser Gly Glu His Pro Ser Gln Ser Leu
            180                 185                 190

Pro Ser Ala Gly Thr Val Gln Tyr Ser Gly Asn Trp Gln Tyr Met Thr
            195                 200                 205

Asp Ala Ile Arg His Arg Thr Gly Lys Ala Gly Asp Pro Ser Glu Asp
    210                 215                 220

Leu Gly Tyr Leu Val Tyr Gly Gln Asn Val Gly Ala Thr Ser Tyr
225                 230                 235                 240

Ala Ala Thr Ala Asp Asp Arg Glu Gly Lys His Pro Ala Glu Tyr Thr
                245                 250                 255

Val Asp Phe Asp Lys Lys Thr Leu Thr Gly Gln Leu Ile Lys Asn Gln
            260                 265                 270

Tyr Val Gln Lys Lys Thr Asp Glu Lys Lys Pro Leu Thr Ile Tyr Asp
    275                 280                 285

Ile Thr Ala Thr Leu Asp Gly Asn Arg Phe Thr Gly Ser Ala Lys Val
    290                 295                 300

Asn Thr Glu Leu Lys Thr Ser His Ala Asp Lys Glu His Leu Phe Phe
305                 310                 315                 320

His Thr Asp Ala Asp Gln Arg Leu Glu Gly Gly Phe Phe Gly Asp Lys
                325                 330                 335

Gly Glu Glu Leu Ala Gly Arg Phe Ile Ser Asn Asp Asn Ser Val Phe
            340                 345                 350

Gly Val Phe Ala Gly Lys Lys Thr Asn Ala Ser Asn Ala Ala Asp Thr
            355                 360                 365

Asn Pro Ala Met Pro Ser Glu Lys His Thr Lys Ile Leu Asp Ser Leu
370                 375                 380

Lys Ile Ser Val Asp Glu Ala Thr Asp Lys Asn Ala Arg Pro Phe Ala
385                 390                 395                 400

Ile Ser Pro Leu Pro Asp Phe Gly His Pro Asp Lys Leu Leu Val Glu
                405                 410                 415

Gly Arg Glu Ile Pro Leu Val Ser Gln Glu Lys Thr Ile Glu Leu Ala
            420                 425                 430

Asp Gly Arg Lys Met Thr Val Arg Ala Cys Cys Asp Phe Leu Thr Tyr
            435                 440                 445

Val Lys Leu Gly Arg Ile Lys Thr Asp Arg Pro Ala Ser Lys Pro Lys
    450                 455                 460

Ala Glu Asp Lys Gly Lys Asp Glu Glu Asp Thr Gly Val Gly Asn Asp
465                 470                 475                 480

Glu Glu Gly Thr Glu Asp Glu Ala Ala Glu Gly Ser Glu Gly Glu
                485                 490                 495

Asp Glu Ile Gly Asp Glu Gly Gly Ala Glu Asp Glu Ala Ala Glu
            500                 505                 510

Asn Glu Gly Gly Glu Glu Asp Glu Ala Glu Glu Pro Glu Glu Pro Glu
            515                 520                 525

Glu Glu Ser Pro Ala Glu Gly Gly Gly Gly Ser Asp Gly Ile Leu
530                 535                 540
```

| | | | | | | | | | | | | |
|---|---|---|---|---|---|---|---|---|---|---|---|---|
| Pro | Ala | Pro | Glu | Ala | Pro | Lys | Gly | Arg | Asp | Ile | Asp | Leu | Phe | Leu | Lys |
| 545 | | | | 550 | | | | | 555 | | | | | 560 | |

| Gly | Ile | Arg | Thr | Ala | Glu | Ala | Asp | Ile | Pro | Gln | Thr | Gly | Lys | Ala | Arg |
|---|---|---|---|---|---|---|---|---|---|---|---|---|---|---|---|
| | | | | 565 | | | | | 570 | | | | | 575 | |

| Tyr | Thr | Gly | Thr | Trp | Glu | Ala | Arg | Ile | Ser | Lys | Pro | Ile | Gln | Trp | Asp |
|---|---|---|---|---|---|---|---|---|---|---|---|---|---|---|---|
| | | | 580 | | | | | 585 | | | | | 590 | | |

| Asn | His | Ala | Asp | Lys | Lys | Ala | Ala | Lys | Ala | Glu | Phe | Asp | Val | Asp | Phe |
|---|---|---|---|---|---|---|---|---|---|---|---|---|---|---|---|
| | | 595 | | | | | 600 | | | | | 605 | | | |

| Gly | Glu | Lys | Ser | Ile | Ser | Gly | Thr | Leu | Thr | Glu | Lys | Asn | Gly | Val | Gln |
|---|---|---|---|---|---|---|---|---|---|---|---|---|---|---|---|
| | 610 | | | | | 615 | | | | | 620 | | | | |

| Pro | Ala | Phe | His | Ile | Glu | Asn | Gly | Val | Ile | Glu | Gly | Asn | Gly | Phe | His |
|---|---|---|---|---|---|---|---|---|---|---|---|---|---|---|---|
| 625 | | | | | 630 | | | | | 635 | | | | | 640 |

| Ala | Thr | Ala | Arg | Thr | Arg | Asp | Asn | Gly | Ile | Asn | Leu | Ser | Gly | Asn | Asp |
|---|---|---|---|---|---|---|---|---|---|---|---|---|---|---|---|
| | | | | 645 | | | | | 650 | | | | | 655 | |

| Ser | Thr | Asn | Pro | Pro | Ser | Phe | Lys | Ala | Asn | Asn | Leu | Leu | Val | Thr | Gly |
|---|---|---|---|---|---|---|---|---|---|---|---|---|---|---|---|
| | | | 660 | | | | | 665 | | | | | 670 | | |

| Gly | Phe | Tyr | Gly | Pro | Gln | Ala | Glu | Glu | Leu | Gly | Gly | Thr | Ile | Phe | Asn |
|---|---|---|---|---|---|---|---|---|---|---|---|---|---|---|---|
| | | 675 | | | | | 680 | | | | | 685 | | | |

| Asn | Asp | Gly | Lys | Ser | Leu | Gly | Ile | Thr | Glu | Asp | Thr | Glu | Asn | Glu | Ala |
|---|---|---|---|---|---|---|---|---|---|---|---|---|---|---|---|
| | 690 | | | | | 695 | | | | | 700 | | | | |

| Glu | Ala | Glu | Val | Glu | Asn | Glu | Ala | Gly | Val | Gly | Glu | Gln | Leu | Lys | Pro |
|---|---|---|---|---|---|---|---|---|---|---|---|---|---|---|---|
| 705 | | | | | 710 | | | | | 715 | | | | | 720 |

| Glu | Ala | Lys | Pro | Gln | Phe | Gly | Val | Val | Phe | Gly | Ala | Lys | Lys | Asp | Asn |
|---|---|---|---|---|---|---|---|---|---|---|---|---|---|---|---|
| | | | | 725 | | | | | 730 | | | | | 735 | |

| Lys | Glu | Val | Glu | Lys |
|---|---|---|---|---|
| | | | 740 | |

```
<210> SEQ ID NO 7
<211> LENGTH: 2262
<212> TYPE: DNA
<213> ORGANISM: Neisseria meningitidis strain M990
<220> FEATURE:
<221> NAME/KEY: CDS
<222> LOCATION: (1)...(2259)

<400> SEQUENCE: 7
```

```
                Gly Thr Pro Lys Glu Gln Ala Asp Lys Leu Lys Lys Glu Ile Asn Gly
                        115                 120                 125 cgg cat cct aat gca cca atc tac acg tcc gat tta aaa gat gat gcg              432
Arg His Pro Asn Ala Pro Ile Tyr Thr Ser Asp Leu Lys Asp Asp Ala
        130                 135                 140 tat caa tat aaa tat gtc cgg gcc gga tat gtt tat act aga tat gga              480
Tyr Gln Tyr Lys Tyr Val Arg Ala Gly Tyr Val Tyr Thr Arg Tyr Gly
145                 150                 155                 160 aca gat gaa atc gaa cag aac tca ggc ggt aag cgg gtt acc cac cgc              528
Thr Asp Glu Ile Glu Gln Asn Ser Gly Gly Lys Arg Val Thr His Arg
                165                 170                 175 tta ggt tat gac ggt ttt gta tat tat tcc gga gaa cgt cct tcc caa              576
Leu Gly Tyr Asp Gly Phe Val Tyr Tyr Ser Gly Glu Arg Pro Ser Gln
            180                 185                 190 tct tta ccg agt gcg gga acg gtg gaa tat tct ggt aac tgg caa tat              624
Ser Leu Pro Ser Ala Gly Thr Val Glu Tyr Ser Gly Asn Trp Gln Tyr
        195                 200                 205 atg acc gat gcc aaa cgt cat cga gca ggt cag gcg gtt ggc att gac              672
Met Thr Asp Ala Lys Arg His Arg Ala Gly Gln Ala Val Gly Ile Asp
    210                 215                 220 aat ttg ggt tat atc aca ttt tat ggt aac gat gtt ggt gca act tct              720
Asn Leu Gly Tyr Ile Thr Phe Tyr Gly Asn Asp Val Gly Ala Thr Ser
225                 230                 235                 240 tat gcg gct aag gat gtc gac gaa agg gaa aag cat cct gcc aaa tat              768
Tyr Ala Ala Lys Asp Val Asp Glu Arg Glu Lys His Pro Ala Lys Tyr
                245                 250                 255 acg gtt gat ttt gat aac aaa acc atg aat ggc aag ctg att aaa aat              816
Thr Val Asp Phe Asp Asn Lys Thr Met Asn Gly Lys Leu Ile Lys Asn
            260                 265                 270 cag tat gtg cga aat aaa aaa gat gaa ccc aaa aaa ccg ctg acc att              864
Gln Tyr Val Arg Asn Lys Lys Asp Glu Pro Lys Lys Pro Leu Thr Ile
        275                 280                 285 tac gac att act gca aaa ttg gac ggc aac cgc ttt acc ggc agt gcc              912
Tyr Asp Ile Thr Ala Lys Leu Asp Gly Asn Arg Phe Thr Gly Ser Ala
    290                 295                 300 aag gtc aat cct gat tta gcg aaa aac ctt gcc ggt aat gag cgt ttg              960
Lys Val Asn Pro Asp Leu Ala Lys Asn Leu Ala Gly Asn Glu Arg Leu
305                 310                 315                 320 ttt ttc cat gcc gat gcc gat cag cgg ctt gag ggc ggt ttt ttc ggc             1008
Phe Phe His Ala Asp Ala Asp Gln Arg Leu Glu Gly Gly Phe Phe Gly
                325                 330                 335 gat aac gga gaa gag ctt gcc gga cgg ttt atc agc aac gac aac agc             1056
Asp Asn Gly Glu Glu Leu Ala Gly Arg Phe Ile Ser Asn Asp Asn Ser
            340                 345                 350 gta ttc ggc gta ttc gca ggc aaa aaa aca gag aca gca aac gca gca             1104
Val Phe Gly Val Phe Ala Gly Lys Lys Thr Glu Thr Ala Asn Ala Ala
        355                 360                 365 gat aca aaa cct gcc ctg ccg tct gga aaa cac acc aaa atc ttg gat             1152
Asp Thr Lys Pro Ala Leu Pro Ser Gly Lys His Thr Lys Ile Leu Asp
    370                 375                 380 tct cta aaa att tcc gtt gac gag gcg act gat ggc cat gcc cgt aag             1200
Ser Leu Lys Ile Ser Val Asp Glu Ala Thr Asp Gly His Ala Arg Lys
385                 390                 395                 400 ttt gcc att tcc tct atg ccc gat ttt ggt cat ccc gac aaa ctt ctt             1248
Phe Ala Ile Ser Ser Met Pro Asp Phe Gly His Pro Asp Lys Leu Leu
                405                 410                 415 gtc gaa ggg cgt gaa att cct ttg gta aac gaa gaa caa atc atc aag             1296
Val Glu Gly Arg Glu Ile Pro Leu Val Asn Glu Glu Gln Ile Ile Lys
            420                 425                 430
```

```
ctt gcc gac ggc agg aaa atg acc gtc cgt gct tgt tgc gac ttt ttg      1344
Leu Ala Asp Gly Arg Lys Met Thr Val Arg Ala Cys Cys Asp Phe Leu
        435                 440                 445 acc tat gtg aaa ctc gga cgg ata aaa acc gat cgc ccg gca agt aaa      1392
Thr Tyr Val Lys Leu Gly Arg Ile Lys Thr Asp Arg Pro Ala Ser Lys
450                 455                 460 cca aag gcg gaa gat aaa ggg gag gat gaa gag ggt gca ggc gtt gat      1440
Pro Lys Ala Glu Asp Lys Gly Glu Asp Glu Glu Gly Ala Gly Val Asp
465                 470                 475                 480 aac gac gaa gaa agc gaa gac gaa gcc gta gaa gac gaa ggc ggc gaa      1488
Asn Asp Glu Glu Ser Glu Asp Glu Ala Val Glu Asp Glu Gly Gly Glu
                485                 490                 495 gaa gac gaa act tcc gaa gag gat aat ggc gaa gac gaa gaa gca acc      1536
Glu Asp Glu Thr Ser Glu Glu Asp Asn Gly Glu Asp Glu Glu Ala Thr
                500                 505                 510 gcc gaa gaa gaa acc gaa gaa gtt gat gaa gcc gaa gag gag gaa gtt      1584
Ala Glu Glu Glu Thr Glu Glu Val Asp Glu Ala Glu Glu Glu Glu Val
        515                 520                 525 gaa gaa ccc gaa gaa aaa tcg ccg gca gaa ggc aac ggc ggt tca ggc      1632
Glu Glu Pro Glu Glu Lys Ser Pro Ala Glu Gly Asn Gly Gly Ser Gly
530                 535                 540 agc atc ctg cct gcc cta gaa gcc tct aaa ggc agg gac atc gac ctt      1680
Ser Ile Leu Pro Ala Leu Glu Ala Ser Lys Gly Arg Asp Ile Asp Leu
545                 550                 555                 560 ttc ctg aaa ggt atc cgc acg gca gaa acg gat att ccg caa agc gga      1728
Phe Leu Lys Gly Ile Arg Thr Ala Glu Thr Asp Ile Pro Gln Ser Gly
                565                 570                 575 acg gcg cat tat acc ggc act tgg gaa gcg cgt atc ggc aaa ccc att      1776
Thr Ala His Tyr Thr Gly Thr Trp Glu Ala Arg Ile Gly Lys Pro Ile
                580                 585                 590 caa tgg gac aat cag gcg gat gaa aaa gcg gca aaa gca gaa ttt acc      1824
Gln Trp Asp Asn Gln Ala Asp Glu Lys Ala Ala Lys Ala Glu Phe Thr
        595                 600                 605 gtt gat ttc gac aag aaa tcg att tcc gga aag ctg acg gag caa aac      1872
Val Asp Phe Asp Lys Lys Ser Ile Ser Gly Lys Leu Thr Glu Gln Asn
610                 615                 620 ggc gta gaa cct gct ttc cat att gaa gac ggc aag att gat ggc aac      1920
Gly Val Glu Pro Ala Phe His Ile Glu Asp Gly Lys Ile Asp Gly Asn
625                 630                 635                 640 ggt ttc cac gcg aca gcg cgc act cgg gag agc ggc atc aat ctt tcg      1968
Gly Phe His Ala Thr Ala Arg Thr Arg Glu Ser Gly Ile Asn Leu Ser
                645                 650                 655 gga aat ggt tcg acc gac ccc aaa aca ttc caa gct agt aat ctt cgt      2016
Gly Asn Gly Ser Thr Asp Pro Lys Thr Phe Gln Ala Ser Asn Leu Arg
                660                 665                 670 gta gaa gga gga ttt tac ggc ccg cag gcg gcg gaa ttg ggc ggt act      2064
Val Glu Gly Gly Phe Tyr Gly Pro Gln Ala Ala Glu Leu Gly Gly Thr
        675                 680                 685 att ttc aat aat gat ggg aaa tct ctt agt ata act gaa aat att gaa      2112
Ile Phe Asn Asn Asp Gly Lys Ser Leu Ser Ile Thr Glu Asn Ile Glu
690                 695                 700 aat gaa gct gaa gct gaa gtt gaa gtt gaa gct gaa gct gaa gtt gaa      2160
Asn Glu Ala Glu Ala Glu Val Glu Val Glu Ala Glu Ala Glu Val Glu
705                 710                 715                 720 gtt gaa gct gat gtt ggc aaa cag tta gaa cct gat gaa gtt aaa cac      2208
Val Glu Ala Asp Val Gly Lys Gln Leu Glu Pro Asp Glu Val Lys His
                725                 730                 735 aaa ttc ggc gtg gta ttc ggt gcg aag aaa gat atg cag gag gtg gaa      2256
Lys Phe Gly Val Val Phe Gly Ala Lys Lys Asp Met Gln Glu Val Glu
                740                 745                 750
```

```
                      aaa tga                                                 2262
                      Lys <210> SEQ ID NO 8
<211> LENGTH: 753
<212> TYPE: PRT
<213> ORGANISM: Neisseria meningitidis strain M990

<400> SEQUENCE: 8

Met Cys Lys Pro Asn Tyr Gly Gly Ile Val Leu Pro Leu Leu Leu
  1               5                  10                  15

Ala Ser Cys Ile Gly Gly Asn Phe Gly Val Gln Pro Val Val Glu Ser
                 20                  25                  30

Thr Pro Thr Ala Pro Thr Leu Ser Asp Ser Lys Ser Ser Asn Pro Ala
             35                  40                  45

Asp Lys Pro Ala Pro Ala Pro Ala Glu Pro Ser Val Glu Ile Thr Pro
 50                  55                  60

Val Lys Arg Pro Ala Val Gly Ala Ala Met Arg Leu Pro Arg Arg Asn
 65                  70                  75                  80

Ile Ala Thr Phe Asp Lys Asn Gly Asn Glu Ile Pro Asn Ser Lys Gln
                 85                  90                  95

Ala Glu Glu Tyr Leu Pro Leu Lys Glu Lys Asp Ile Leu Phe Leu Asp
            100                 105                 110

Gly Thr Pro Lys Glu Gln Ala Asp Lys Leu Lys Lys Glu Ile Asn Gly
            115                 120                 125

Arg His Pro Asn Ala Pro Ile Tyr Thr Ser Asp Leu Lys Asp Asp Ala
            130                 135                 140

Tyr Gln Tyr Lys Tyr Val Arg Ala Gly Tyr Val Tyr Thr Arg Tyr Gly
145                 150                 155                 160

Thr Asp Glu Ile Glu Gln Asn Ser Gly Gly Lys Arg Val Thr His Arg
                165                 170                 175

Leu Gly Tyr Asp Gly Phe Val Tyr Tyr Ser Gly Glu Arg Pro Ser Gln
            180                 185                 190

Ser Leu Pro Ser Ala Gly Thr Val Glu Tyr Ser Gly Asn Trp Gln Tyr
            195                 200                 205

Met Thr Asp Ala Lys Arg His Arg Ala Gly Gln Ala Val Gly Ile Asp
210                 215                 220

Asn Leu Gly Tyr Ile Thr Phe Tyr Gly Asn Asp Val Gly Ala Thr Ser
225                 230                 235                 240

Tyr Ala Ala Lys Asp Val Asp Glu Arg Glu Lys His Pro Ala Lys Tyr
                245                 250                 255

Thr Val Asp Phe Asp Asn Lys Thr Met Asn Gly Lys Leu Ile Lys Asn
            260                 265                 270

Gln Tyr Val Arg Asn Lys Lys Asp Glu Pro Lys Lys Pro Leu Thr Ile
            275                 280                 285

Tyr Asp Ile Thr Ala Lys Leu Asp Gly Asn Arg Phe Thr Gly Ser Ala
            290                 295                 300

Lys Val Asn Pro Asp Leu Ala Lys Asn Leu Ala Gly Asn Glu Arg Leu
305                 310                 315                 320

Phe Phe His Ala Asp Ala Asp Gln Arg Leu Glu Gly Gly Phe Phe Gly
                325                 330                 335

Asp Asn Gly Glu Glu Leu Ala Gly Arg Phe Ile Ser Asn Asp Asn Ser
            340                 345                 350

Val Phe Gly Val Phe Ala Gly Lys Lys Thr Glu Thr Ala Asn Ala Ala
```

```
                355                 360                 365
Asp Thr Lys Pro Ala Leu Pro Ser Gly Lys His Thr Lys Ile Leu Asp
    370                 375                 380

Ser Leu Lys Ile Ser Val Asp Glu Ala Thr Asp Gly His Ala Arg Lys
385                 390                 395                 400

Phe Ala Ile Ser Ser Met Pro Asp Phe Gly His Pro Asp Lys Leu Leu
                405                 410                 415

Val Glu Gly Arg Glu Ile Pro Leu Val Asn Glu Gln Ile Ile Lys
            420                 425                 430

Leu Ala Asp Gly Arg Lys Met Thr Val Arg Ala Cys Cys Asp Phe Leu
        435                 440                 445

Thr Tyr Val Lys Leu Gly Arg Ile Lys Thr Asp Arg Pro Ala Ser Lys
    450                 455                 460

Pro Lys Ala Glu Asp Lys Gly Glu Asp Glu Glu Gly Ala Gly Val Asp
465                 470                 475                 480

Asn Asp Glu Glu Ser Glu Asp Glu Ala Val Glu Asp Glu Gly Gly Glu
                485                 490                 495

Glu Asp Glu Thr Ser Glu Glu Asp Asn Gly Glu Asp Glu Glu Ala Thr
            500                 505                 510

Ala Glu Glu Thr Glu Glu Val Asp Glu Ala Glu Glu Glu Val
        515                 520                 525

Glu Glu Pro Glu Glu Lys Ser Pro Ala Glu Gly Asn Gly Gly Ser Gly
    530                 535                 540

Ser Ile Leu Pro Ala Leu Glu Ala Ser Lys Gly Arg Asp Ile Asp Leu
545                 550                 555                 560

Phe Leu Lys Gly Ile Arg Thr Ala Glu Thr Asp Ile Pro Gln Ser Gly
                565                 570                 575

Thr Ala His Tyr Thr Gly Thr Trp Glu Ala Arg Ile Gly Lys Pro Ile
            580                 585                 590

Gln Trp Asp Asn Gln Ala Asp Glu Lys Ala Ala Lys Ala Glu Phe Thr
        595                 600                 605

Val Asp Phe Asp Lys Lys Ser Ile Ser Gly Lys Leu Thr Glu Gln Asn
    610                 615                 620

Gly Val Glu Pro Ala Phe His Ile Glu Asp Gly Lys Ile Asp Gly Asn
625                 630                 635                 640

Gly Phe His Ala Thr Ala Arg Thr Arg Glu Ser Gly Ile Asn Leu Ser
                645                 650                 655

Gly Asn Gly Ser Thr Asp Pro Lys Thr Phe Gln Ala Ser Asn Leu Arg
            660                 665                 670

Val Glu Gly Gly Phe Tyr Gly Pro Gln Ala Ala Glu Leu Gly Gly Thr
        675                 680                 685

Ile Phe Asn Asn Asp Gly Lys Ser Leu Ser Ile Thr Glu Asn Ile Glu
    690                 695                 700

Asn Glu Ala Glu Ala Glu Val Glu Val Glu Ala Glu Val Glu
705                 710                 715                 720

Val Glu Ala Asp Val Gly Lys Gln Leu Glu Pro Asp Glu Val Lys His
                725                 730                 735

Lys Phe Gly Val Val Phe Gly Ala Lys Lys Asp Met Gln Glu Val Glu
            740                 745                 750

Lys

<210> SEQ ID NO 9
<211> LENGTH: 2124
```

```
<212> TYPE: DNA
<213> ORGANISM: Neisseria meningitidis strain 881607
<220> FEATURE:
<221> NAME/KEY: CDS
<222> LOCATION: (1)...(2121)

<400> SEQUENCE: 9
```

| | | | | | | | | | | | | | | | | |
|---|---|---|---|---|---|---|---|---|---|---|---|---|---|---|---|---|
| atg | tgt | aaa | ccg | aat | tat | ggc | ggc | att | gtc | ttg | ttg | ccc | tta | ctt | ttg | 48 |
| Met | Cys | Lys | Pro | Asn | Tyr | Gly | Gly | Ile | Val | Leu | Leu | Pro | Leu | Leu | Leu | |
| 1 | | | 5 | | | | | 10 | | | | | 15 | | | |
| gca | tct | tgc | atc | ggc | ggc | aat | ttc | ggc | gtg | cag | cct | gtt | gtc | gaa | tca | 96 |
| Ala | Ser | Cys | Ile | Gly | Gly | Asn | Phe | Gly | Val | Gln | Pro | Val | Val | Glu | Ser | |
| | | | 20 | | | | 25 | | | | | 30 | | | | |
| acg | ccg | acc | gcg | tac | ccc | gtc | act | ttc | aag | tct | aag | gac | gtt | ccc | act | 144 |
| Thr | Pro | Thr | Ala | Tyr | Pro | Val | Thr | Phe | Lys | Ser | Lys | Asp | Val | Pro | Thr | |
| | | 35 | | | | 40 | | | | | 45 | | | | | |
| tcg | cct | cct | gcc | ggg | tct | tcg | gta | gaa | acc | acg | ccg | gtc | aac | cga | ccc | 192 |
| Ser | Pro | Pro | Ala | Gly | Ser | Ser | Val | Glu | Thr | Thr | Pro | Val | Asn | Arg | Pro | |
| | 50 | | | | | 55 | | | | | 60 | | | | | |
| gcc | gtt | ggt | gcg | gca | atg | cgg | ctg | ttg | aga | cgg | aat | att | gca | act | tct | 240 |
| Ala | Val | Gly | Ala | Ala | Met | Arg | Leu | Leu | Arg | Arg | Asn | Ile | Ala | Thr | Ser | |
| 65 | | | | | 70 | | | | | 75 | | | | | 80 | |
| gat | aag | gat | ggc | aat | gat | ttt | cca | aat | agc | aaa | caa | gca | gaa | gaa | aag | 288 |
| Asp | Lys | Asp | Gly | Asn | Asp | Phe | Pro | Asn | Ser | Lys | Gln | Ala | Glu | Glu | Lys | |
| | | | | 85 | | | | | 90 | | | | | 95 | | |
| ctg | tcg | ttt | aaa | gag | gaa | gat | atc | ctg | ttt | tta | tac | ggt | tcc | aaa | aaa | 336 |
| Leu | Ser | Phe | Lys | Glu | Glu | Asp | Ile | Leu | Phe | Leu | Tyr | Gly | Ser | Lys | Lys | |
| | | | 100 | | | | | 105 | | | | | 110 | | | |
| gat | caa | cgt | cag | cag | ctt | aaa | gat | aaa | att | cgt | caa | cca | aat | cct | acg | 384 |
| Asp | Gln | Arg | Gln | Gln | Leu | Lys | Asp | Lys | Ile | Arg | Gln | Pro | Asn | Pro | Thr | |
| | | | 115 | | | | | 120 | | | | | 125 | | | |
| gca | agc | att | acc | aca | tcg | gaa | aag | aaa | aat | aaa | aaa | tat | gat | tat | aaa | 432 |
| Ala | Ser | Ile | Thr | Thr | Ser | Glu | Lys | Lys | Asn | Lys | Lys | Tyr | Asp | Tyr | Lys | |
| | 130 | | | | | 135 | | | | | 140 | | | | | |
| ttt | gta | gat | gca | ggt | tat | gta | tat | act | aaa | gac | gga | aaa | gat | gaa | att | 480 |
| Phe | Val | Asp | Ala | Gly | Tyr | Val | Tyr | Thr | Lys | Asp | Gly | Lys | Asp | Glu | Ile | |
| 145 | | | | | 150 | | | | | 155 | | | | | 160 | |
| gag | tgg | act | tca | aat | tac | aag | cag | tct | acc | aac | cgg | ttt | ggt | tat | gac | 528 |
| Glu | Trp | Thr | Ser | Asn | Tyr | Lys | Gln | Ser | Thr | Asn | Arg | Phe | Gly | Tyr | Asp | |
| | | | | 165 | | | | | 170 | | | | | 175 | | |
| ggt | ttt | gta | tat | tat | tcc | gga | gaa | cat | cct | tcg | caa | tct | tta | ccg | agc | 576 |
| Gly | Phe | Val | Tyr | Tyr | Ser | Gly | Glu | His | Pro | Ser | Gln | Ser | Leu | Pro | Ser | |
| | | | 180 | | | | | 185 | | | | | 190 | | | |
| gcg | gga | acg | gtg | aaa | tat | tcc | ggc | aac | tgg | caa | tat | atg | acc | gat | gcc | 624 |
| Ala | Gly | Thr | Val | Lys | Tyr | Ser | Gly | Asn | Trp | Gln | Tyr | Met | Thr | Asp | Ala | |
| | | | 195 | | | | | 200 | | | | | 205 | | | |
| ata | cgt | cat | cga | aca | gga | aaa | gca | gga | gat | cct | agc | gaa | gat | ttg | ggt | 672 |
| Ile | Arg | His | Arg | Thr | Gly | Lys | Ala | Gly | Asp | Pro | Ser | Glu | Asp | Leu | Gly | |
| | 210 | | | | | 215 | | | | | 220 | | | | | |
| tat | atc | gtt | tat | tac | ggt | caa | aat | gtc | gga | gca | act | tct | tat | gct | gcg | 720 |
| Tyr | Ile | Val | Tyr | Tyr | Gly | Gln | Asn | Val | Gly | Ala | Thr | Ser | Tyr | Ala | Ala | |
| 225 | | | | | 230 | | | | | 235 | | | | | 240 | |
| act | gcc | gac | gac | cgg | gag | gga | aaa | cat | cct | gcc | gaa | tat | acg | gtt | aat | 768 |
| Thr | Ala | Asp | Asp | Arg | Glu | Gly | Lys | His | Pro | Ala | Glu | Tyr | Thr | Val | Asn | |
| | | | | 245 | | | | | 250 | | | | | 255 | | |
| ttc | gac | caa | aaa | act | ctg | aat | ggc | aag | ctg | att | aaa | aat | cag | tat | gtg | 816 |
| Phe | Asp | Gln | Lys | Thr | Leu | Asn | Gly | Lys | Leu | Ile | Lys | Asn | Gln | Tyr | Val | |
| | | | 260 | | | | | 265 | | | | | 270 | | | |
| caa | aag | aga | gat | gat | cct | aaa | aaa | cca | ctg | acc | att | tac | gac | att | act | 864 |
| Gln | Lys | Arg | Asp | Asp | Pro | Lys | Lys | Pro | Leu | Thr | Ile | Tyr | Asp | Ile | Thr | |
| | | | 275 | | | | | 280 | | | | | 285 | | | |

-continued

| | |
|---|---|
| gca aaa ttg gac ggc aac cgc ttt acc ggc agt gcc aaa gtt aac aca<br>Ala Lys Leu Asp Gly Asn Arg Phe Thr Gly Ser Ala Lys Val Asn Thr<br>290                       295                    300 | 912 |
| gag gtg aag acg aat cac gct gat aaa gaa tat ttg ttt ttc cat acc<br>Glu Val Lys Thr Asn His Ala Asp Lys Glu Tyr Leu Phe Phe His Thr<br>305                      310                   315                 320 | 960 |
| gat gcc gat cag cgg ctt gag ggc ggt ttt ttc ggc gat aag ggg gaa<br>Asp Ala Asp Gln Arg Leu Glu Gly Gly Phe Phe Gly Asp Lys Gly Glu<br>                 325                    330                   335 | 1008 |
| gag ctt gcc gga cgg ttt atc agc aac gac aac agc gta ttc ggc gtg<br>Glu Leu Ala Gly Arg Phe Ile Ser Asn Asp Asn Ser Val Phe Gly Val<br>        340                          345                    350 | 1056 |
| ttc gca ggc aaa caa aaa aca gag aca gca aac gca tca gat aca aat<br>Phe Ala Gly Lys Gln Lys Thr Glu Thr Ala Asn Ala Ser Asp Thr Asn<br>355                      360                   365 | 1104 |
| cct gcc ctg ccg tct gga aaa cac acc aaa atc ttg gat tct cta aaa<br>Pro Ala Leu Pro Ser Gly Lys His Thr Lys Ile Leu Asp Ser Leu Lys<br>        370                          375                   380 | 1152 |
| att tcc gtt gac gag gca agt ggt gaa aat ccc cga ccg ttt gag gtt<br>Ile Ser Val Asp Glu Ala Ser Gly Glu Asn Pro Arg Pro Phe Glu Val<br>385                      390                   395                 400 | 1200 |
| tcc act atg ccc gat ttt ggt cat ccc gac aaa ctt ctt gtc gaa ggg<br>Ser Thr Met Pro Asp Phe Gly His Pro Asp Lys Leu Leu Val Glu Gly<br>                 405                    410                   415 | 1248 |
| cgt gaa att cct ttg gta aac aaa gaa caa acc atc gat ctt gcc gac<br>Arg Glu Ile Pro Leu Val Asn Lys Glu Gln Thr Ile Asp Leu Ala Asp<br>        420                          425                    430 | 1296 |
| ggc agg aaa atg acc gtc cgt gct tgt tgc gac ttt ttg acc tat gtg<br>Gly Arg Lys Met Thr Val Arg Ala Cys Cys Asp Phe Leu Thr Tyr Val<br>435                      440                   445 | 1344 |
| aaa ctc gga cgg ata aaa acc gaa cgc ccc gcc gtc caa ccg aag gcg<br>Lys Leu Gly Arg Ile Lys Thr Glu Arg Pro Ala Val Gln Pro Lys Ala<br>          450                      455                   460 | 1392 |
| cag gat gaa gag ggg gac gaa gag ggt gta ggc gtt gat aac ggt aaa<br>Gln Asp Glu Glu Gly Asp Glu Glu Gly Val Gly Val Asp Asn Gly Lys<br>465                      470                   475                 480 | 1440 |
| gaa agc gaa gac gaa atc ggc gat gaa gaa agc acc gga gac gaa gtc<br>Glu Ser Glu Asp Glu Ile Gly Asp Glu Glu Ser Thr Gly Asp Glu Val<br>                 485                    490                   495 | 1488 |
| gta gaa gat gaa gac gaa gat gaa gac gaa gaa gaa atc gaa gaa gaa<br>Val Glu Asp Glu Asp Glu Asp Glu Asp Glu Glu Glu Ile Glu Glu Glu<br>        500                          505                   510 | 1536 |
| cct gaa gaa gaa gct gaa gag gaa gaa ccc gaa gaa gaa ttg ccg gca<br>Pro Glu Glu Glu Ala Glu Glu Glu Glu Pro Glu Glu Glu Leu Pro Ala<br>515                      520                   525 | 1584 |
| gaa gaa ggc aac ggc ggt tca ggc agc atc ctg ccc act ccg gaa gcc<br>Glu Glu Gly Asn Gly Gly Ser Gly Ser Ile Leu Pro Thr Pro Glu Ala<br>        530                          535                   540 | 1632 |
| tct aaa ggc agg gac atc gac ctt ttc ctg aaa ggt atc cgc acg gcg<br>Ser Lys Gly Arg Asp Ile Asp Leu Phe Leu Lys Gly Ile Arg Thr Ala<br>545                      550                   555                 560 | 1680 |
| gaa gcc gac att cca aaa aac gga acg gcg cat tat acc ggc act tgg<br>Glu Ala Asp Ile Pro Lys Asn Gly Thr Ala His Tyr Thr Gly Thr Trp<br>                 565                    570                   575 | 1728 |
| gaa gcg cgt atc ggc gta tcg gat agt ggt acg tcc att caa aag gat<br>Glu Ala Arg Ile Gly Val Ser Asp Ser Gly Thr Ser Ile Gln Lys Asp<br>        580                        585                    590 | 1776 |
| agc tat gcg aat caa ggg gca aaa gca gaa ttt acc gtt gat ttc gaa<br>Ser Tyr Ala Asn Gln Gly Ala Lys Ala Glu Phe Thr Val Asp Phe Glu | 1824 |

-continued

```
                    595                 600                 605
gcg aag acg gtg tcc gga atg ctg aca gaa aaa aat gat aca acc ccc    1872
Ala Lys Thr Val Ser Gly Met Leu Thr Glu Lys Asn Asp Thr Thr Pro
        610                 615                 620 gct ttt tat att gaa aaa ggt gtg att gac ggt aac ggt ttc cac gct    1920
Ala Phe Tyr Ile Glu Lys Gly Val Ile Asp Gly Asn Gly Phe His Ala
625                 630                 635                 640 ttg gcg cat act cgg gag aac ggt att gac ctt tct ggg cag ggt tcg    1968
Leu Ala His Thr Arg Glu Asn Gly Ile Asp Leu Ser Gly Gln Gly Ser
                645                 650                 655 act aac ccg aag aac ttc aaa gcc gac aat ctt ctt gta aca ggc ggc    2016
Thr Asn Pro Lys Asn Phe Lys Ala Asp Asn Leu Leu Val Thr Gly Gly
            660                 665                 670 ttt tat ggc ccg cag gcg gca gaa ttg ggc ggt aat att atc gac agc    2064
Phe Tyr Gly Pro Gln Ala Ala Glu Leu Gly Gly Asn Ile Ile Asp Ser
        675                 680                 685 gac cgg aaa ttc ggt gcg gta ttt ggg gcg aaa aaa gat gac aag gag    2112
Asp Arg Lys Phe Gly Ala Val Phe Gly Ala Lys Lys Asp Asp Lys Glu
690                 695                 700 gca aca cga tga                                                    2124
Ala Thr Arg
705
```

<210> SEQ ID NO 10
<211> LENGTH: 707
<212> TYPE: PRT
<213> ORGANISM: Neisseria meningitidis strain 881607

<400> SEQUENCE: 10

```
Met Cys Lys Pro Asn Tyr Gly Gly Ile Val Leu Leu Pro Leu Leu Leu
  1               5                  10                  15

Ala Ser Cys Ile Gly Gly Asn Phe Gly Val Gln Pro Val Val Glu Ser
             20                  25                  30

Thr Pro Thr Ala Tyr Pro Val Thr Phe Lys Ser Lys Asp Val Pro Thr
         35                  40                  45

Ser Pro Pro Ala Gly Ser Ser Val Glu Thr Thr Pro Val Asn Arg Pro
 50                  55                  60

Ala Val Gly Ala Ala Met Arg Leu Leu Arg Arg Asn Ile Ala Thr Ser
 65                  70                  75                  80

Asp Lys Asp Gly Asn Asp Phe Pro Asn Ser Lys Gln Ala Glu Glu Lys
                 85                  90                  95

Leu Ser Phe Lys Glu Glu Asp Ile Leu Phe Leu Tyr Gly Ser Lys Lys
            100                 105                 110

Asp Gln Arg Gln Gln Leu Lys Asp Lys Ile Arg Gln Pro Asn Pro Thr
        115                 120                 125

Ala Ser Ile Thr Thr Ser Glu Lys Lys Asn Lys Lys Tyr Asp Tyr Lys
    130                 135                 140

Phe Val Asp Ala Gly Tyr Val Tyr Thr Lys Asp Gly Lys Asp Glu Ile
145                 150                 155                 160

Glu Trp Thr Ser Asn Tyr Lys Gln Ser Thr Asn Arg Phe Gly Tyr Asp
                165                 170                 175

Gly Phe Val Tyr Tyr Ser Gly Glu His Pro Ser Gln Ser Leu Pro Ser
            180                 185                 190

Ala Gly Thr Val Lys Tyr Ser Gly Asn Trp Gln Tyr Met Thr Asp Ala
        195                 200                 205

Ile Arg His Arg Thr Gly Lys Ala Gly Asp Pro Ser Glu Asp Leu Gly
    210                 215                 220
```

```
                                   -continued

Tyr Ile Val Tyr Tyr Gly Gln Asn Val Gly Ala Thr Ser Tyr Ala Ala
225                 230                 235                 240

Thr Ala Asp Asp Arg Glu Gly Lys His Pro Ala Glu Tyr Thr Val Asn
            245                 250                 255

Phe Asp Gln Lys Thr Leu Asn Gly Lys Leu Ile Lys Asn Gln Tyr Val
        260                 265                 270

Gln Lys Arg Asp Asp Pro Lys Lys Pro Leu Thr Ile Tyr Asp Ile Thr
    275                 280                 285

Ala Lys Leu Asp Gly Asn Arg Phe Thr Gly Ser Ala Lys Val Asn Thr
290                 295                 300

Glu Val Lys Thr Asn His Ala Asp Lys Glu Tyr Leu Phe Phe His Thr
305                 310                 315                 320

Asp Ala Asp Gln Arg Leu Glu Gly Gly Phe Phe Gly Asp Lys Gly Glu
            325                 330                 335

Glu Leu Ala Gly Arg Phe Ile Ser Asn Asp Asn Ser Val Phe Gly Val
        340                 345                 350

Phe Ala Gly Lys Gln Lys Thr Glu Thr Ala Asn Ala Ser Asp Thr Asn
    355                 360                 365

Pro Ala Leu Pro Ser Gly Lys His Thr Lys Ile Leu Asp Ser Leu Lys
370                 375                 380

Ile Ser Val Asp Glu Ala Ser Gly Glu Asn Pro Arg Pro Phe Glu Val
385                 390                 395                 400

Ser Thr Met Pro Asp Phe Gly His Pro Asp Lys Leu Leu Val Glu Gly
            405                 410                 415

Arg Glu Ile Pro Leu Val Asn Lys Glu Gln Thr Ile Asp Leu Ala Asp
        420                 425                 430

Gly Arg Lys Met Thr Val Arg Ala Cys Cys Asp Phe Leu Thr Tyr Val
    435                 440                 445

Lys Leu Gly Arg Ile Lys Thr Glu Arg Pro Ala Val Gln Pro Lys Ala
450                 455                 460

Gln Asp Glu Glu Gly Asp Glu Glu Gly Val Gly Val Asp Asn Gly Lys
465                 470                 475                 480

Glu Ser Glu Asp Glu Ile Gly Asp Glu Glu Ser Thr Gly Asp Glu Val
            485                 490                 495

Val Glu Asp Glu Asp Glu Asp Glu Glu Ile Glu Glu Glu
        500                 505                 510

Pro Glu Glu Glu Ala Glu Glu Glu Pro Glu Glu Glu Leu Pro Ala
    515                 520                 525

Glu Glu Gly Asn Gly Gly Ser Gly Ser Ile Leu Pro Thr Pro Glu Ala
530                 535                 540

Ser Lys Gly Arg Asp Ile Asp Leu Phe Leu Lys Gly Ile Arg Thr Ala
545                 550                 555                 560

Glu Ala Asp Ile Pro Lys Asn Gly Thr Ala His Tyr Thr Gly Thr Trp
            565                 570                 575

Glu Ala Arg Ile Gly Val Ser Asp Ser Gly Thr Ser Ile Gln Lys Asp
        580                 585                 590

Ser Tyr Ala Asn Gln Gly Ala Lys Ala Glu Phe Thr Val Asp Phe Glu
    595                 600                 605

Ala Lys Thr Val Ser Gly Met Leu Thr Glu Lys Asn Asp Thr Thr Pro
610                 615                 620

Ala Phe Tyr Ile Glu Lys Gly Val Ile Asp Gly Asn Gly Phe His Ala
625                 630                 635                 640
```

```
Leu Ala His Thr Arg Glu Asn Gly Ile Asp Leu Ser Gly Gln Gly Ser
                645                 650                 655

Thr Asn Pro Lys Asn Phe Lys Ala Asp Asn Leu Leu Val Thr Gly Gly
            660                 665                 670

Phe Tyr Gly Pro Gln Ala Ala Glu Leu Gly Gly Asn Ile Ile Asp Ser
        675                 680                 685

Asp Arg Lys Phe Gly Ala Val Phe Gly Ala Lys Lys Asp Asp Lys Glu
    690                 695                 700

Ala Thr Arg
705

<210> SEQ ID NO 11
<211> LENGTH: 94
<212> TYPE: DNA
<213> ORGANISM: Neisseria meningitidis

<400> SEQUENCE: 11
cgggttgata ttatctgtac atattaatat aatgataatt attattaatc aaataggagg    60
aaaagtaggg atgtgtaaac cgaattatgg cggc                                94

<210> SEQ ID NO 12
<211> LENGTH: 599
<212> TYPE: PRT
<213> ORGANISM: Neisseria meningitidis strain B16B6

<400> SEQUENCE: 12

Met Asn Asn Pro Leu Val Asn Gln Ala Ala Met Val Leu Pro Val Phe
  1               5                  10                  15

Leu Leu Ser Ala Cys Leu Gly Gly Gly Gly Ser Phe Asp Leu Asp Ser
             20                  25                  30

Val Glu Thr Val Gln Asp Met His Ser Lys Pro Lys Tyr Glu Asp Glu
         35                  40                  45

Lys Ser Gln Pro Glu Ser Gln Gln Asp Val Ser Glu Asn Ser Gly Ala
     50                  55                  60

Ala Tyr Gly Phe Ala Val Lys Leu Pro Arg Arg Asn Ala His Phe Asn
 65                  70                  75                  80

Pro Lys Tyr Lys Glu Lys His Lys Pro Leu Gly Ser Met Asp Trp Lys
                 85                  90                  95

Lys Leu Gln Arg Gly Glu Pro Asn Ser Phe Ser Glu Arg Asp Glu Leu
            100                 105                 110

Glu Lys Lys Arg Gly Ser Ser Glu Leu Ile Glu Ser Lys Trp Glu Asp
        115                 120                 125

Gly Gln Ser Arg Val Val Gly Tyr Thr Asn Phe Thr Tyr Val Arg Ser
    130                 135                 140

Gly Tyr Val Tyr Leu Asn Lys Asn Asn Ile Asp Ile Lys Asn Asn Ile
145                 150                 155                 160

Val Leu Phe Gly Pro Asp Gly Tyr Leu Tyr Tyr Lys Gly Lys Glu Pro
                165                 170                 175

Ser Lys Glu Leu Pro Ser Glu Lys Ile Thr Tyr Lys Gly Thr Trp Asp
            180                 185                 190

Tyr Val Thr Asp Ala Met Glu Lys Gln Arg Phe Glu Gly Leu Gly Ser
        195                 200                 205

Ala Ala Gly Gly Asp Lys Ser Gly Ala Leu Ser Ala Leu Glu Glu Gly
    210                 215                 220

Val Leu Arg Asn Gln Ala Glu Ala Ser Ser Gly His Thr Asp Phe Gly
225                 230                 235                 240
```

```
Met Thr Ser Glu Phe Glu Val Asp Phe Ser Asp Lys Thr Ile Lys Gly
            245                 250                 255

Thr Leu Tyr Arg Asn Asn Arg Ile Thr Gln Asn Asn Ser Glu Asn Lys
            260                 265                 270

Gln Ile Lys Thr Thr Arg Tyr Thr Ile Gln Ala Thr Leu His Gly Asn
            275                 280                 285

Arg Phe Lys Gly Lys Ala Leu Ala Ala Asp Lys Gly Ala Thr Asn Gly
            290                 295                 300

Ser His Pro Phe Ile Ser Asp Ser Asp Ser Leu Glu Gly Gly Phe Tyr
305                 310                 315                 320

Gly Pro Lys Gly Glu Glu Leu Ala Gly Lys Phe Leu Ser Asn Asp Asn
            325                 330                 335

Lys Val Ala Ala Val Phe Gly Ala Lys Gln Lys Asp Lys Lys Asp Gly
            340                 345                 350

Glu Asn Ala Ala Gly Pro Ala Thr Glu Thr Val Ile Asp Ala Tyr Arg
            355                 360                 365

Ile Thr Gly Glu Glu Phe Lys Lys Glu Gln Ile Asp Ser Phe Gly Asp
            370                 375                 380

Val Lys Lys Leu Leu Val Asp Gly Val Glu Leu Ser Leu Leu Pro Ser
385                 390                 395                 400

Glu Gly Asn Lys Ala Ala Phe Gln His Glu Ile Glu Gln Asn Gly Val
            405                 410                 415

Lys Ala Thr Val Cys Cys Ser Asn Leu Asp Tyr Met Ser Phe Gly Lys
            420                 425                 430

Leu Ser Lys Glu Asn Lys Asp Asp Met Phe Leu Gln Gly Val Arg Thr
            435                 440                 445

Pro Val Ser Asp Val Ala Ala Arg Thr Glu Ala Asn Ala Lys Tyr Arg
            450                 455                 460

Gly Thr Trp Tyr Gly Tyr Ile Ala Asn Gly Thr Ser Trp Ser Gly Glu
465                 470                 475                 480

Ala Ser Asn Gln Glu Gly Gly Asn Arg Ala Glu Phe Asp Val Asp Phe
            485                 490                 495

Ser Thr Lys Lys Ile Ser Gly Thr Leu Thr Ala Lys Asp Arg Thr Ser
            500                 505                 510

Pro Ala Phe Thr Ile Thr Ala Met Ile Lys Asp Asn Gly Phe Ser Gly
            515                 520                 525

Val Ala Lys Thr Gly Glu Asn Gly Phe Ala Leu Asp Pro Gln Asn Thr
            530                 535                 540

Gly Asn Ser His Tyr Thr His Ile Glu Ala Thr Val Ser Gly Gly Phe
545                 550                 555                 560

Tyr Gly Lys Asn Ala Ile Glu Met Gly Gly Ser Phe Ser Phe Pro Gly
            565                 570                 575

Asn Ala Pro Glu Gly Lys Gln Glu Lys Ala Ser Val Val Phe Gly Ala
            580                 585                 590

Lys Arg Gln Gln Leu Val Gln
            595
```

NEISSERIA LACTOFERRIN BINDING PROTEIN

This application is a continuation of application Ser. No. 09/485,760, filed Feb. 15, 2000 now abandoned, which is a 371 of International Application No. PCT/EP98/05117, filed Aug. 10, 1998.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the neisserial outer-membrane protein (OMP) family, and in particular to lactoferrin-binding protein B (LbpB). Furthermore, the invention relates to the therapeutic use of LbpB, such as for vaccination against neisserial disease.

BACKGROUND OF THE INVENTION

Meningitis is either of bacterial or viral origin, the bacterial form being by far the most severe. The bacteria mainly responsible are *Neisseria meningitidis, Haemophilus influenzae* and *Streptococcus pneumoniae*. Since the launch of a conjugate vaccine against *H. influenzae* type B (Hib), and its integration into routine infant vaccination, *N. meningitidis* is taking over as the leading cause of meningitis throughout the world, there being an estimated 2,600 cases per year in the USA alone.

The species *N. meningitidis* is subdivided into 13 serogroups according to the composition of the capsular polysaccharides. In addition, each serogroup is sub-classified into serotypes, subtypes, and immunotypes on the basis of other components of the bacteria. Three serogroups (A, B, and C) account for more than 90% of cases of meningitis, and in developed, industrial nations, serogroup B is responsible for 50 to 80% of cases.

Effective vaccines based on capsular polysaccharides exist to prevent meningitis caused by *N. meningitidis* serogroups A and C. The serogroup C polysaccharide vaccines do not produce a protective effect in children less than 2 years of age (the age range where there is the greatest risk of developing meningitis), however this drawback may be overcome by conjugating these polysaccharides to a carrier protein. Conjugation has the additional advantage of inducing an immunological memory against the antigen.

In contrast, the polysaccharide of *N. meningitidis* serogroup B displays little or no immunogenicity in man, irrespective of whether or not it is in a conjugated form. It would therefore be highly desirable to obtain a vaccine against neisserial disease induced by *N. meningitidis* (in particular of serogroup B) other than a polysaccharide-based vaccine.

A promising class of vaccine candidates are those using the outer membrane proteins (OMPs) of *N. meningitidis*, because they may provide antigens that are immunogenic and accessible to the human immune response. The OMPs responsible for the uptake of iron into the cell are particularly promising.

Iron is an essential nutrient for most bacteria. In the extracellular compartments of the human body iron is complexed mainly to transferrin in serum and to lactoferrin on mucosal surfaces (Finkelstein et al., 1983), with negligible amounts in the free form. Therefore, efficient iron acquisition is an important virulence factor for pathogenic bacteria.

As regards *N. meningitidis* in particular (a strict pathogen of man), its iron requirements are met by using receptors for human iron-chelating proteins, such as transferrin or lactoferrin, which enable the cell to bind these proteins and thereafter to take up the iron needed for its growth. The synthesis of these receptor proteins is induced when the bacteria sense iron limitation.

The receptor proteins involved in the uptake of iron from transferrin, ThpA and TbpB (Cornelissen et al., 1992; Legrain et al., 1993; Anderson et al. 1994) and from lactoferrin binding protein A (LbpA) (Pettersson et al., 1993; 1994b; Biswas and Sparling, 1995) have been cloned and sequenced. The transferrin-binding receptor proteins form a complex in the outer membrane. In *N. meningitidis*, both ThpA and TbpB seem to be necessary for iron transportation (Irwin et al., 1993). ThpA is an integral membrane protein, whereas TbpB is a lipoprotein and is anchored to the membrane only with its lipid moiety. The current model for the mechanism of the receptor proposes that iron-loaded transferrin binds to the receptor complex. In this complex, the TbpB protein discriminates between ferrated- and apotransferrin. Binding of transferrin results in the conformational change in the receptor, which releases iron from transferrin and opens a gated pore in ThpA, and iron can be transported accross the outer membrane (Cornelissen and Sparling, 1994; 1996).

The lactoferrin receptor is also thought to be an important virulence factor of *N. meningitidis*. The main site of entry into the human body is the nasopharynx, where lactoferrin is the main iron source. Furthermore, preliminary reports show that lactoferrin is able to cross the blood-brain barrier in acute inflammation (Gschwentner et al., 1997). It is possible that lactoferrin is also an important iron source for the meningococci at a later stage of infection, when the bacteria have reached the meninges. By using an affinity isolation procedure, a single lactoferrin-binding protein was originally identified (Schryvers and Morris, 1988). The structural gene for this receptor, designated LbpA, has been characterised (Pettersson et al., 1993; 1994b; Biswas and Sparling, 1995) and a topology model for the protein in the outer membrane has been proposed (Pettersson et al., 1994a). The protein shows homology to ThpA. In addition, part of a possible open reading frame was identified upstream of the lbpA gene, and the deduced amino acid sequence showed homology to TbpB (Pettersson et al., 1994a).

TbpB and other purified meningococcal OMPs have been the subject of previous patent applications with respect to their use as vaccines against *N. meningitidis* (e.g. TbpB, WO 9307172; 22 kDa surface protein, WO 9629412; haemoglobin receptor, WO 9612020; porin protein, WO 9503413; pilin proteins, WO 9408013; 64 kDa OMP, EP 474313-B I).

There is a need for identification and characterization of further members of the OMP family which can play a role in preventing, ameliorating or correcting dysfunctions or diseases, including, but not limited to, neisserial disease (for example meningitis).

Antibodies against LbpA do not seem to be bactericidal and it may therefore be of limited use as a vaccine candidate (Pettersson et al., 1993).

This invention identifies and characterises another lactoferrin-binding receptor protein, lactoferrin binding protein B (LbpB), its role in the utilisation of iron from lactoferrin, and its therapeutic uses.

There are several advantages LbpB has over the other OMP vaccine candidates. Firstly, in the blood-borne stage of meningococcal disease human lactoferrin is essential to the organism as it has a 300 fold greater affinity for binding iron than human transferrin, and hence the use of lactoferrin as an iron source is essential to the organism. Secondly, lactoferrin has a known antibacterial effect, and its concentration in the blood increases upon infection. It is also therefore important for the organism to bind human lactoferrin as a way of gaining some resistance to this effect. Lastly, human lactoferrin is the main source of iron to N. meningitidis at the place of entry of the bacteria to the human body (the nasopharynx).

The significance of these advantages is that LbpB antigens would be likely to be expressed at the cell surface in the vast majority of meningococci in the body, that the cell-surface domain of LbpB is likely to be very conserved because it must effectively bind lactoferrin, and that an immune response directed against the LbpB antigen may not only stop any infection of meningococcus in the blood, it may also stop even the carriage of the organism in the nasopharynx.

SUMMARY OF THE INVENTION

In one aspect, the invention relates to LbpB polypeptides and recombinant materials and methods for their production. Another aspect of the invention relates to methods for using such LbpB polypeptides and polynucleotides. Such uses include the prevention and treatment of neisserial disease (for example meningitis), among others. In still another aspect, the invention relates to diagnostic assays for detecting diseases associated with the presence of LbpB.

BRIEF DESCRIPTION OF THE DRAWINGS

FIG. 3. Alignment of proteins LbpB of strain BNCV (SEQ ID NO:2) and TbpB of strain B16B6 (SEQ ID NO:12). Identical amino acids are marked by dashes. The numbers to the right indicate the positions of amino acids. Gaps (–) were introduced to achieve optimal alignment. Peptides used to immunise mice are indicated above the sequence of LbpB (SEQ ID NO:2). Two stretches, rich in negatively charged residues are underlined. The putative signal peptidase H cleavage site is shown with an arrow above the sequence.

FIG. 4. Sequence of the promoter area upstream of lbpB (SEQ ID NO:1 1). The translation initiation site (ATG) is marked in bold. The ribosome binding site, and the putative –10 and –35 boxes are underlined (thick line and thin lines respectively). The putative Fur box is boxed.

FIG. 9. Alignment of the LbpB proteins from five meningococcal strains: BNCV (SEQ ID NO: 2); M981 (SEQ ID NO:4); H44/76 (SEQ ID NO:6); M990 (SEQ ID NO: 8); and 881607 (SEQ ID NO:10). The alignment was performed with the CLUSTAL program (PC Gene, IntelliGenetics), and optimized by hand. Numbers to the right indicate the positions of the amino acids. Gaps (–) were introduced to achieve optimal alignment. Positions where all five sequences are identical, are marked with *.

B. The amino acid sequences of the recombinant LbpB construct (underneath) as compared with the wild-type LbpB sequence (on top). Only the last and first amino acid residues of the LbpB/PhoE signal sequences and mature LbpB, respectively, are shown. The His-tag and the Factor Xa cleavage site are shown entirely. The leader peptidase I and II (LPaseI and II, respectively) and Factor Xa cleavage sites are shown by arrows.

Figure 11:
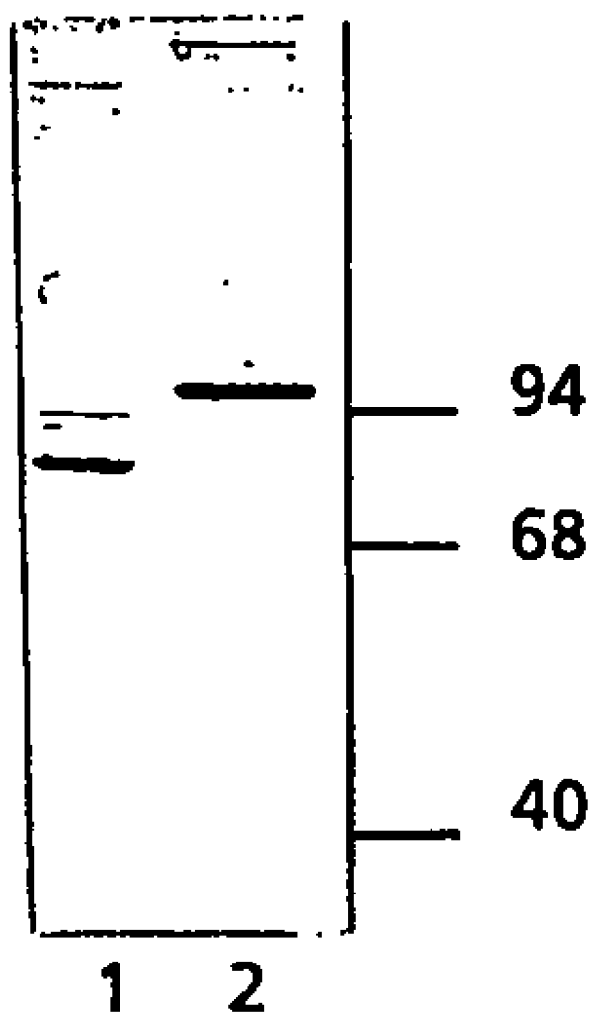

FIG. 11. PAGE of the purified recombinant LbpB protein. Lanes 1 and 2 show samples incubated at 0° C. and 100° C., respectively, before electrophoresis. The positions of molecular weight standards are indicated on the right in kDa.

Figure 12:
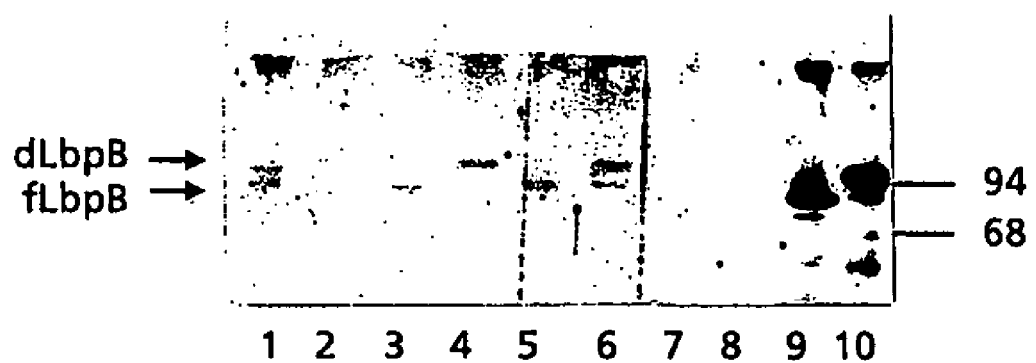

FIG. 12. Western blot with folded (lanes 1, 3, 5, 7, and 9) and denatured (lanes 2, 4, 6, 8, and 10) recombinant LbpB with five human convalescent sera. Lanes 1 and 2, serum 69; lanes 3 and 4, serum 262439; lanes 5 and 6, serum 262532; lanes 7 and 8, serum 263017, lanes 9 and 10, serum 330. The positions of molecular size standards are indicated at the right in kilodaltons. Arrows at the left indicate the positions of denatured (dLbpB) and folded LbpB (fLbpB).

FIG. 13. Results of the anti Whole Cell and anti-LbpB ELISA (Table 7) performed as described in Example 10. A. anti-LbpB response in mice immunized with either LbpB or *N. meningitidis* strain BNCV whole cells. A control immunization was carried out with PBS solution. B. anti Whole Cell (strain BNCV grown in iron deficient conditions) response in mice immunized with either LbpB or *N. meningitidis* strain BNCV whole cells. A control immunization was carried out with PBS solution. C. anti Whole Cell (strain H44/76 grown in iron deficient conditions) response in mice immunized with either LbpB or *N. meningitidis* strain BNCV whole cells. A control immunization was carried out with PBS solution.

Figure 14:
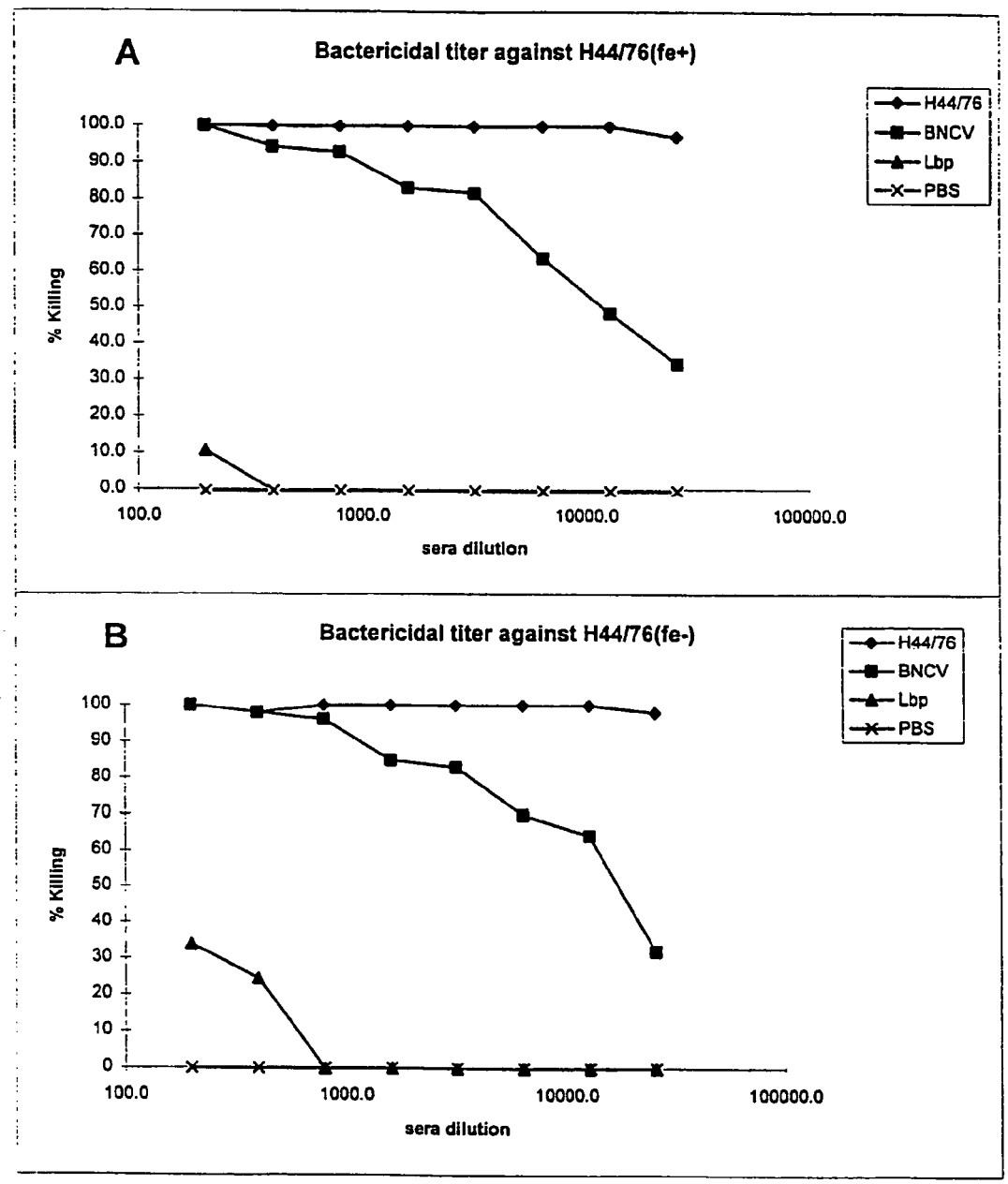

FIG. 14. Results of the bactericidal activities (Table 8) of anti Whole Cell and anti strain BNCV LbpB sera performed as described in Example 10. A. Bactericidal titer against *N. meningitidis* strain H44/76 (grown in iron-rich conditions). B. Bactericidal titer against *N. meningitidis* strain H44/76 (grown in iron-depleted conditions).

DESCRIPTION OF THE INVENTION

Definitions

The following definitions are provided to facilitate understanding of certain terms used frequently herein.

"LbpB" refers generally to a polypeptide, preferably a lipoprotein, having the amino acid sequence set forth in SEQ ID NO:2, 4, 6, 8, or 10, or an allelic variant thereof.

"LbpB activity or LbpB polypeptide activity" or "biological activity of the LbpB or LbpB polypeptide" refers to the metabolic or physiologic function of said LbpB including similar activities. Specifically, the LbpB activity is the ability to bind to human lactoferrin. This activity of LbpB can be tested using the method described in Example 6. Also included in this definition are antigenic and immunogenic activities of said LbpB. This antigenicity can best be tested using the immunoblot method described in Example 9, preferably using polyclonal sera against LbpB of meningococcal strain BNCV as described in Example 10A. The immunogenicity can best be tested by measuring antibody responses (using polyclonal sera generated against the variant) in ELISA using purified LbpB from meningococcal strain BNCV, as described in Example 10B.

"lbpB gene" refers to a polynucleotide having the nucleotide sequence 100–2274 set forth in SEQ ID NO:1, or the complete nucleotide sequence set forth in SEQ ID NO: 3, 5, 7, or 9, or allelic variants thereof and/or their complements.

"Antibodies" as used herein includes polyclonal and monoclonal antibodies, chimeric, single chain, and humanized antibodies, as well as Fab fragments, including the products of a Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications include acetylation, acylation, ADP-ribosylation, anidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential biological properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant (for instance, SEQ ID NO:3, 5, 7 or 9 are variants of the lbpB polynucleotide of SEQ ID NO:1; and SEQ ID NO:4, 6, 8 or 10 are variants of the LbpB polypeptide of SEQ ID NO:2), or it may be a variant that is not known to occur naturally. Non-naturally occurring variants of polynucleotides and polypeptides may be made by mutagenesis techniques or by direct synthesis. Variants should retain one or more of the biological activities of the LbpB polypeptide. They should either be capable of binding human lactoferrin (preferably as described in the test for this activity in Example 6), or have similar antigenic or immunogenic activities as LbpB. The antigenicity can best be tested using the immunoblot method described in Example 9, preferably using polyclonal sera against LbpB of meningococcal strain BNCV as described in Example 10A. The immunogenicity can best be tested by measuring antibody responses (using polyclonal sera generated against the variant) in ELISA using purified LbpB from meningococcal strain BNCV, as described in Example 10B. Preferably, a variant would retain all of the above biological activities.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heijne, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include on average up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include on average up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to LbpB polypeptides (or LbpB proteins). The LbpB polypeptides include the polypeptides of SEQ ID NO:2, 4, 6, 8, or 10 (residues 1–18 is the natural signal peptide of each of the proteins, and residue Cys19 is the N-terminal amino acid which is lipidated in the natural mature protein); as well as polypeptides comprising the amino acid sequence of SEQ ID NO: 2, 4, 6, 8, or 10; and polypeptides comprising the amino acid sequence which have at least 65% identity to that of SEQ ID NO:2, 4, 6, 8, or 10 over its entire length, and still more preferably at least 70% identity, and still more preferably at least 80% identity, and even still more preferably at least 90% identity to SEQ ID NO: 2, 4, 6, 8, or 10. Furthermore, those with at least 95–99% are highly preferred. Also included within LbpB polypeptides are polypeptides having the amino acid sequence which have at least 65% identity to the polypeptide having the amino acid sequence of SEQ ID NO:2, 4, 6, 8, or 10 over its entire length, and still more preferably at least 70% identity, and still more preferably at least 80% identity, and still more preferably at least 90% identity to SEQ ID NO:2, 4, 6, 8, or 10. Furthermore, those with at least 95–99% are highly preferred.

The LbpB polypeptides provided in SEQ ID NO:2, 4, 6, 8, and 10 are the LbpB polypeptides from *Neisseria meningitidis* strains BNCV, M981, H44/76, M990, and 881607 repectively.

The LbpB polypeptides may be in the form of the "mature" protein or may be a part of a larger protein such as a fusion protein. It may be advantageous to include an additional amino acid sequence which contains secretory or leader sequences (such as the natural LbpB leader sequence; residues 1–18 in SEQ ID NO:2, 4, 6, 8, and 10), prosequences, sequences which aid in purification such as multiple histidine residues, or an additional sequence for stability during recombinant production.

Fragments of the LbpB polypeptides are also included in the invention. A fragment is a polypeptide having an amino acid sequence that entirely is the same as part, but not all, of the amino acid sequence of the aforementioned LbpB polypeptides. As with LbpB polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of LbpB polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of LbpB polypeptides, except for deletion of a continuous series of residues that includes the amino terminus, or a continuous series of residues that includes the carboxyl terminus and/or transmembrane region or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate LbpB activity, including those with a similar activity or an improved activity, or with a decreased undesirable activity. Also included are those that are antigenic or immunogenic in an animal, especially in a human.

Fragments should retain one or more of the biological activities of the LbpB polypeptide. Preferably, the polypeptide fragments should be continuous stretches (over 16 amino acids) of amino acid sequence derived from SEQ ID NO:2, 4, 6, 8, or 10 having an antigenic or immunogenic biological activity that the full length LbpB polypeptide from which it was derived also possesses.

Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

Most preferred variants are those that vary from the referents by amino acid substitutions that are found in structurally equivalent positions (as shown by a homology alignment) in other LbpB sequences (for example homology alignment of 5 LbpB sequences shown in FIG. 9). Especially preferred variants comprising the amino acid sequence which have at least 65% identity to that of the reference sequence (for instance SEQ ID NO: 2, 4, 6, 8, or 10) over its entire length, and still more preferably at least 70% identity, and still more preferably at least 80% identity, and even still more preferably at least 90% identity. Furthermore, those with at least 95–99% are highly preferred. For instance, in FIG. 9 if LbpB from BNCV is the reference sequence, a variant would encompass residues 300–308 being replaced with any of the residues in the equivalent positions in the LbpB sequences of strain H44/76 (residues 305–313 respectively), strain M990 (residues 307–315 respectively), strain M981 (residues 302–310 respectively), or strain 881607 (residues 303–311 respectively). The amino acid sequence NPDLAKSHA could therefore be substituted for STDVATNLA [ST (from M981 residues 302–303), D (from BNCV residue 302), V (from 881607 residue 306), A (from M990 residue 311), T (from H44/76 residue 310), NLA (from M990 residues 313–315)] and the resulting protein may be classed a variant, and a polypeptide of the invention.

Such substitutions can also include deletions, for instance if residues 357–366 of LbpB of strain M981 are deleted (as there are no equivalent amino acid positions in LbpB from strain BNCV—see FIG. 9) such a protein may constitute a variant, and a polypeptide of the invention.

In addition, it is well known that the genomes of *Neisseria meningitidis* and other neisserial strains (for instance *Neisseria gonorrhoeae*) are genomically very homologous to each other. The genomes of *Neisseria meningitidis* and *Moraxella catarrhalis* (formerly called *Neisseria catarrhalis*) are also sufficiently homologous to allow gene exchange to take place. The LbpB equivalent proteins (or LbpB allelic variants) of neisserial strains and of *Moraxella catarrhalis* strains also constitute polypeptides of the invention if they satisfy the % sequence identity criteria described above. And yet in addition, such equivalent proteins would also constitute polypeptides of the invention if they shared preferably at least 65% sequence similarity with one of the reference sequences (SEQ ID NO: 2, 4, 6, 8, or 10) over its entire length as measured by the program BLAST (Altschul, S. F. et al., (1997) Nucleic Acids Res. 25:3389–3402; Karlin, S. and Altschul, S. F. (1990) Proc. Natl. Acad. Sci. USA 87:2264–68; Karlin, S. and Altschul, S. F. (1993) Proc. Natl. Acad. Sci. USA 90:5873–7), and more preferably at least 70% similarity, and still more preferably at least 80% similarity, and even still more preferably at least 90%. Furthermore, those with at least 95–99% are highly preferred. Such proteins should bind human lactoferrin (by definition), and should also be able to cross-react with polyclonal sera against LbpB from meningococcal strains. The precise amino-acid sequence of such variants can be easily determined using information from the meningococcal polynucleotide and polypeptide sequences of SEQ ID NO:1–10.

The LbpB polypeptides of the invention can be prepared in any suitable manner. Such polypeptides include isolated naturally occurring lipopolypeptides, recombinantly produced polypeptides or lipopolypeptides, synthetically produced polypeptides, or polypeptides produced by a combination of these methods. Means for preparing such polypeptides are well understood in the art.

Polynucleotides of the Invention

Another aspect of the invention relates to LbpB polynucleotides. LbpB polynucleotides include isolated polynucleotides which encode the LbpB polypeptides and fragments, and polynucleotides closely related thereto. More specifically, LbpB polynucleotide of the invention include a polynucleotide comprising the nucleotide sequence contained in SEQ ID NO:1, 3, 5, 7, or 9 encoding a LbpB polypeptide of SEQ ID NO: 2, 4, 6, 8, or 10 respectively, and polynucleotide having the particular sequence of SEQ ID NO:1, 3, 5, 7, or 9. LbpB polynucleotides further include a polynucleotide comprising a nucleotide sequence that has at least 65% identity over its entire length to a nucleotide sequence encoding the LbpB polypeptide of SEQ ID NO:2, 4, 6, 8, or 10, and a polynucleotide comprising a nucleotide sequence that is at least 65% identical to that of SEQ ID NO:1 from nucleotide 100 to nucleotide 2274, and a polynucleotide comprising a nucleotide sequence that is at least 65% identical to that of SEQ ID NO:3, 5, 7, or 9. In this regard, polynucleotides at least 70% identical are more preferred, polynucleotides at least 80% identical are particularly preferred, and those with at least 90% are especially preferred. Furthermore, those with at least 95% are highly preferred and those with at least 98–99% are most highly preferred, with at least 99% being the most preferred. Also included under LbpB polynucleotides are a nucleotide sequence which has sufficient identity to a nucleotide sequence contained in SEQ ID NO:1, 3, 5, 7, or 9 to hybridize under conditions useable for amplification or for use as a probe or marker. The invention also provides polynucleotides which are complementary to such LbpB polynucleotides.

The LbpB polynucleotides provided in SEQ ID NO:1, 3, 5, 7, and 9 are the LbpB polynucleotides from *Neisseria meningitidis* strains BNCV, M981, H44/76, M990, and 881607 repectively.

The nucleotide sequence encoding LbpB polypeptide of SEQ ID NO:2, 4, 6, 8, or 10 may be identical to the polypeptide encoding sequence contained in nucleotides 100 to 2274 of SEQ ID NO:1, or the polypeptide encoding sequence contained in SEQ ID NO:3, 5, 7, or 9 respectively, or it may be a sequence, which as a result of the redundancy (degeneracy) of the genetic code, also encodes the polypeptide of SEQ ID NO:2, 4, 6, 8, or 10.

When the polynucleotides of the invention are used for the recombinant production of LbpB polypeptide, the polynucleotide may include the coding sequence for the mature polypeptide (residue 19 to the C-terminus of SEQ ID NO:2, 4, 6, 8, and 10) or a fragment thereof, by itself; the coding sequence for the mature polypeptide or fragment in reading frame with other coding sequences, such as those encoding a leader or secretory sequence, a pre-, or pro- or preproprotein sequence, or other fusion peptide portions (for instance residues 1 to 18 of SEQ ID NO:2, the natural signal sequence of LbpB). For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag, or is glutathione-s-transferase. Also preferred is LbpB fused to its natural signal sequence (residues 1 to 18 of SEQ ID NO:2). The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding LbpB polypeptide variants described earlier. Most preferably they comprise the amino acid sequence of the LbpB polypeptide of SEQ ID NO:2, 4, 6, 8, or 10 in which several, 10–25, 5–10, 1–5,1–3, 1–2 or 1 amino acid residues are substituted, deleted or added, in any combination, and they retain at least one of the LbpB polypeptide's biological activities.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1, 3, 5, 7, or 9 or a fragment thereof, may be used as hybridization probes for cDNA and genomic DNA, to isolate full-length cDNAs and genomic clones encoding LbpB polypeptide and to isolate cDNA and genomic clones of other genes (including genes encoding homologs and orthologs from species other than *Neisseria meningitidis*) that have a high sequence similarity to the LbpB gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding LbpB polypeptide, including homologs and orthologs from species other than *Neisseria meningitidis*, comprises the steps of screening an appropriate library under stringent hybridization conditions with a labeled probe having a nucleotide sequence contained in SEQ ID NO:1, 3, 5, 7, or 9 or a fragment thereof, and isolating full-length cDNA and genomic clones containing said polynucleotide sequence. Thus in another aspect, LbpB polynucleotides of the present invention further include a nucleotide sequence comprising a nucleotide sequence that hybridize under stringent condition to a nucleotide sequence having a nucleotide sequence contained in SEQ ID NO:1, 3, 5, 7, or 9 or a fragment thereof. Also included with LbpB polypeptides are polypeptides comprising amino acid sequences encoded by nucleotide sequences obtained by the above hybridization conditions. Such hybridization techniques are well known to those of skill in the art Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as meningococci, streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide (residues 1 to 18 of SEQ ID NO:2, 4, 6, 8, or 10) or they may be heterologous signals.

To express lipidated recombinant LbpB, preferably the endogenous signal peptide is encoded in the gene construct, and the preferred host system would be a bacterial host.

If the LbpB polypeptide is to be expressed for use in screening assays, generally, it is preferred that the polypeptide be produced at the surface of the cell. In this event, the cells may be harvested prior to use in the screening assay. If LbpB polypeptide is secreted into the medium, the medium can be recovered in order to recover and purify the polypeptide; if produced intracellularly, the cells must first be lysed before the polypeptide is recovered.

LbpB polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of LbpB, antibodies against LbpB, and phage displaying antibodies against LbpB for use as diagnostic reagents. Detection of LbpB will provide a diagnostic tool that can add to or define a diagnosis of neisserial disease, among others.

Materials for diagnosis may be obtained from a subject's cells, such as from blood, urine, saliva, tissue biopsy.

Thus in another aspect, the present invention relates to a diagonostic kit for a disease or suspectability to a disease, particularly neisserial disease, which comprises:
(a) a LbpB polynucleotide, preferably the nucleotide sequence of SEQ ID NO: 1, 3, 5, 7, or 9, or a fragment thereof;
(b) a nucleotide sequence complementary to that of (a);
(c) a LbpB polypeptide, preferably the polypeptide of SEQ ID NO: 2, 4, 6, 8, or 10, or a fragment thereof; or
(d) an antibody to a LbpB polypeptide, preferably to the polypeptide of SEQ ID NO: 2, 4, 6, 8, or 10 (and more preferably to residue 19 to the C-terminus of the polypeptide of SEQ ID NO: 2, 4, 6, 8, or 10).
(e) a phage displaying an antibody to a LbpB polypeptide, preferably to the polypeptide of SEQ ID NO: 2, 4, 6, 8, or 10 (and more preferably to residue 19 to the C-terminus of the polypeptide of SEQ ID NO: 2, 4, 6, 8, or 10).

It will be appreciated that in any such kit, (a), (b), (c), (d) or (e) may comprise a substantial component.

Antibodies

The polypeptides of the invention or their fragments or analogs thereof, or cells expressing them can also be used as immunogens to produce antibodies immunospecific for the LbpB polypeptides. The term "immunospecific" means that the antibodies have substantially greater affinity for the polypeptides of the invention than their affinity for other related polypeptides in the prior art.

Antibodies generated against the LbpB polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against LbpB polypeptides may also be employed to treat neisserial disease (for example meningitis), among others. They may also be used to diagnose the disease.

Vaccines

Another aspect of the invention relates to a method for inducing an immunological response in a mammal (preferably a human) which comprises inoculating the mammal with LbpB polypeptide or epitope-bearing fragments, analogs, outer-membrane vesicles or cells (attenuated or otherwise), adequate to produce antibody and/or T cell immune response to protect said animal from neisserial disease, among others. Yet another aspect of the invention relates to a method of inducing immunological response in a mammal (preferably a human) which comprises, delivering LbpB polypeptide via a vector directing expression of LbpB polynucleotide in vivo in order to induce such an immunological response to produce antibody to protect said animal from diseases.

A further aspect of the invention relates to an immunological composition or vaccine formulation which, when introduced into a mammalian host (preferably a human), induces an immunological response in that mammal to a LbpB polypeptide wherein the composition comprises a LbpB gene, or LbpB polypeptide or epitope-bearing fragments, analogs, outer-membrane vesicles or cells (attenuated or otherwise). The vaccine formulation may further comprise a suitable carrier. The LbpB vaccine composition is preferably administered orally or parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Yet another aspect relates to an immunological/vaccine formulation which comprises the polynucleotide of the invention. Such techniques are known in the art, see for example Wolff et al., *Science*, (1990) 247:1465–8.

Screening Assays

The LbpB polypeptide of the present invention may be employed in a screening process for compounds which antagonize (antagonists, or otherwise called inhibitors) of the LbpB polypeptide of the present invention. Thus, polypeptides of the invention may also be used to identify antagonists from, for example, cells, cell-free preparations, chemical libraries, and natural product mixtures. These antagonists may be natural or modified substrates, ligands, receptors, enzymes, etc., as the case may be, of the polypeptide of the present invention; or may be structural or functional mimetics of the polypeptide of the present invention. See Coligan et al., *Current Protocols in Immunology* 1(2): Chapter 5 (1991).

LbpB polypeptides are responsible for many biological functions, including many pathologies. Accordingly, it is desirous to find compounds and drugs can inhibit the function of LbpB polypeptide. In general, antagonists may be employed for a variety of therapeutic and prophylactic purposes for such conditions as neisserial disease.

In general, such screening procedures may involve using appropriate cells which express the LbpB polypeptide or respond to LbpB polypeptide of the present invention. Such cells include cells from mammals, yeast, *Drosophila* or *E. coli*. Cells which express the LbpB polypeptide (or cell membrane containing the expressed polypeptide) or respond to LbpB polypeptide are then contacted with a test compound to observe binding, or inhibition of a functional response. The ability of the cells which were contacted with the candidate compounds is compared with the same cells which were not contacted for LbpB activity.

The assays may simply test binding of a candidate compound wherein adherence to the cells bearing the LbpB polypeptide is detected by means of a label directly or indirectly associated with the candidate compound or in an assay involving competition with a labeled competitor.

Further, the assays may simply comprise the steps of mixing a candidate compound with a solution containing a LbpB polypeptide to form a mixture, measuring LbpB activity in the mixture, and comparing the LbpB activity of the mixture to a standard.

The LbpB cDNA, protein and antibodies to the protein may also be used to configure assays for detecting the effect of added compounds on the production of LbpB mRNA and protein in cells. For example, an ELISA may be constructed for measuring secreted or cell associated levels of LbpB protein using monoclonal and polyclonal antibodies by standard methods known in the art, and this can be used to discover agents which may inhibit the production of LbpB (also called antagonist) from suitably manipulated cells or tissues.

Examples of potential LbpB polypeptide antagonists include antibodies or, in some cases, oligonucleotides or proteins which are closely related to the ligands or substrates of the LbpB polypeptide, e.g., a fragment of the ligands or substrates; or small molecules which bind to the polypeptide of the present invention but do not elicit a response, so that the activity of the polypeptide is prevented.

Thus in another aspect, the present invention relates to a screening kit for identifying antagonists, ligands, or substrates for LbpB, which comprises:

(a) a LbpB polypeptide, preferably that of SEQ ID NO:2, 4, 6, 8, or 10;
(b) a recombinant cell expressing a LbpB polypeptide, preferably that of SEQ ID NO:2, 4, 6, 8, or 10;
(c) a cell membrane expressing a LbpB polypeptide; preferably that of SEQ ID NO: 2, 4, 6, 8, or 10; or
(d) antibody to a LbpB polypeptide, preferably that of SEQ ID NO: 2, 4, 6, 8, or 10.

It will be appreciated that in any such kit, (a), (b), (c) or (d) may comprise a substantial component.

Formulation and Administration

Peptides, such as the soluble form of LbpB polypeptides, and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

EXAMPLES

The examples below are carried out using standard techniques, which are well known and routine to those of skill in the art, except where otherwise described in detail. The examples illustrate, but do not limit the invention.

Example 1

Bacterial Strains and Growth Conditions

The bacterial strains used are listed in Table 1. Meningococci were cultured overnight on GC agar plates (Difco), supplemented with Vitox (Oxoid) in a humid 5% $CO_2$— atmosphere at 37° C. Optimal expression of iron regulated proteins was achieved by adding 5 µg/ml of the iron chelator ethylenediamine di-o-hydroxyphenylacetic acid (EDDA, Sigma). For preparation of samples for SDS-PAGE, immunoblotting, and for isolation of chromosomal DNA, cells were grown as described before (Pettersson et al., 1993).

E. coli strain Y1090 (Young and Davis, 1983), which was used to propagate the λgt11 phage, was grown in Luria-Bertoldi (LB) medium supplemented with ampicillin (100 µl/ml), 0.2% maltose and 10 mM $MgCl_2$. Strain DH5α, used for cloning, was grown in LB medium, supplemented with 100 µl/ml ampicillin, 25 µg/ml kanamycin, or 100 µg/ml erythromycin, when needed for selection of recombinants. After transformation with pEMBL19-derivatives, cells were plated on LB plates supplemented with the appropriate antibiotic, and with 5-bromo-4-chloro-3-indoyl-β-D-galactoside (40 µg/ml), and 0.5 mM isopropyl-β-D-thiogalactopyranoside to screen for plasmids with inserts. Strain PC2494, used for preparing single stranded DNA, was kept on minimal medium plates, supplemented with 5 µg/ml thiamine and 0.2% glucose.

Example 2

2A: Preparation of Mouse Antiserum Against Peptides

Peptides (FIG. 3) were synthesised using an automated multiple peptide synthesiser and were coupled to tetanus toxoid as described (van der Ley et al., 1991). BALB/c mice were immunised with 50 µg of peptide and 20 µg of Quil A as an adjuvant. Two boosters were given. Serum was collected 54 days after the first injection.

2B: Identification of the lbpB Gene Product

Figure 1:
FIG. 1. Western blot analysis of proteins from whole cells grown under iron limitation. Lanes 1 and 5, strain BNCV; lanes 2 and 6, lbpA mutant CE1452; lanes 3 and 7, lbpB mutant CE1454; lanes 4 and 8, lbpAB mutant CE1402. Antisera used were directed against synthetic peptides, based on the LbpB sequence. Lanes 1 to 4, serum 17-3 against peptide C1. Lanes 5 to 8, serum 19-1 against peptide E1. The positions of molecular size standards are indicated at the right in thousands. The LbpB protein is marked with an arrow at the left.

To investigate whether the putative lbpB gene encodes a protein, antisera were raised against synthetic peptides (indicated as A1–E1 in FIG. 3) that were based on the deduced amino acid sequence of the partial open reading frame. The antisera were tested on Western blots against whole cells of strain BNCV grown under iron limitation. Sera against peptide B 1 did not show any reaction (data not shown). Antisera against the other peptides reacted with a band of approximately 95 kDa (FIG. 1). Since this band was lacking in the lbpB mutant (constructed as described below) (FIG. 1, lanes 3 and 7), it was concluded that the lbpB gene is expressed in the wild-type strain, and that it encodes a protein with an apparent molecular weight (Mr) of 95,000. Some of the sera against peptides DI and E1 showed an additional reaction with a band with an Mr of 60,000 (FIG. 1). Both of these peptides contain the sequence VVFGAK, which is also present in TbpB (FIG. 3). Therefore, the 68 K band could be TbpB. To test this possibility, a TbpB mutant, N91, and its parental strain B16B6, were tested in Western blots. Serum 19-1 (against peptide E1) reacted with two bands of 95 K and 68 K respectively, in strain B16B6, but only with the 95 K band in strain N91. This result indicates that the 68 K band is indeed TbpB (data not shown).

Example 3

SDS-PAGE and Immunoblotting

SDS-PAGE of whole cell proteins was performed as described previously (Pettersson et al., 1990, 1993). In experiments where denaturation of LbpB had to be prevented the following modifications were included. The sample buffer contained no β-mercaptoethanol. The outer membrane complexes were not heated at 95° C. in sample buffer before electrophoresis, but incubated either on ice or at 37° C. for 10 min. In the lactoferrin binding experiment, the polyacrylamide gel was composed of a 5% (w/v) stacking gel and an 8% (w/v) resolving gel containing 0.05% (w/v) SDS. The electrode buffer contained only 0.05% instead of 0.1% SDS. Electrophoresis was carried out at a constant voltage of 100 V for 2 h at 4° C. Standard sample buffer with 2% SDS was used.

Electrophoresis of outer membrane proteins to detect folded forms of LbpB was performed with the PhastSystem (Pharmacia) according to the instructions of the manufacturer, using 7.5% (w/v) homogeneous polyacrylamide gels with SDS buffer strips.

Immunoblotting was performed as described previously (Pettersson et al., 1990, 1993). In the case of PhastSystem gels, the blotting buffer contained 0.05% (w/v) SDS and the activity of the peroxidase was detected with the ECL system according to the instructions of the manufacturer (Amersham). The mouse antisera were used at a dilution of 1:500. The LbpA-specific monoclonal antibodies mn98K1 and mn98K2 (Pettersson et al., 1993) were used as a cocktail at a dilution of 1:2000 each.

Example 4

4A: Cloning and Sequencing Strategies

Figure 2:
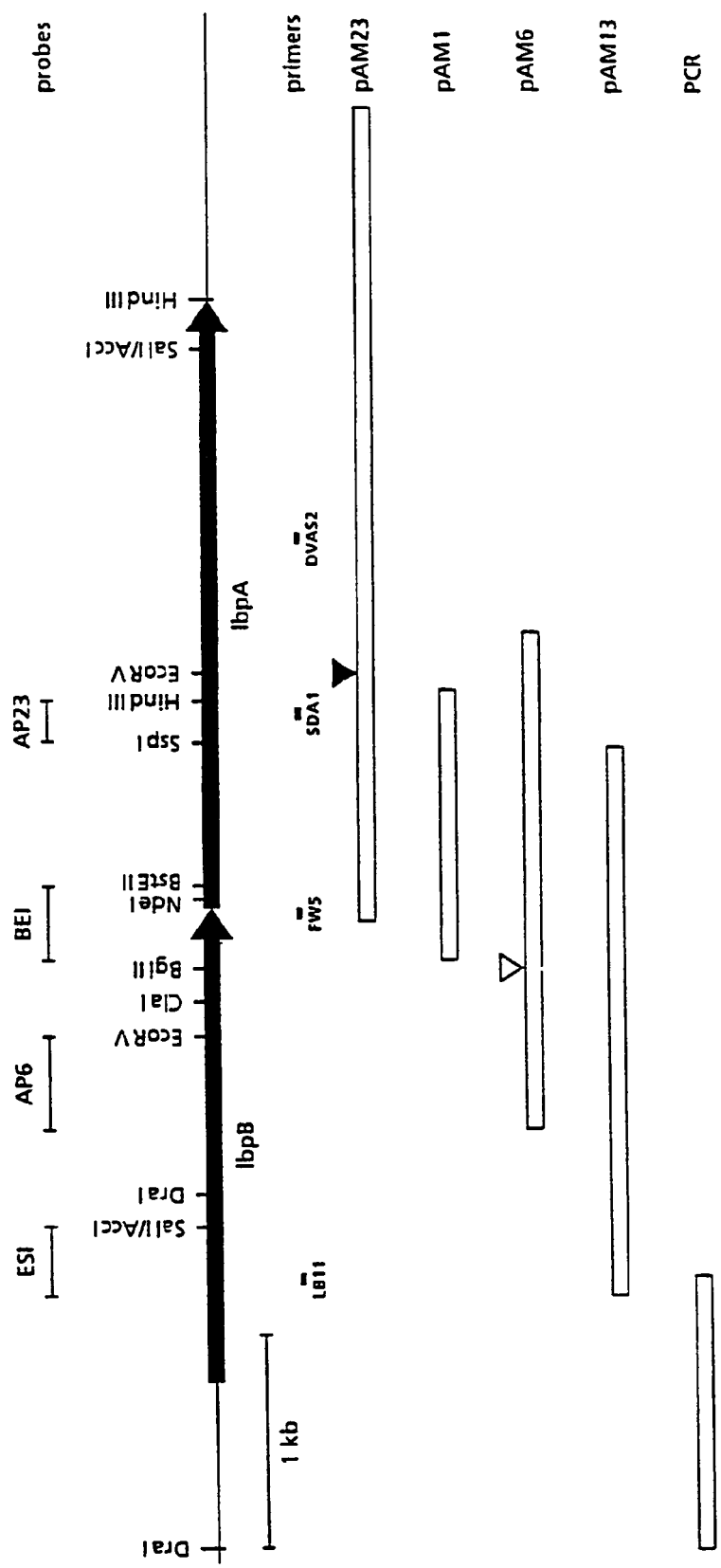
FIG. 2. Restriction map of the DNA fragments containing the lbpB and lbpA genes of strain BNCV. The inserts in the different recombinant plasmids and the PCR product (PCR) are shown as open boxes. Plasmids pAM23 and pAM 1 contain fragments of the lbpBA locus that were characterised previously (Pettersson et al. 1993, 1994a). Open reading frames are marked with heavy arrows. Probes, used for screening the library or for Southern blotting, are shown above the open reading frames. Positions of the primers used for PCR amplifications are shown underneath the open reading frames. The insertion site of the kanamycin resistance box in pAM6K is shown by an open triangle. The erythromycin resistance box in pAM23E is shown by a closed triangle.

The λgt11 gene library from strain BNCV was originally provided by E. C. Gotschlich (The Rockefeller University, New York, USA). The library was propagated in E. coli strain Y1090 and screened with DNA probes BE1 and AP6 (FIG. 2). BE1 was prepared by isolation of the 355 bp BstEII-EcoRI-fragment of plasmid pAM1 (Pettersson et al., 1993). AP6 was the 417 bp EcoRI-EcoRV-fragment prepared from plasmid pAM6. Probe labelling, plaque blotting, and detections were performed as described (Pettersson et al., 1993), using the DIG DNA Labeling and Detection kit (Boehringer Mannheim). λ DNA was isolated (Sambrook et al., 1989) and the inserts were subcloned in the phagemid pEMBL19. Plasmid DNA was isolated on Jetstar mini columns (Genomed) as described by the manufacturer. Single-stranded DNA was propagated using the helper phage VCSM 13 (Stratagene).

Chromosomal DNA was isolated as described (Ausubel et al., 1989). The DNA was digested with AccI and DraI, and separated on a 1% agarose gel. Southern blotting was performed as described (Pettersson et al., 1993). The probe ES1 (FIG. 2) was prepared by isolation of the 320 bp EcoRI-SalI-fragment from pAM13, and labelled as above. The probe reacted with a 1.5 kb fragment in the AccI/DraI digested chromosomal DNA on a Southern blot. Fragments of 1.5 kb were isolated from gel and ligated in pEMBL19. The ligation mix was PCR amplified with the M13 universal primer (Pharmacia) and the LB11 primer (Table 2). Goldstar polymerase, a Taq polymerase derivative (Eurogentec) was used for PCR amplification according to the instructions from the manufacturer. The PCR product of 1.3 kb was purified from agarose gel.

DNA sequencing was performed manually using the deaza G/A T7 sequencing mixes (Pharmacia) or automatically using the ABI Prism 310 Genetic Analyzer (Perkin Elmer). For automatic sequencing, the labelling was done with the Dye Terminator Cycle sequencing kit (Perkin Elmer). Internal primers (synthesised by Pharmacia or Gibco BRL) and the M13 universal and reverse primers (Pharmacia) were used for sequencing of single-stranded DNA, double-stranded plasmid DNA or the PCR product.

Similar strategies were used to sequence the lbpB gene from the H44/76 and M981 stains of N. meningitidis.

4B: Cloning and Sequencing of the lbpB Gene

To clone the missing part of the lbpB gene, a λgt11 gene library of strain BNCV was screened with DNA probes. Two different lambda clones were found. The inserts were subcloned in pEMBL19, resulting in plasmids pAM6 and pAM13 (FIG. 2), and sequenced. The promoter and the beginning of the lbpB gene were not found in this way. Several other attempts to clone the 5' end of the gene failed, suggesting that its expression is toxic to E. coli. To obtain the rest of the sequence, a rich bank was prepared of AccI- and DraI-digested chromosomal DNA. Chromosomal DNA fragments of approximately 1.5 kb were ligated in pEMBL19, and a PCR amplification was performed directly on the ligation mix, using a primer (LB11, see FIG. 2) based on the known part of the lbpB sequence and an M13 primer. The resulting PCR product (FIG. 2) was used directly for sequencing. This strategy avoids cloning of the possibly toxic gene in E. coli.

Sequencing of the various lbpB fragments revealed an open reading frame of 2,175 bp. It encodes a protein of 725 amino acid residues (FIG. 3) with a molecular mass of 79.4 kDa. Analysis of the N-terminal sequence revealed the characteristics of a signal sequence recognised by signal peptidase II (von Heijne, 1989). Such signal sequences are present in the precursors of lipoproteins, which are acylated at the N-terminal cysteine residue of the mature protein. A similar signal sequence was found in the TbpB protein, which was indeed proven to be lipid modified (Anderson et al., 1994). The mature LbpB protein has a calculated molecular mass of 77.5 kDa, which is considerably lower than the apparent molecular mass of 95 kDa observed in sodium dodecyl sulphate-polyacrylamide electrophoresis (SDS-PAGE) (FIG. 1). Screening of the Swiss Prot data base for similarities to other proteins revealed homology to TbpB of Neisseriae and Actinobacillus pleuropneumoniae. The highest homology, 33% identity (using the PALIGN program), was found to TbpB of N. meningitidis strain B 16B6 (Legrain et al. 1993) (FIG. 3). In the TbpB protein, some internal repeats were found, and it has been proposed that the molecule has a bi-lobed structure that is evolved after an internal duplication (Fuller et al., 1996, Renauld-Mongénie et al., 1996). When the N-terminal 354 amino acids of the mature LbpB protein were aligned with the C-terminal 353 amino acids, 30% identity and 10% similarity was found (data not shown). This result suggests that also LbpB may exist in a bi-lobed structure. The isoelectric point of the protein is 4.5. Two long stretches, rich in acidic residues, could be discerned in the sequence (FIG. 3). Since these stretches are lacking in TbpB, they could be important for binding of lactoferrin, which is, in contrast to transferrin, a positively charged molecule.

In the promoter area, a typical Shine-Dalgarno sequence could be discerned. In addition, putative –10 and –35 boxes were found (FIG. 4). A sequence reminiscent of a Fur-binding site overlaps the –10 box. Fur acts, in conjunction with $Fe^{2+}$, as a repressor of iron-regulated genes, by binding to a 19 bp sequence in the promoter region (Bagg and Neilands, 1987). The consensus sequence of such a Fur-box is GATAATGATAATCATTATC, and 16 of the 19 bp of this sequence are conserved in this element in the lbpB promoter. Further upstream of the promoter, a direct repeat of 131 bp was found (data not shown). This sequence is present at least twice at this position. The same direct repeat was found downstream of the lbpA gene (Prinz et al., unpublished observation). A FASTA homology search revealed homology of this repeat to a number of neisserial sequences, mostly flanking open reading frames (data not shown).

The sequence homology between the LbpB proteins of the BNCV and M981 strains of *N. meningitidis*, and between the LbpB proteins of the BNCV and H44/76 strains of *N. meningitidis*, is 72.7% and 78.5% respectively.

Example 5

5A: Construction of Isogenic Mutants

Plasmids pAM23 and pAM6 were used for insertional inactivation of lbpA and lbpB, respectively. The erythromycin resistance (Erm$^r$) cassette from pER2 (Jennings et al., 1993) was excised with ClaI and HindIII. The fragment was treated with T4 DNA polymerase and ligated to EcoRV-digested pAM23, resulting in plasmid pAM23E. The kanamycin resistance (Km$^r$) cassette from pUC4K (Pharmacia) was excised with HincII. Plasmid pAM6 was linearized with BglII and treated with T4 DNA polymerase. The Km$^r$-cassette was ligated in this site, resulting in plasmid pAM6K. A linker composed of the oligonucleotides nus1 and nus2 (Table 2), which contains the neisserial uptake sequence (GCCGTCTGAA) and KpnI-compatible single-stranded ends, was cloned in the KpnI-site of pAM6K, resulting in plasmid pAM6K-nus. The antibiotic resistance genes were in the same directions as lbpA and lbpB in plasmids pAM23E and pAM6K (-nus), respectively. Plasmid pAM23E, linearized with KpnI, was used to transform strain H44/76 as described previously (van der Ley and Poolman, 1992). Transformants were selected on GC plates containing 5 µg of erythromycin per ml. Correct gene replacement in one of the transformants, designated CE1449, was verified by PCR, using primers FW5 and DVAS2 (Table 2), and by Southern blot analysis using probe AP23 (FIG. 2; isolated as the 184 bp SspI-HindIII-fragment from pAM23). For Southern blot, chromosomal DNA was digested with ClaI and SalI. The isogenic mutants in strain BNCV were prepared by electroporation (Genco et al., 1991) since this strain appeared not to be transformable. Chromosomal DNA from lbpA mutant CE1449 was used to make the lbpA mutant. Transformants were selected on GC plates with erythromycin and verified as mentioned above. Plasmid pAM6K-nus was used to make the lbpB mutant. Transformants were selected on GC plates containing 100 µg/ml of kanamycin. Correct gene replacement was verified by PCR, using primers SDA1 and PR1 (Table 2), and by Southern blot using probe AP23.

5B: Construction of Isogenic Mutants

Figure 5:
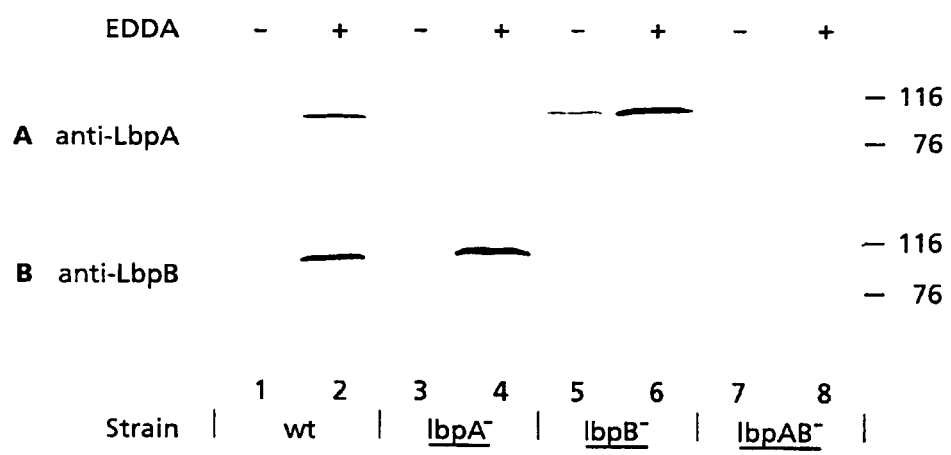
FIG. 5. Western blot analysis of proteins from whole cells grown in TSB medium (lanes 1, 3, 5, and 7) or in TSB with EDDA (lanes 2, 4, 6 and 8). Antibodies used were monoclonals mn98k1 and mn98k2 directed against LbpA (Panel A) or antiserum 17-3 against LbpB peptide C1 (Panel B). Lanes 1 and 2, strain BNCV; lanes 3 and 4, lbpA mutant CE1452; lanes 5 and 6, lbpB mutant CE1454; lanes 7 and 8, lbpAB mutant CE1402.

To verify the identity of the 94 kDa protein and to investigate the role of the individual lactoferrin-binding proteins in lactoferrin binding and utilisation, a set of isogenic derivatives of BNCV lacking either LbpA or LbpB was constructed as described in Example 5A. Correct gene replacements were verified in PCR reactions and by Southern blotting (data not shown). Expression of LbpA and LbpB in the mutants was checked on Western blots (FIG. 5). The lbpA mutant CE1452 did not express LbpA (FIG. 5A, lane 4), and the lbpB mutant CE1454 did not express the 94 kDa protein (FIG. 5B, lane 6). This result confirms that the lbpB gene is indeed expressed in the wild-type strain, and that it encodes a protein with an M, of 94,000, which is considerably higher than its calculated molecular mass of 77.5 kDa. Furthermore, the results from FIG. 4 show that the inactivation of lbpB does not have a polar effect on LbpA expression (FIG. 5A, lane 6). This was anticipated, since the kanamycin resistance cassette that was inserted in lbpB does not contain a transcriptional terminator. The previously described spontaneous lbpA mutant CE 1402 (Pettersson et al, 1994b) appeared to lack LbpB expression as well (FIG. 5B, lane 8). Since both this mutant and BNCV are derivatives of strain M986, its genetic background is the same as that of the other mutants. Expression of both LbpA and LbpB appeared to be iron-regulated (FIG. 5). A weak expression of LbpA was seen in strain CE1454 even when the cells were grown without an iron chelator (FIG. 5A, lane 5). This expression is probably due to transcription from the promoter of the kanamycin resistance gene in lbpB. However, also in this case, the expression of the LbpA was increased severalfold when the strain was grown in the presence of an iron chelator (FIG. 5A, lane 6).

Example 6

6A: Lactoferrin Binding Assay

Lactoferrin binding to whole cells was assessed in an ELISA-type assay. Recombinant human lactoferrin, produced in *Aspergillus avamori*, was kindly provided by Agennix Inc., Houston, Tex., USA. The lactoferrin was saturated with iron as described (van Berkel et al., 1995), with the following modifications. FeCl$_3$ was used instead of Fe(NO$_3$)$_3$, and the dialysis was done against 5 mM Na$_2$HPO$_4$/NaH$_2$PO$_4$-buffer, pH 7.7 for 4 h. Colonies from plates were suspended in Tris-buffered saline, pH 7.5 (TBS) and killed by heating for 30 min at 56° C. Samples (100 µl) with an optical density at 620 nm of 0.05 were dispensed into the wells of a microtiter plate. The samples were allowed to dry overnight at 37° C. The assay was carried out at 37° C. Nonspecific binding was prohibited with 100 µl of blocking solution containing 0.5% Protifar (Nutricia) and 0.1% Tween 20 in TBS for 1 h. After blocking, the wells were filled with various concentrations of lactoferrin in blocking solution. The concentration of lactoferrin in the wells varied from 3.125 to 200 ng/ml. After incubation for 1 h, and three washes with tap water, a peroxidase-coupled rabbit polyclonal antiserum against human lactoferrin (ICN Biomedicals) was added to the wells. The antibody was used at a dilution of 1:5000 in blocking buffer. After incubation for 1 h and three washes with tap water, the amount of peroxidase was detected (Abdillahi and Poolman, 1987).

Lactoferrin binding on a blot was performed as follows. Unspecific binding was blocked by incubating the membrane in 0.2 M Na$_2$HPO$_4$/NaH$_2$PO$_4$ buffer, pH 5.7 containing 0.1% Tween-20 and 0.5% Protifar (Nutricia) for 2 h. The blot was incubated with 1.2 µgml$^{-1}$ peroxidase-conjugated human lactoferrin (Pettersson et al., 1993) in blocking buffer for 1 h and washed three times with blocking buffer. The activity of the peroxidase was detected with the ECL system according to the instructions of the manufacturer (Amersham).

6B: Plate Feeding Assays

Meningococci were grown overnight in TSB supplemented with Vitox, as described in Example 1. Of the overnight culture, 300 µl were suspended in 3 ml of top agar (1% GC agar with 20 µg EDDA per ml, cooled down to 42° C.) and immediately plated on GC agar plates supplemented with Vitox and 20 µg EDDA per ml. Drops (10 µl) of recombinant human lactoferrin (11% iron saturated, or saturated as described above) were spotted on the plates. The concentration of lactoferrin in the drops was 10 and 20 mg/ml, respectively. Plates were grown overnight.

6C: Binding of Lactoferrin to Folded LbpB on Blots

Figure 6:
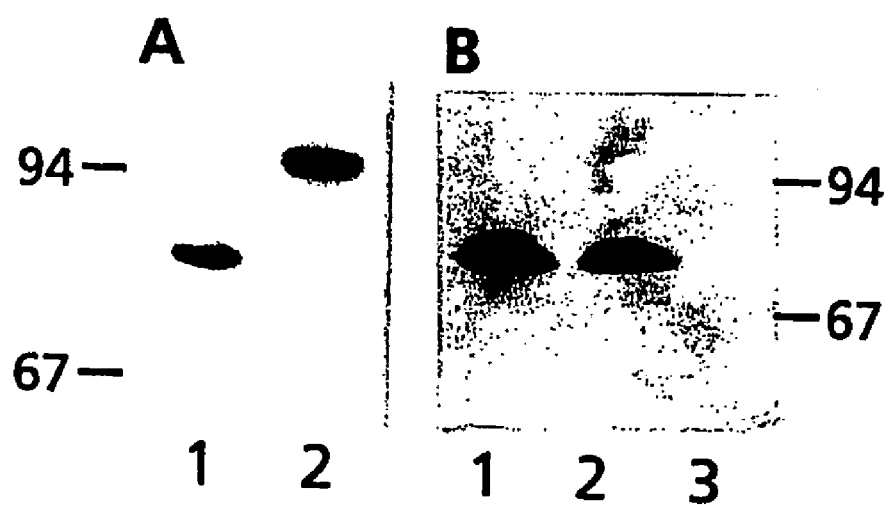
FIG. 6. A. Western blot analysis of proteins from outer membranes of the meningococcal strain BNCV grown under iron limitation. The outer membrane proteins were electrophoresed under non-denaturing conditions and the LbpB protein was detected with the serum directed against the synthetic peptide A1. Lanes 1 and 2 show samples incubated at 0° C. and 95° C., respectively prior to electrophoresis. The positions of the molecular size standards are indicated at the right in thousands. B. Lactoferrin binding assay on a Western blot with proteins from outer membrane complexes of the meningococcal strain BNCV grown under iron limitation. The proteins from the outer membrane complexes were electrophoresed under non-denaturing conditions and the blot was incubated with peroxidase-coupled human lactoferrin. Lanes 1 to 3 show samples incubated at 0° C., 37° C., and 95° C., respectively prior to electrophoresis. The positions of the molecular size standards are indicated at the right in thousands.

To investigate whether lactoferrin can bind to LbpB on blots, SDS-PAGE conditions were sought under which the LbpB is not denatured (see Example 6A). When samples were not heated in sample buffer prior to electrophoresis, a faster migrating form of the LbpB protein could be detected, probably representing the native, folded form of the protein (FIG. 6A). This form had an Mr of approximately 80 kDa. After heating for 10 min at 95° C., the LbpB protein was fully denatured and migrated at the 94 kDa position (FIG. 6A, lane 2). Interestingly, only the serum against the peptide A1 (FIG. 2) reacted with the faster migrating form of the protein. This peptide contains one of the two stretches, rich in negatively charged amino acids and possibly implicated in lactoferrin binding. The binding of the antibodies to the folded protein suggests that this part of the protein is exposed, whereas all other peptide epitopes are hidden in the folded structure of LbpB.

Binding of lactoferrin to the folded LbpB protein was subsequently assessed. Outer membrane proteins of strain BNCV were blotted to a nitrocellulose membrane, and were incubated with peroxidase-coupled human lactoferrin. The specificity of the lactoferrin binding appeared to be extremely sensitive to the incubation conditions, most importantly, the pH. Under optimized conditions, lactoferrin bound specifically to a protein band with a Mr of 80 kDa (FIG. 6B, lanes 1 and 2). No binding was observed when the samples were heated for 10 min at 95° C. prior to SDS-PAGE (FIG. 6B, lane 3). The band was not detected in the samples of the lbpB mutant CE 1454 (data not shown). Hence, it is concluded that the faster migrating form of the LbpB protein, probably representing the folded form of the protein, is capable of lactoferrin binding.

6D: Lactoferrin Binding and Utilisation in Whole Cells

Figure 7:
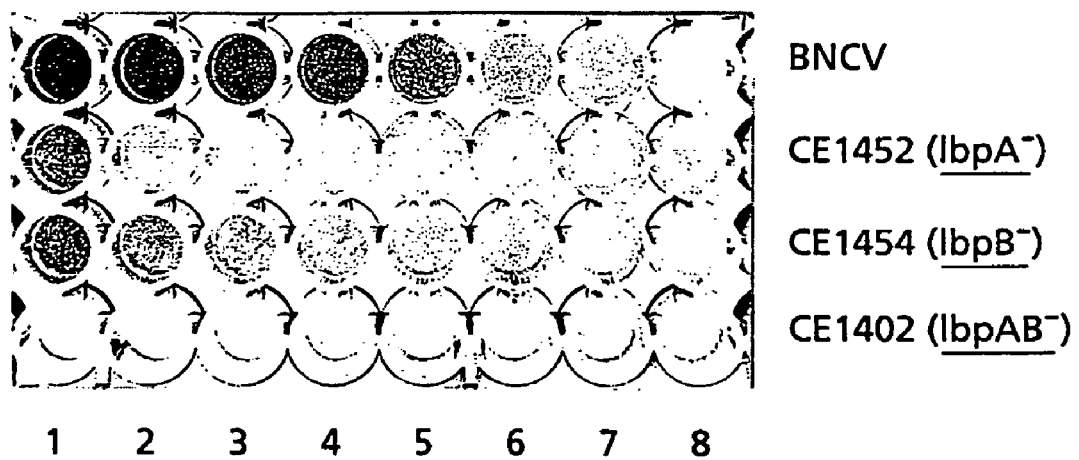
FIG. 7. Binding of lactoferrin to lbp mutants in whole-cell ELISA-type assay. Strains, indicated at the right, were coated to the wells. Lactoferrin was added in concentrations of 200, 100, 50, 25, 12.5, 6.25, 3.125, and 0 ng/ml (rows 1–8 respectively). Lactoferrin bound to the cells was detected with peroxidase-conjugated lactoferrin-specific antiserum.

Lactoferrin binding to whole cells was investigated in an ELISA-type assay. The ELISA plates were coated with whole cells of strain BNCV of the isogenic mutants, and lactoferrin, in various concentrations, was added to the wells. Binding of lactoferrin to the cells was probed with a peroxidase-conjugated antibody against human lactoferrin (FIG. 7). The lbpB mutant was slightly reduced in its ability to bind lactoferrin. The lbpA mutant bound lactoferrin less effectively that the lbpB mutant, whereas the double mutant bound virtually no lactoferrin at all (FIG. 7).

Figure 8:
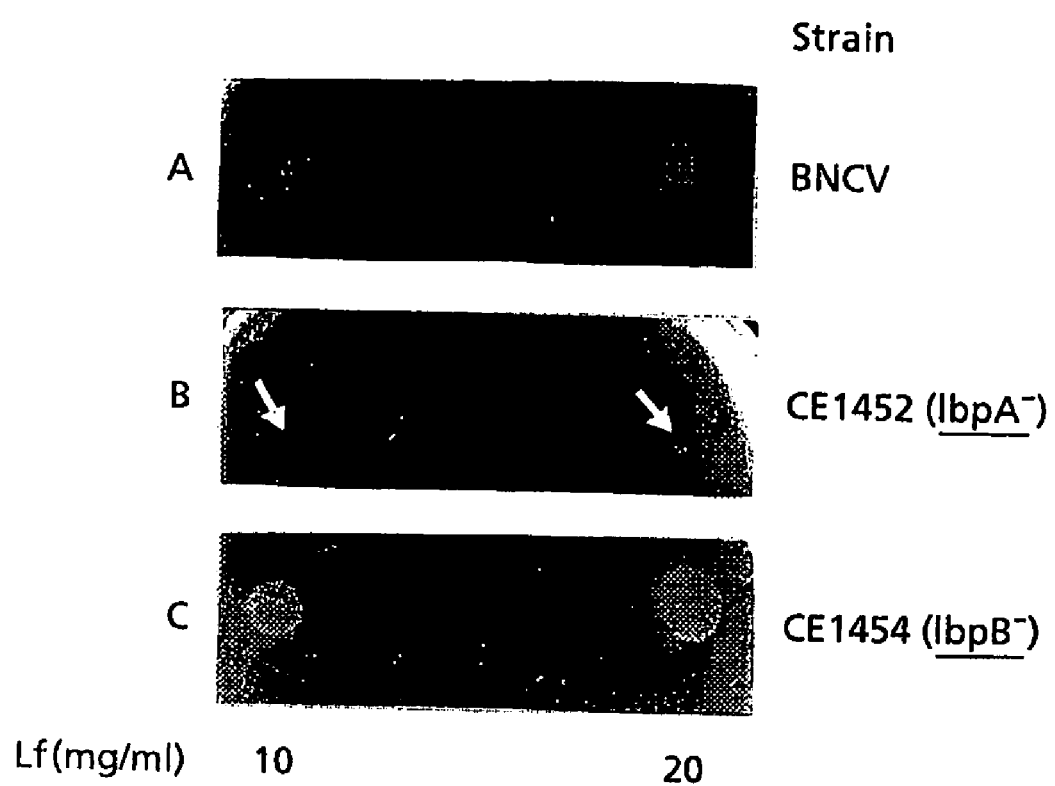
FIG. 8. Plate feeding assays of strains with recombinant human lactoferrin. Only the relevant part of the plate is shown. Cells of the strains indicated at the right were plated on iron-restricted plates. Growth stimulation by drops of lactoferrin at the concentrations indicated was monitored after overnight growth. Arrows show the position of the drops in Panel B. In this experiment, 11% iron-saturated lactoferrin was used.

The ability to use lactoferrin as a sole source of iron was investigated in plate feeding assays. Meningococci were grown under iron limitation on plates, drops of recombinant human lactoferrin were spotted on the plates, and growth stimulation was monitored. The lbpB mutant was able to grow on lactoferrin, whereas the lbpA mutant was not (FIG. 8). The lactoferrin was 11% iron saturated. The same experiment was performed with iron-loaded lactoferrin with essentially the same results (data not shown). These data demonstrate that the LbpA protein is necessary for iron uptake via lactoferrin, whereas LbpB does not seem to be essential.

Example 7

To study the variability of the meningococcal LbpB protein, the lbpB genes from four further strains were sequenced: H44/76, M990, M981, 881607 (see Table 1).

7A: Sequencing of lbpB from Four Further Meningococcal Strains—Methods

Bacteria were cultured in the same way as described in Example 1. Chromosomal DNA was isolated from bacteria grown on plates. After overnight growth, bacteria were scraped from the plates and suspended in 1.5 ml 10 mM Tris-HCl, 10 mM EDTA, pH 8 and 10 µl of lysozyme (10 mg/ml) was added. The suspension was incubated for 15 min at room temperature, before 1.5 ml of 2% Triton X-100, 50 mM Tris-HCl, 10 mM EDTA, pH 8 was added. After 15 min incubation, 10 µl of proteinase K (10 mg/ml) was added. The tubes were incubated for 30 min at room temperature. The mixture was extracted once with phenol, chloroform, isoamylalcohol (mixed in ratio 24:24:1), and once with chloroform saturated with water. The chromosomal DNA was precipitated with ethanol.

Chromosomal DNA was used to PCR amplify the lbpB genes. Primers LB20 and REV2 (Table 3) were used on strains H44/76, M990, and 881607. Primers LB20 and LB23 were used on strain M981. The primers are based on the sequence of lbpB from strain BNCV. LB20 binds upstream of the lbpB gene, and LB23 and REV2 at the beginning of the lbpA gene. LB23 has an extra BamHI site at the 5' end. Goldstar polymerase, a Taq polymerase derivative (Eurogentec) was used for PCR amplifications according to the instructions from the manufacturer. The annealing temperature was in all cases 50° C., and 30 cycles were performed. PCR products were purified from agarose gels, using β-agarase (New England Biolabs) according to the instructions of the manufacturer.

DNA sequencing was performed by gene walking using primers designed for the lbpB genes. Primers were synthesized by Gibco BRL. Sequencing was done automatically using the ABI Prism 310 Genetic Analyser (Perkin-Elmer). The labelling was done with the Dye Terminator Cycle Sequencing Kit (Perkin-Elmer).

The computer programs TRANSL, PALIGN and CLUSTAL from the software package PC Gene 6.70 (IntelliGenetics) were used to translate the nucleotide sequence into amino acid sequence, for pairwise alignment of sequences and for multiple alignment, respectively.

7B: Sequencing of lbpB from Four Further Meningococcal Strains—Results

The nucleotide sequences of the lbpB genes of the four strains are shown in SEQ ID NO:3, 5, 7, and 9. The nucleotide sequences were translated into amino acid sequences and an alignment of the five known sequences of the LbpB proteins is presented in FIG. 9. On the amino acid level, the identity between the LbpB proteins of the different strains was 70–80%. A pairwise comparison of identities is summarized in Table 4.

Example 8

The expression level of LbpB in *Neisseria meningitidis* is very low; the protein could not be detected when outer membrane protein patterns were analysed by SDS-PAGE. For immunological and structural/functional studies of the LbpB protein, a construct was made for expression of the protein in *Escherichia coli*. To facilitate purification of the recombinant protein, the protein encoded by the construct contained a His-tag, and lipid modification of the N terminus was prevented by replacement of the native signal sequence and first two amino acid residues of the mature domain.

8A: Expression of Recombinant LbpB—Bacterial Strains and Growth Conditions

The meningococcal strain BNCV (-:2a:P1.2) was cultured overnight on GC agar plates (Difco), supplemented with Vitox (Oxoid) in a humid 5% $CO_2$ atmosphere at 37° C. The construct encoding the recombinant LbpB protein was expressed in the *E. coli* strain CE1448 (generously provided by C. Jansen), which is a htrA ompT derivative of strain CE1224 (Tommassen et al., 1983). The strain was grown at 37° C. in a Hepes-buffered synthetic medium (Tommassen and Lugtenberg, 1980) supplemented with growth requirements due to auxotrophic mutations and with 1.32 mM $K_2HPO_4$ (phosphate-replete conditions). After overnight growth, the culture was diluted 1:13.5 into the same medium, but without $K_2HPO_4$ (phosphate-depleted conditions) and grown for 6 h at 37° C.

8B: Expression of Recombinant LbpB—Cloning in *E. coli*

Chromosomal DNA was isolated from meningococcal cells grown overnight on plates. Bacteria were scraped from the plates, suspended in 1.5 ml 10 mM Tris-HCl, 10 mM EDTA, pH 8, and 10 µl of lysozyme (10 mg/ml) was added. The suspension was incubated for 15 min at room temperature, before 1.5 ml of 2% Triton X-100, 50 mM Tris-HCl, 10 mM EDTA, pH 8 was added. After 15 min incubation, 10 pi of proteinase K (10 mg/ml) was added. The tubes were incubated for 30 min at room temperature. The DNA was extracted from the mixture by adding phenol/chloroform/isoamylalcohol (24:24:1 by volume), and further purified by extraction with chloroform saturated with water. The chromosomal DNA was precipitated with ethanol.

Figure 10:
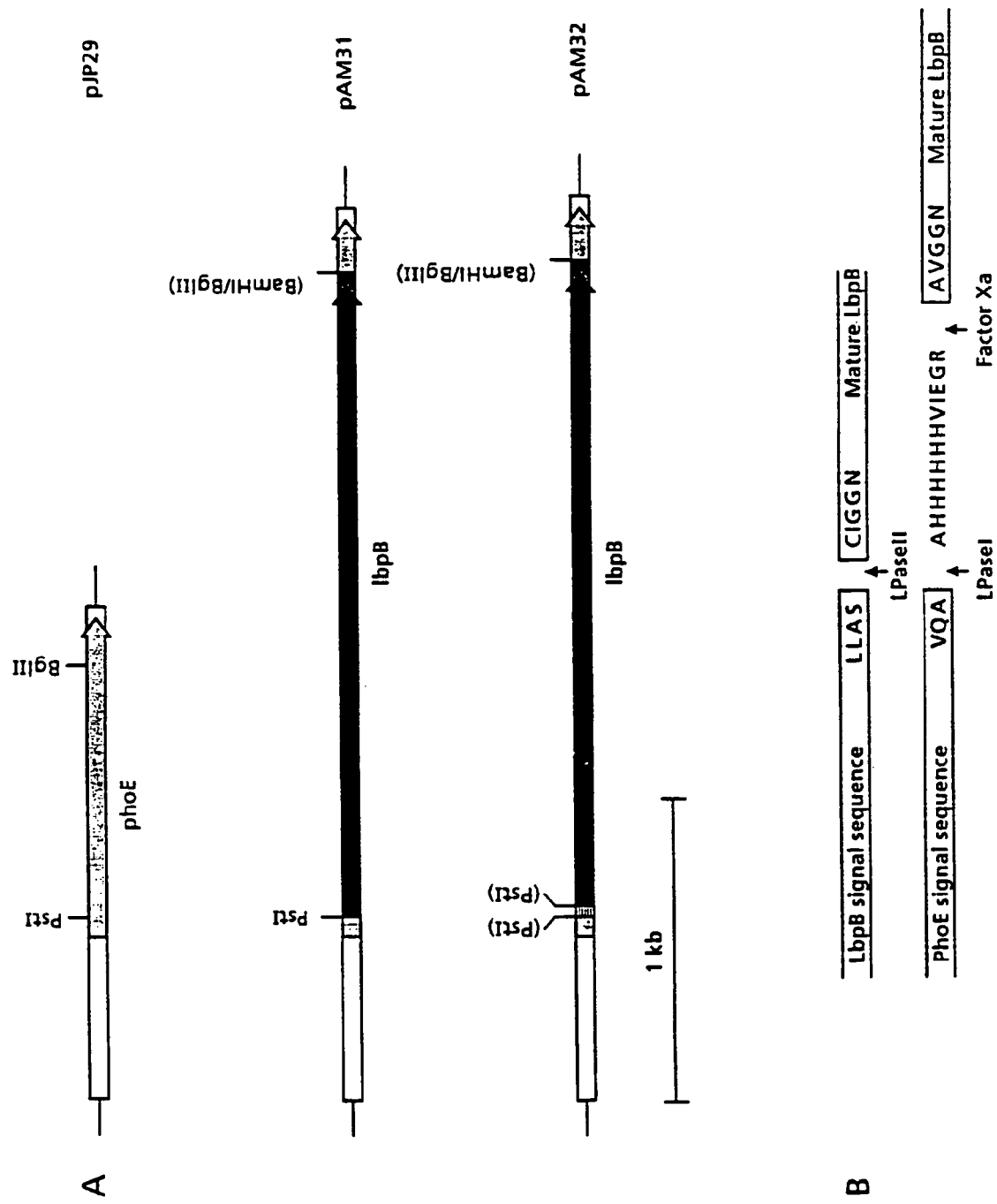
FIG. 10. A. Restriction maps of the relevant parts of pJP29 (Bosch et al., 1986), pAM31 and pAM32. Only the inserts are shown. The vector is pACYC 184. pJP29 contains the phoE gene (in light grey) behind its own promoter. The promoter and flanking sequences are in white. The PstI-site is at the border of the sequences corresponding to the signal sequence and the mature part of the PhoE protein. pAM31 contains, from left to right: The phoE promoter (in white), and a recombinant gene encoding the signal sequence of PhoE (light grey) and the mature LbpB (black). DNA fragments corresponding to the N terminus of LbpA (dark grey), the C terminus of PhoE (light grey), and flanking sequences (white) are present as well. pAM32 was constructed from pAM31 by inserting a linker (striped box), encoding a His-tag and a Factor Xa cleavage site, into the PstI-site of pAM31. See Example 8 for details about the construction of pAM31 and pAM32. The restriction sites on pAM32 are in brackets, because they are lost during the cloning procedure.

The chromosomal DNA was used as a template to amplify the part of the lbpB gene corresponding to the mature LbpB by PCR using primers LB22 and LB23 (Table 5). LB22 primes at a site corresponding to the N-terminal part of LbpB and introduces a PstI-site in the PCR product. LB23 primes just downstream of lbpB at the beginning of the lbpA gene and introduces a BamHI-site. Pwo polymerase (Boehringer Mannheim), a proof-reading enzyme, was used in the PCR reaction, according to the instructions provided by the manufacturer. The annealing temperature was 60° C., and 30 cycles were performed. The PCR product was isolated from a gel, using β-agarase (New England Biolabs) according to the manufacturer's instructions. The PCR product was digested with PstI and BamHI and ligated into pJP29 (FIG. 10A), which had also been digested with PstI and BglII. In the resulting construct, pAM31, the BamHI and BglII sites are lost. The LbpB protein is expressed in this construct from the phoE promoter and contains the PhoE signal sequence instead of the authentic signal sequence. Furthermore, the first two residues from the N-terminus were changed from Cys and Ile to Ala and Val, respectively. To facilitate the purification of the protein, a His-tag was inserted between the signal sequence and the mature part of LbpB. pAM31 was digested with PstI and ligated to a linker composed of the oligonucleotides VGO12a and VGO13a (Table 5), resulting in plasmid $pAM^{32}$ (FIG. 10A). The PstI-site is lost after ligation. The linker codes for six His residues and a factor Xa cleavage site (FIG. 10B).

8C: Purification of Recombinant LbpB

The recombinant LbpB was produced in strain CE1448 containing pAM32. Phosphate-limited cells from a 5 liter culture were harvested after 6 h of growth. Cells were washed once with 500 ml physiological salt solution and resuspended in 150 ml of 10 mM Tris-HCl, 5 mM EDTA, pH 8. The suspension was frozen at −20° C. overnight. The cells were thawed and three protease inhibitor cocktail tablets (Complete™, Boehringer Mannheim) were added. The cells were pressed twice through a French press at a pressure of 8000 psi. Unbroken cells were removed by centrifugation in a Sorvall GSA rotor at 5000 rpm for 20 min. The supernatant was centrifuged in a Beckman Ti60 rotor at 40,000 rpm for 90 min. The cell envelopes were dissolved in 5 mM $Na_2HPO_4$—$NaH_2PO_4$— buffer, pH 7.6.

The cell envelopes were extracted twice with 2% n-octyl-oligo-oxyethylene (Octyl-POE) at 37° C. The first extraction was done for 1 h, and the second for 3 h. In between and after the extractions, non-soluble proteins were pelleted by centrifugation in a Beckman TLA100.2 rotor at 100,000 rpm for 1 h. Supernatants, containing the LbpB protein, were combined and added to Ni-NTA agarose. Purification of the protein was done in batch under native conditions, according to the instructions provided by the manufacturer (Qiagen). The concentrations of imidazole and NaCl were 20 mM and 300 mM, respectively, during binding and washing. In total, 2 ml of Ni-NTA agarose was used, divided over 10 tubes. Elution was performed in steps with 3 ml of 100 mM, 200 mM, and 250 mM imidazole, respectively. After elution, the protein was dialyzed twice in a Spectra/Por 2 dialysis bag (Spectrum) against 2.5 l of phosphate-buffered saline. The protein was concentrated in a Fugisept Maxi Centrifugal Concentrator (Intersept) with a cut-off of 10 kDa. The centrifugation was performed in a Sorvall GSA rotor at 5000 rpm, until the total volume was 1–1.5 ml.

Polyacrylamide gel electrophoresis (PAGE) was performed as described by Lugtenberg et al. (1975) with a few modifications. The polyacrylamide gel was composed of a 5% stacking gel and an 11% resolving gel, containing no SDS. When denaturation of LbpB had to be prevented, the sample buffer (Lugtenberg et al., 1975) contained no α-mercaptoethanol, and the samples were kept at 0° C. before PAGE. To denature LbpB, the sample buffer was supplemented with P-mercaptoethanol, and the samples were boiled for 5 min. Electrophoresis was carried out at a constant current of 20 mA at 4° C. The gel was stained with Coomassie Brilliant Blue.

8D: Expression and Purification of Recombinant LbpB—Results

A recombinant form of LbpB of *N. meningitidis* strain BNCV was expressed in the *E. coli* strain CE1448. A construct, pAM32, was made encoding a recombinant protein consisting of the signal sequence of PhoE, a His-tag and the mature LbpB protein (FIG. 10A). The protein is expressed from the phoE promoter under phosphate limitation. The authentic type II signal sequence of LbpB is replaced by a type I signal sequence, and a His-tag followed by a Factor Xa cleavage site is inserted between the signal sequence and the mature LbpB. Furthermore, the first two amino acids of the mature LbpB, Cys and Ile were changed into Ala and Val (FIG. 10B). Consequently, the recombinant protein cannot be lipid-modified at an N-terminal Cys. The recombinant LbpB protein fractionated with the membranes, and not with the soluble proteins (data not shown). Therefore, it had to be extracted from the membrane with a detergent. Octyl-POE was used because it solubilized about 50% of the total amount of recombinant LbpB from the membrane. Furthermore, when the extracted protein is not denatured by boiling in sample buffer, it migrates faster in PAGE than the denatured protein (data not shown), suggesting that the protein was correctly folded. After extraction, the His-tagged protein was purified by Ni-affinity chromatography. Most of the protein eluted in the 100 mM and 200 mM imidazole fractions. However, all fractions were combined before dialysis. The protein was pure as evaluated on a Coomassie Brilliant Blue-stained gel (FIG. 11), and most of it was present in the folded form, which migrates faster during PAGE than the denatured form. The folded form of LbpB, but not the denatured form, was shown in Example 6 to bind lactoferrin on a blot.

Example 9

To study the immunogenicity of the LbpB protein in man, the presence of antibodies recognizing the LbpB protein of strain BNCV in human convalescent sera was tested in immunoblots.

9A: Immunogenicity of LbpB in Man—Methods

Ten human convalescent sera were obtained from Smith-Kline Beecham Biologicals SA, Belgium, and seven sera from the National Institute of Public Health and the Environment, The Netherlands (Table 6). The individuals had been infected with strains of various sero- and subtypes Recombinant LbpB was isolated using the procedure described in Example 8. Polyacrylamide gel electrophoresis (PAGE) was performed as described by Lugtenberg et al. (1975) with a few modifications. The polyacrylamide gel was composed of a 5% stacking gel and an 11% resolving gel, containing no SDS. When denaturation of LbpB had to be prevented, the sample buffer (Lugtenberg et al., 1975) contained no β-mercaptoethanol, and the samples were kept at 0° C. before electrophoresis. To denature LbpB, the sample buffer was supplemented with P-mercaptoethanol, and the samples were boiled for 5 min. Electrophoresis was carried out at a constant current of 20 mA at 4° C.

Immunoblotting was performed as described by Pettersson et al. (1993). Human sera were diluted 1:500. Peroxidase-conjugated rabbit anti-human IgG (Dako A/S) was used as the secondary antibody at a working dilution of 1:5000. The activity of the peroxidase was detected with the ECL system according to the instructions provided by the manufacturer (Amersham).

9B: Immunogenicity of LbpB in Man—Results

The presence of LbpB specific antibodies in human sera was tested against purified, recombinant LbpB protein of strain BNCV (-:2a:P1.2) in immunoblots. Reactivity was tested both against the folded LbpB and against the denatured protein (see FIG. 12 for examples). The results are summarized in Table 6. Four of the sera reacted strongly with both the denatured and folded form of LbpB. Five sera reacted weakly with both forms, two sera weakly with only the folded form, two sera weakly with only the denatured form, and four sera did not react with LbpB at all. These results demonstrate that the meningococcal LbpB is immunogenic in man and suggest a considerable degree of immunological cross-reactivity between LbpB proteins from various strains.

Example 10

ELISA & Bactericidal Tests Using Sera Obtained from Mice Immunised With Meningococcal Cells or LbpB 10A: Immunization Protocol Immunization with *N. meningitidis* strain BNCV: Groups of 10 mice (6 weeks old Balb/C) were immunized (100 µl intraperitoneal or 100 µl subcutaneous) three times with $5 \times 10^8$ CFU of heat inactivated BNCV whole cells in SBAS2 adjuvant. The three immunizations were carried out 21 days apart, and blood was drawn on day 56 by intra cardiac punction. Sera were pooled by group.

Immunization with LbpB from *N. meningitidis* strain BNCV: This was done by the same method as above except that the 2 first immunizations were done with 10 µg of crude LbpB (*E. coli* cell envelope containing the recombinant LbpB) and the third immunization was carried out with 2.5 µg of pure LbpB (prepared in the same way as described in Example 8).

10B: Measurement of the Response in Whole Cell ELISA (WCE) and Purified LbpB ELISA Flat-bottomed, 96-well Nunc immuno plates were used. 100 µl of a heat inactivated *Neisseria meningitidis* B strain [that had been grown under conditions of iron depletion conditions (fe-) using EDDA as described in Example 1] (20 µg/ml total protein) suspension in PBS was aliquotted into individual wells of plates and allowed to evaporate overnight at 37° C.

The coated plates were washed four times with 0.9% NaCl, 0.05% Tween 20 and were saturated with PBS Casein 0.3% (Merck) for 30 minutes at room temperature with stirring, and washed in the same way. 100 µl of pooled sera were 100 fold diluted in PBS Tween 20 0.05% casein 0.1%, added to the first well, then 2 fold diluted up to 12 dilutions and plates were then incubated for 30 minutes at 37° C. with stirring. After washing, 100 µl of a 2000 fold dilution of Rabbit anti-mouse Immuno-globulins biotin (Dakopatts E0413) in PBS tween 20 0.05% Casein 0.3% were added and the plates were incubated in the same way as before. Plates were washed and then 100 µl of a 4000 fold dilution in PBS tween 20 0.05% of Streptavidin-biotinylated horseradish peroxidase complex were added and the plates were incubated in the same way. After washing, 100 µl of a freshly prepared solution of 4 mg O-phenyldiamine (OPDA) stain (sigma P8787) in 0.1 M citrate buffer pH 4.5 were added and plates were incubated for 15 minutes at room temperature in a dark room. The reaction was stopped by adding 50 µl 1N HCl. The absorbances were read at 490 nm.

Anti-LbpB ELISA works in the same way as WCE except the coating is different. The wells were coated with 100 µl of a solution of 0.5 µg/ml pure LbpB in 0.05 M carbonate/bicarbonate buffer pH 9.6 and incubated overnight at 37° C. (not evaporated).

10C: Bactericidal Assay

A culture of group B meningococci (strain H44176) [grown either under conditions of iron depletion (fe-) as described in Example 1, or under iron rich (fe+) conditions by omitting the addition of EDDA] in the log phase of growth (OD-0.3) was suspended in sterile Hanks medium with 0.3% BSA in order to obtain a working cell suspension adjusted to 20000 CFU/ml.

A primary reaction mixture (75 µl) was made containing 5011/well of two-fold dilutions of test serum (Example 10A) samples (that had been heat-inactivated at 56° C. for 30 min) and 25 µl/well of the 20000 CFU/ml log phase group B meningococci. The reaction vials were incubated at 37° C. for 15 minutes and shaked at 210 rpm. The final reaction mixture (100 µl) additionally contained 25% pretested baby rabbit serum as a complement source, and was incubated under the same conditions for 60 min. A sterile polystyrene U-bottom 96-well microtiter plate was used for this assay.

A 10 µl aliquot was taken from each well using a multichannel pipette, and was dropped onto Mueller-Hinton agar plates containing 1% Isovitalex and 1% heat-inactivated Horse Serum and incubated for 18 hours at 37° C. in 5% $CO_2$. Individual colonies could be counted up to 80 CFU per aliquot.

The following three test samples were used as controls: buffer+bacteria+complement; buffer+bacteria+inactivated complement; serum+bacteria+inactivated complement.

Titers were calculated using a procedure with the program Excel (Microsoft). This procedure gives a precise measurement of the dilution which corresponds to 50% of cell killing by a regression calculation.

Example 10D

Results

Table 7 and FIG. 13 show that immunization with LbpB induces a good response against LbpB (FIG. 13A), as well as against whole cell samples from strain BNCV (the source of the recombinant LbpB) AND strain H44/76 (the LbpB of which having only 78.5% sequence identity with that of BNCV) (FIGS. 13B and C). Sera obtained using an immunization schedule involving only recombinant LbpB gave a similar result (data not shown). Clearly, anti-whole cell immunization with strain BNCV leads to higher anti-whole cell ELISA for both BNCV cells and H144/76 cells (FIGS. 13B and C, respectively).

In addition, immunization with recombinant LbpB from N meningitidis strain BNCV induces antibodies that bind to a protein of similar molecular weight in whole cell samples from *Moraxella catarrhalis* run on an immunoblot carried out substantially as described in Example 9 (data not shown).

Table 8 and FIG. 14 show that the antibodies produced in the sera after immunization with recombinant LbpB (from strain BNCV) are bactericidal against a heterologous strain (H44/76), the LbpB of which having only 78.5% sequence identity with that of BNCV. This was also the case using sera obtained after an immunization schedule involving only recombinant LbpB (data not shown). This is true when the H44/76 has been grown in conditions containing iron (FIG. 14A) and depleted in iron (FIG. 14B). There seems to be a greater effect in conditions of iron depletion as might be expected if LbpB is expressed in greater amounts when the bacterium is under these conditions.

LbpB is therefore an immunoprotective antigen, and, furthermore, it shows evidence of providing cross-immunoprotection against heterologous strains of *N. meningitidis*.

TABLE 1

Bacterial strains and plasmids used.

| Strain | Description[a] | Reference/Source |
|---|---|---|
| *N. meningitidis* | | |
| H44/76 | B:15:P1.7,16 | E. Holten |
| CE1449 | H44/76 lbpA::Erm[r] | This application |
| BNCV | -:2a:P1.2 Nonencapsulated derivative of M986 | E. C. Gotschlich |
| CE1452 | BNCV lbpA::Erm[r] | This application |
| CE1452 | BNCV lbpB::Km[r] | This application |
| CE1402 | M986 lbpA, lbpB | Pettersson et al. 1994a |
| M990 | B:6:P1.6 | |
| 881607 | B:nt:P1.12 | |
| B16B6 | B:2a:P1.2 | A. Schryvers |
| N91 | B16B6 tbpB | A. Schryvers |
| M981 | B:4:nt | |
| *E. coli* | | |
| DH5α | | Laboratory stock |
| Y1090 | Amp[r] | Young and Davis, 1983 |
| PC2494 | hsdR derivative of JM101 | Phabagen Collection |

TABLE 1-continued

Bacterial strains and plasmids used.

| Strain | Description[a] | Reference/Source |
|---|---|---|
| Plasmids | | |
| pEMBL19 | Amp[r] | Laboratory stock |
| pUC4K | Km[r]-box, Amp[r] | Pharmacia Biotech |
| pER2 | Erm[r]-box in pBluescript, Amp[r] | Jennings et al., 1993 |
| pAM6 | pEMBL19 carrying parts of lbpA and lbpB | This application |
| pAM6K | pAM6 with a Km[r]-box from pUC4K inserted in the BgℓII site of lbpB | This application |
| pAM6K-nus | pAM6K with a neisserial uptake sequence inserted in the KpnI-site of the multiple cloning site of the vector | This application |
| pAM13 | pEMBL19 carrying parts of lbpA and lbpB | This application |
| pAM1 | pUC19 carrying parts of lbpA and lbpB | Pettersson et al. 1993 |
| pAM23 | pUC19 carrying lbpA and part of lbpB | Pettersson et al. 1994b |
| pAM23E | pAM23 with an Erm[r]-box inserted in the EcoRV-site of lbpA | This application |

[a]Serogroup, serotype and subtype are mentioned.
nt: non typable.

TABLE 2

Primers used for PCR or linker cloning

| Name | Sequence | Remarks |
|---|---|---|
| DVAS2 | AGACCGACCCTTCGACGACTTCGG | |
| FW5 | GAAGAAGAAGCGATGGTGCGG | |
| SDA1 | CCTCTTTAGTATCTTTCTTCGCAC | |
| LB11 | CTTAATTTCATCTTTTCCC | |
| PR1 | GAGCGAGTCCGCGTTAGTGCT | Binds in Km[r] - cassette |
| nus1 | TTCAGACGGCTGTAC | Neisserial uptake sequence complementary to nus1 |
| nus2 | AGCCGTCTGAAGTAC | |

TABLE 3

Primers used to PCR amplify the four further lbpB genes

| Name | Sequence |
|---|---|
| LB20 | GGAGGAAAAGTAGGGATG |
| LB23 | CGGGATCCAGCCAAGGCAGTCAGGGTAAGC |
| REV2 | GCACGGACGGTAACCTCTTTCAGG |

TABLE 4

Pairwise identities of the LbpB sequences, in %

|  | H44/76 | M990 | M981 | 881607 |
|---|---|---|---|---|
| BNCV | 78.5 | 73.8 | 72.7 | 71.4 |
| H44/76 |  | 72.5 | 74.1 | 78.5 |
| M990 |  |  | 70.5 | 71.3 |
| M981 |  |  |  | 80.6 |

TABLE 5

Primers used to express recombinant LbpB

| Name | Sequence |
|---|---|
| LB22 | AACTGCAGTCGGCGGCAATTTCGGCGTGCA |
| LB23 | CGGGATCCAGCCAAGGCAGTCAGGGTAAGC |
| VGO12a | CACCACCACGACCACCACGTGATCGAGGGGCGTGCA |
| VGO13a | CGCCCCTCGATCACGTGGTGGTGGTGGTGTGCA |

TABLE 6

Results of the immunoblot of human sera against purified LbpB.

| Serum | Characteristics[a] | Native[b] | Denatured[b] | Source[c] |
|---|---|---|---|---|
| 262439 | B:NT:P1.4 | + | + | SKB |
| 262532 | B:15:P1.7,16 | + | + | SKB |
| 262658 | B:NT:P1.15 | − | − | SKB |
| 262716 | B:15:P1.7,16 | − | + | SKB |
| 262892 | B:2b:P1.10 | ++ | ++ | SKB |
| 262917 | B:4:NT | ++ | ++ | SKB |
| 262941 | B:1:P1.15 | + | + | SKB |
| 262987 | B:2a:P1.15 | + | + | SKB |
| 263017 | B:4:NT | − | − | SKB |
| 263021 | B:4:P1.4 | − | − | SKB |
| 69 | B:15:P1.16 | + | − | RIVM |
| 322 | B:15:P1.5 | + | − | RIVM |
| 329 | B:1:P1.4 | − | − | RIVM |
| 330 | B:1:P1.4 | ++ | ++ | RIVM |
| 187 | — | − | + | RIVM |
| 195 | — | ++ | ++ | RIVM |
| 118 | — | + | + | RIVM |

[a]Sero- and subtypes of the strain with which the patient was infected are indicated, when known.
NT: not typable.
[b]++ indicates strong reaction, + weak reaction and − no reaction with the native or denatured form of the protein.
[c]SKB: SmithKline Beecham Biologicals, RIVM: National Institute of Public Health and the Environment.

TABLE 7

Results of the anti Whole Cell and anti-LbpB ELISA performed as described in Example 10 anti-LbpB response

|  | 100[a] | 200 | 400 | 800 | 1600 | 3200 | 6400 | 12800 | 25600 | 51200 | 102400 | 204800 |
|---|---|---|---|---|---|---|---|---|---|---|---|---|
| BNCV | 0.341[b] | 0.196 | 0.107 | 0.063 | 0.033 | 0.018 | 0.014 | 0.011 | 0.013 | 0.012 | 0.009 | 0.012 |
| LbpB | 2.772 | 2.918 | 2.794 | 2.867 | 2.687 | 2.487 | 2.046 | 1.504 | 1.043 | 0.668 | 0.405 | 0.202 |
| PBS | 0.14 | 0.079 | 0.044 | 0.028 | 0.016 | 0.018 | 0.012 | 0.01 | 0.01 | 0.008 | 0.012 | 0.01 | anti BNCV(Fe−) response

|  | 100 | 200 | 400 | 800 | 1600 | 3200 | 6400 | 12800 | 25600 | 51200 | 102400 | 204800 |
|---|---|---|---|---|---|---|---|---|---|---|---|---|
| BNCV | 2.476 | 3.09 | 3.04 | 3.154 | 3.034 | 3.112 | 3.111 | 2.905 | 2.745 | 2.436 | 1.659 | 1.056 |
| LbpB | 1.783 | 1.856 | 1.292 | 0.914 | 0.622 | 0.385 | 0.257 | 0.185 | 0.122 | 0.106 | 0.096 | 0.089 |
| PBS | 0.687 | 0.55 | 0.358 | 0.243 | 0.154 | 0.123 | 0.099 | 0.088 | 0.083 | 0.081 | 0.031 | 0.081 | anti H44/76(Fe−) response

|  | 100 | 200 | 400 | 800 | 1600 | 3200 | 6400 | 12800 | 25600 | 51200 | 102400 | 204800 |
|---|---|---|---|---|---|---|---|---|---|---|---|---|
| BNCV | 2.814 | 3.003 | 2.966 | 2.976 | 2.873 | 2.66 | 2.371 | 1.862 | 1.312 | 0.873 | 0.591 | 0.452 |
| LbpB | 2.653 | 2.287 | 1.683 | 1.123 | 0.748 | 0.536 | 0.409 | 0.35 | 0.309 | 0.298 | 0.289 | 0.295 |
| PBS | 1.646 | 1.049 | 0.695 | 0.47 | 0.338 | 0.271 | 0.238 | 0.226 | 0.226 | 0.251 | 0.284 | 0.285 |

[a]Sera dilution.
[b]Optical density at 490 nm.

TABLE 8

Results of the bactericidal activities of anti Whole Cell and anti-LbpB sera performed as described in Example 10

| | Bactericidal titer against H44/76(Fe−) | | | | | | | |
|---|---|---|---|---|---|---|---|---|
| | 200.0[a] | 400.0 | 800.0 | 1600.0 | 3200.0 | 6400.0 | 12800.0 | 25600.0 |
| H44/76 | 100.0 | 100.0 | 100.0 | 100.0 | 100.0 | 100.0 | 100.0 | 97.2 |
| BNCV | 100.0 | 94.4 | 93.0 | 83.2 | 81.8 | 63.7 | 48.3 | 34.4 |
| LbpB | 10.6 | −0.5 | −0.5 | −0.5 | −0.5 | −0.5 | −0.5 | −0.5 |
| PBS | −0.5 | −0.5 | −0.5 | −0.5 | −0.5 | −0.5 | −0.5 | −0.5 |

| | Bactericidal titer against H44/76(Fe+) | | | | | | | |
|---|---|---|---|---|---|---|---|---|
| | 200.0 | 400.0 | 800.0 | 1600.0 | 3200.0 | 6400.0 | 12800.0 | 25600.0 |
| H44/76 | 100 | 98 | 100 | 100 | 100 | 100 | 100 | 98 |
| BNCV | 100 | 98 | 96 | 85 | 83 | 70 | 64 | 32 |
| LbpB | 34 | 25 | 0 | 0 | 0 | 0 | 0 | 0 |
| PBS | 0 | 0 | 0 | 0 | 0 | 0 | 0 | 0 |

[a]Sera dilution.

All publications, including but not limited to patents and patent applications, cited in this specification are herein incorporated by reference as if each individual publication were specifically and individually indicated to be incorporated by reference herein as though fully set forth.

BIBLIOGRAPHY

Abdillahi, H., and Poolman, J. T. (1987) Whole-cell ELISA for typing of Neisseria meningitidis with monoclonal antibodies. FEMS Microbiol. Lett 48: 367–371.

Anderson, J. E., Sparling, P. F., and Cornelissen, C. N. (1994) Gonococcal transferrin-binding protein 2 facilitates but is not essential for transferrin utilization. J Bacteriol 176: 3162–3170.

Ausubel, F. M., Brent, R., Kingston, R. E., Moore, D. M., Seidman, J. G., Smith, J. A., and Struhl, K. (1989) Current protocols in molecular biology. Brooklyn, N.Y.: Greene Publishing Associates.

Bagg, A., and Neilands, J. B. (1987) Ferric uptake regulation protein acts as a repressor, employing iron (II) as a cofactor to bind the operator of an iron transport operon in Escherichia coli. Biochemistry 26: 5471–5477.

Biswas, G. D., and Sparling, P. F. (1995) Characterisation of lbpA, the structural gene for a lactoferrin receptor in Neisseria gonorrhoeae. Infect Immun 63: 2958–2967.

Bosch, D., Leunissen, J., Verbakel, J., de Jong, M., van Erp, H., and Tommassen, J. (1986) Periplasmic accumulation of truncated forms of outer membrane PhoE protein of Escherichia coli K-12. J. Mol. Biol. 189:449–455.

Cornelissen, C. N., Biswas, G. D., Tsai, J., Paruchuri, D. K., Thompson, S. A., and Sparling, P. F. (1992) Gonnococcal transferrin-binding protein 1 is required for transferrin utilization and is homologous to TonB-dependent outer membrane receptors. J Bacteriol 174: 5788–5797.

Finkelstein, R. A., Sciortino, C. V., and McIntosh, M. A. (1983) Role of iron in microbe-host interactions. Rev Infect Dis 5: S759–S777.

Fuller, C. A., Retzer, M. D., Jacobs, E., and Schryvers, A. B. (1996) Evidence for a bi-lobed structure for meningococcal transferrin binding protein B. In Pathogenic Neisseria. Zollinger, W. D., Frasch, C. E., and Deal, C. D. (eds). Abstract book from the 10th Pathogenic Neisseria Conference. pp 572–573.

Genco, C. A., Chen, C. Y., Arko, R. J., Kapczynski, D. R, and Morse, S. A. (1991) Isolation and characterization of a mutant of Neisseria gonorrhoeae that is defective in the uptake of iron from transferrin and hemoglobin and is avirulent in mouse subcutaneous chambers. J Gen Microbiol 137: 1313–1321.

Gschwentner, C., Lassman, H., and Huettinger, M. (1997) Lactoferrin and its receptor(s): modulators of inflammation? Abstracts of Third International Conference on Lactoferrin. p.68.

Irwin, S. W., Averil, N. A., Cheng, C. Y., and Schryvers, A. B. (1993) Preparation and analysis of isogenic mutants in the transferrin receptor protein genes, tbpA and tbpB, from Neisseria meningitidis. Mol Microbiol 8: 1125–1133.

Jennings, M. P., van der Ley, P., Wilks, K. E., Maskell, D. J., Poolman, J. T., and Moxon, E. R. (1993) Cloning and molecular analysis of the galE gene of Neisseria meningitidis and its role in lipopolysaccharide biosynthesis. Mol Microbiol 10: 361–369.

Legrain, M., Marazin, V., Irwin, S. W., Bouchon, B., Quentin-Millet, M.-J., Jacobs, E., and Schryvers, A. B. (1993) Cloning and characterisation of Neisseria meningitidis genes encoding the transferrin-binding proteins Tbp1 and Tbp2. Gene 130: 73–80.

Lugtenberg, B., Meyers, J., Peters, R., van der Hoek, P., and van Alphen, L. (1975) Electrophoretic resolution of the "major outer membrane protein" of Escherichia coli K-12 into four bands. FEBS Lett. 58:254–258.

Pettersson, A., Kuipers, B., Peizer, M., Verhagen, E., Tiesjema, R. H., Tommassen, J., and Poolman, J. T. (1990) Monoclonal antibodies against the 70-kilodalton iron-regulated protein of Neisseria meningitidis are bactericidal and strain specific. Infect Immun 58: 3036–3041.

Pettersson, A., van der Ley, P., Poolman, J. T., and Tommassen, J., (1993) Molecular characterization of the 98-kilodalton iron-regulated outer membrane protein of Neisseria meningitidis. Infect Immun 61: 4724–4733.

Pettersson, A., Klarenbeek, V., van Deurzen, J., Poolman, J. T., and Tommassen, J., (1994a) Molecular characterization of the structural gene for the lactorferrin receptor of the meningococcal strain H44/76. Microbial Pathogen 17: 395–408.

Pettersson, A., Maas, A., and Tommassen, J., (1994b) Identification of the iroA gene product of *Neisseria meningitidis* as a lactoferrin receptor. *J Bacteriol* 176: 1764–1766.

Renauld-Mongénie, G., Poncet, D., and Quentin-Millet, M. J. (1996) Study of human transferrin binding sites within the transferrin binding protein Tbp2 from *N. meningitidis* M982 using the pMAL expression system. In *Pathogenic Neisseria*. Zollinger, W. D., Frasch, C. E., and Deal, C. D. (eds). Abstract book from the 10th Pathogenic Neisseria Conference. pp 585–586.

Sambrook, J., Fritsch, E. F., and Maniatis, T. (1989) *Molecular cloning: a laboratory manual*. 2nd edn. Cold Spring Harbor, N.Y.: Cold Spring Harbor Laboratory Press.

Schryvers, A. B., and Morris, L. J. (1988) Identification and characterization of the human lactoferrin-binding protein from *Neisseria meningitidis*. *Infect Immun* 56: 1144–1149.

Tommasen, J., and Lugtenberg, B. (1980) Outer membrane protein e of *Escherichia coli* K-12 is co-regulated with alkaline phosphatase. *J. Bacteriol.* 143:151–157.

Tommassen, J., van Tol, H., and Lugtenberg, B. (1983) The ultimate localization of an outer membrane protein of *Escherichia coli* K-12 is not determined by the signal sequence. *EMBO J.* 2:1275–1279.

van Berkel, P. H. C., Geerts, M. E. J., van Veen, H. A., Kooiman, P. M., Pieper, F. R, de Boer, H. A., and Nuijens, J. H. (1995) Glycosylated and unglycosylated human lactoferrins both bind iron and show identical affinities towards human lysozyme and bacterial polysaccharide, but differ in their susceptibilities towards tryptic proteolysis. *Biochem J* 312: 107–114.

van der Ley, P., Heckels, J. E., Virji, M., Hoogerhout, P., and Poolman, J. T. (1991) Topology of outer membrane porins in pathogenic *Neisseria* spp. *Infect Immun* 59: 2963–2971.

van der Ley, P., and Poolman, J. T. (1992) Construction of a multivalent meningococcal strain based on the class I outer membrane protein. *Infect Immun* 60: 3156–3161.

von Heijne, G. (1989) The structure of signal peptides from bacterial lipoproteins. *Prot Eng* 2: 531–534.

Young, R. A., and Davis, R. W. (1983) Yeast RNA polymerase II genes: isolation and antibody probes. *Science* 222: 778–782.

What is claimed is:

1. An isolated polynucleotide comprising the nucleotide sequence set forth in SEQ ID NO: 1 (from nucleotide 100 to nucleotide 2274); SEQ ID NO: 3; SEQ ID NO: 5; SEQ ID NO: 7; or SEQ ID NO: 9.

2. An isolated polynucleotide comprising a polynucleotide sequence which encodes a polypeptide comprising the amino acid sequence set forth in SEQ ID NO: 2, 4, 6, 8 or 10.

3. A recombinant expression system comprising the polynucleotide of claims 1 or 2, wherein said expression system is capable of producing a polypeptide comprising an amino acid sequence set forth in SEQ ID NO: 2, 4, 6, 8 or 10.

4. A host cell comprising the recombinant expression system of claim 3.

5. A process for producing a polypeptide comprising the amino acid sequence set forth in SEQ ID NO: 2, 4, 6, 8 or 10 in a compatible host cell, comprising culturing the host cell of claim 4 under conditions sufficient for the production of said polypeptide and recovering the polypeptide from the culture.

6. A process for producing a host cell which produces a polypeptide comprising the amino acid sequence set forth in SEQ ID NO: 2, 4, 6, 8 or 10, comprising transforming or transfecting said host cell with the recombinant expression system of claim 3 such that the host cell, under appropriate culture conditions, produces the polypeptide.

7. A kit for diagnosing infection with *N. meningitidis* bacteria in a human comprising an isolated polynucleotide of claim 1 or 2.

8. An isolated polynucleotide having at least 90% identity to a polynucleotide sequence set forth in SEQ ID NO: 1 (from nucleotide 100 to nucleotide 2274); SEQ ID NO: 3; SEQ ID NO: 5; SEQ ID NO: 7; or SEQ ID NO: 9; whereby said isolated polynucleotide can detect *N. meningitidis* DNA under stringent hybridization conditions, in which the stringent hybridization conditions are defined as overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA, followed by washing in 0.1×SSC at about 65° C.

* * * * *